(12) United States Patent
Mabire et al.

(10) Patent No.: US 7,629,468 B2
(45) Date of Patent: Dec. 8, 2009

(54) METABOTROPIC GLUTAMATE RECEPTOR ANTAGONISTS

(75) Inventors: Dominique Jean-Pierre Mabire, La Saussaye (FR); Marc Venet Gaston, Le Mesnil-Esnard (FR); Sophie Philippe Coupa, Le Manoir sure Seine (FR); Alain Philippe Poncelet, Le Manoir (FR); Anne Simone Josephine Lesage, Halle-Zoersel (FR)

(73) Assignee: Janssen Pharmaceutica NV, Beerse (BE)

( * ) Notice: Subject to any disclaimer, the term of this patent is extended or adjusted under 35 U.S.C. 154(b) by 564 days.

(21) Appl. No.: 11/133,678

(22) Filed: May 20, 2005

(65) Prior Publication Data

US 2005/0209273 A1    Sep. 22, 2005

Related U.S. Application Data

(62) Division of application No. 10/381,987, filed on Aug. 14, 2003, now Pat. No. 7,115,630.

(51) Int. Cl.
    C07D 215/38    (2006.01)
(52) U.S. Cl. ........................... 546/163; 546/159
(58) Field of Classification Search ............ 546/163, 546/159; 514/312
    See application file for complete search history.

(56) References Cited

U.S. PATENT DOCUMENTS

| | | | | |
|---|---|---|---|---|
| 4,476,132 A | | 10/1984 | Goschke et al. | 424/258 |
| 4,845,100 A | * | 7/1989 | Abiko et al. | 514/253.07 |
| 5,306,719 A | * | 4/1994 | Tamada et al. | 514/253.07 |
| 5,541,325 A | | 7/1996 | Freyne et al. | 544/363 |
| 5,591,751 A | * | 1/1997 | Fujioka et al. | 514/312 |
| 6,080,764 A | * | 6/2000 | Chihiro et al. | 514/342 |

FOREIGN PATENT DOCUMENTS

| | | |
|---|---|---|
| DE | 198 59 750 A1 | 6/2000 |
| EP | 1 262 195 A1 | 12/2002 |
| JP | 60019767 * | 1/1985 |
| JP | 2 000 169 450 | 6/2000 |
| WO | WO 97/44339 | 11/1997 |
| WO | WO 99/03822 | 1/1999 |
| WO | WO 99/26927 | 6/1999 |
| WO | WO 00/12498 | 3/2000 |
| WO | WO 00/39082 | 7/2000 |
| WO | WO 02/28837 | 4/2002 |

OTHER PUBLICATIONS

Fujita, CA 120:217224, abstract only of Annual Report of the Tohoku College of Pharmacy, vol. 39, pp. 91-99, 1992.*
Tominaga, CA 106:102057, abstract only of Chemical & Pharmacetuical Bulletin, vol. 34(2), pp. 682-693, 1986.*
Fujita, CA 113:152215, abstract only of Yakugaku Zasshi, vol. 110(6), pp. 449-452, 1990.*
Tomisawa, CA 81:151956, abstract only of Chem & Pharm Bull, vol. 22(9), pp2091-2096, 1974.*
Tomisawa, CA 83:43155, abstract only of Chem & Pharm Bull, vol. 23(3), pp. 592-596, 1975.*
Goudet, Pain, vol. 137, pp. 112-124, 2008.*
Bie, J of Neuroscience, vol. 23(19), pp. 7262-7268, Aug. 2003.*
Bhatt, D.J. et al., "Studies on Chalcones: Preparation and Antimicrobial Activity of 2-Aryl-4-carboxy-6-acetylquinoline and 2-Aryl-4-carboxy-6-benzalacetoquinolines", *Journal of the Indian Chemical Society*, 1984, 61(9), 816-818.
Dabhi, T.P. et al., "Potential Antimicrobial Agents: Synthesis of N, N-Diaryl/N, N-Dialkyl/N-Aryl-N-Alkyl-(2-Aryl/Styry1-6-Acetylquinolin-4-YL)-Formamides", *Indian Journal of Heterocyclic Chemistry*, 1992, 2, 137-138.

* cited by examiner

*Primary Examiner*—D. Margaret Seaman
(74) *Attorney, Agent, or Firm*—Woodcock Washburn, LLP

(57) ABSTRACT

The present invention concerns compounds of formula. In a preferable embodiment, X represents O; $R^1$ represents $C_{1-6}$alkyl; cycloC$_{3-12}$alkyl or (cycloC$_{3-12}$alkyl)C$_{1-6}$alkyl, wherein one or more hydrogen atoms in a $C_{1-6}$alkyl-moiety or in a cycloC$_{3-12}$alkyl-moiety optionally may be replaced by $C_{1-6}$alkyloxy, aryl, halo or thienyl; $R^2$ represents hydrogen; halo; $C_{1-6}$alkyl or amino; $R^3$ and $R^4$ each independently represent hydrogen or $C_{1-6}$alkyl; or $R^2$ and $R^3$ may be taken together to form —$R^2$—$R^3$—, which represents a bivalent radical of formula -$Z_4$-CH$_2$—CH$_2$—CH$_2$— or -$Z_4$-CH$_2$—CH$_2$— with $Z_4$ being O or NR$^{11}$ wherein R$^{11}$ is C$_{1-6}$alkyl; and wherein each bivalent radical is optionally substituted with $C_{1-6}$alkyl; or $R^3$ and $R^4$ may be taken together to form a bivalent radical of formula —CH$_2$—CH$_2$—CH$_2$—CH$_2$—; $R^5$ represents hydrogen; Y represents O; and aryl represents phenyl optionally substituted with halo. The invention also relates to the use of a compound according to the invention as a medicament and in the manufacture of a medicament for treating or preventing glutamate-induced diseases of the central nervous system, as well as formulations comprising such a compound and processes for preparing such a compound.

9 Claims, No Drawings

METABOTROPIC GLUTAMATE RECEPTOR ANTAGONISTS

CROSS REFERENCE TO RELATED APPLICATIONS

This application is a divisional of application Ser. No. 10/381,987, now allowed, which is a National Stage application under 35 U.S.C. §371 of PCT/EP01/11135 filed Sep. 25, 2001, which claims priority from EP 00203419.7, filed Oct. 2, 2000.

The present invention is concerned with quinoline and quinolinone derivatives showing metabotropic glutamate receptor antagonistic activity and their preparation; it further relates to compositions comprising them, as well as their use as a medicine.

The neurotransmitter glutamate is considered to be the major excitatory neurotransmitter in the mammalian central nervous system. The binding of this neurotransmitter to metabotropic glutamate receptors (mGluRs), which are a subfamily of the G-protein-coupled receptors and which comprise 8 distinct subtypes of mGluRs, namely mGluR1 through mGluR8, activates a variety of intracellular second messenger systems. The mGluRs can be divided into 3 groups based on amino acid sequence homology, the second messenger system utilized by the receptors and the pharmacological characteristics. Group I mGluRs, which comprises mGluR subtype 1 and 5, couple to phospholipase C and their activation leads to intracellular calcium-ion mobilization. Group II mGluRs (mGluR2 and 3) and group III mGluRs (mGluR4, 6, 7 and 8) couple to adenyl cyclase and their activation causes a reduction in second messenger cAMP and as such a dampening of the neuronal activity. Treatment with Group I mGluR antagonists has been shown to translate in the presynapse into a reduced release of neurotransmitter glutamate and to decrease the glutamate-mediated neuronal excitation via postsynaptic mechanisms. Since a variety of pathophysiological processes and disease states affecting the central nervous system are thought to be due to excessive glutamate induced excitation of the central nervous system neurons, Group I mGluR antagonists could be therapeutically beneficial in the treatment of central nervous system diseases.

WO 99/26927 discloses antagonists of Group I mGlu receptors for treating neurological diseases and disorders, based—among others—on a quinoline structure.

WO 99/03822 discloses bicyclic metabotropic glutamate receptor ligands, none of them based on a quinoline or quinolinone structure.

The present invention concerns compounds of formula

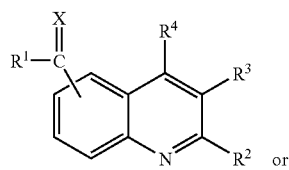

(I-A)

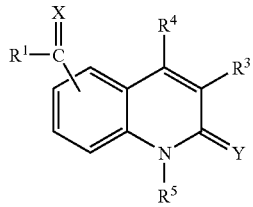

(I-B)

an N-oxide form, a pharmaceutically acceptable addition salt, a quatenary amine and a stereochemically isomeric form thereof, wherein X represents O; $C(R^6)_2$ with $R^6$ being hydrogen, aryl or $C_{1-6}$alkyl optionally substituted with amino or mono- or di($C_{1-6}$alkyl)amino; S or N—$R^7$ with $R^7$ being amino or hydroxy;

$R^1$ represents $C_{1-6}$alkyl; aryl; thienyl; quinolinyl; cyclo$C_{3-12}$alkyl or (cyclo$C_{3-12}$alkyl)$C_{1-6}$alkyl, wherein the cyclo$C_{3-12}$alkyl moiety optionally may contain a double bond and wherein one carbon atom in the cyclo$C_{3-12}$alkyl moiety may be replaced by an oxygen atom or an $NR^8$-moiety with $R^8$ being hydrogen, benzyl or $C_{1-6}$alkyloxycarbonyl; wherein one or more hydrogen atoms in a $C_{1-6}$alkyl-moiety or in a cyclo$C_{3-12}$alkyl-moiety optionally may be replaced by $C_{1-6}$alkyl, hydroxy$C_{1-6}$alkyl, halo$C_{1-6}$alkyl, amino$C_{1-6}$alkyl, hydroxy, $C_{1-6}$alkyloxy, aryl$C_{1-6}$alkyloxy, halo, $C_{1-6}$alkyloxycarbonyl, aryl, amino, mono- or di($C_{1-6}$alkyl)amino, $C_{1-6}$alkyloxycarbonylamino, halo, piperazinyl, pyridinyl, morpholinyl, thienyl or a bivalent radical of formula —O—, —O—$CH_2$—O— or —O—$CH_2$—$CH_2$—O—; or a radical of formula (a-1)

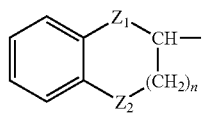

a-1 wherein
$Z_1$ is a single covalent bond, O, NH or $CH_2$;
$Z_2$ is a single covalent bond, O, NH or $CH_2$;
n is an integer of 0, 1, 2 or 3;
and wherein each hydrogen atom in the phenyl ring independently may optionally be replaced by halo, hydroxy, $C_{1-6}$alkyl, $C_{1-6}$alkyloxy or hydroxy$C_{1-6}$alkyl;

or X and $R^1$ may be taken together with the carbon atom to which X and $R^1$ are attached to form a radical of formula (b-1), (b-2) or (b-3);

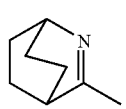

b-1

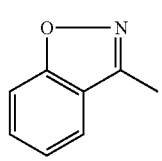

b-2

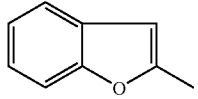
(b-3)

$R^2$ represents hydrogen; halo; cyano; $C_{1-6}$alkyl; $C_{1-6}$alkyloxy; $C_{1-6}$alkylthio; $C_{1-6}$alkylcarbonyl; $C_{1-6}$alkyloxycarbonyl; $C_{1-6}$alkylcarbonyloxy$C_{1-6}$alkyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di($C_{1-6}$alkyl)amino; mono- or di($C_{1-6}$alkyloxy$C_{1-6}$alkyl)amino; mono- or di($C_{1-6}$alkylthio$C_{1-6}$alkyl)amino; aryl; aryl$C_{1-6}$alkyl; aryl$C_{2-6}$alkynyl; $C_{1-6}$alkyloxy$C_{1-6}$alkylamino$C_{1-6}$alkyl; aminocarbonyl optionally substituted with $C_{1-6}$alkyl, $C_{1-6}$alkyloxy$C_{1-6}$alkyl, $C_{1-6}$alkyloxycarbonyl$C_{1-6}$alkyl or pyridinyl$C_{1-6}$alkyl;

a heterocycle selected from thienyl, furanyl, pyrrolyl, thiazolyl, oxazolyl, imidazolyl, isothiazolyl, isoxazolyl, pyrazolyl, pyridyl, pyrazinyl, pyridazinyl, pyrimidinyl, piperidinyl and piperazinyl, optionally N-substituted with $C_{1-6}$alkyloxy$C_{1-6}$alkyl, morpholinyl, thiomorpholinyl, dioxanyl or dithianyl;

a radical —NH—C(=O)$R^9$ wherein $R^9$ represents
  $C_{1-6}$alkyl optionally substituted with cyclo$C_{3-12}$alkyl, $C_{1-6}$alkyloxy, $C_{1-6}$alkyloxycarbonyl, aryl, aryloxy, thienyl, pyridinyl, mono- or di($C_{1-6}$alkyl)amino, $C_{1-6}$alkylthio, benzylthio, pyridinylthio or pyrimidinylthio;
  cyclo$C_{3-12}$alkyl; cyclohexenyl; amino; arylcyclo$C_{3-12}$alkylamino; mono-or-di($C_{1-6}$alkyl )amino; mono- or di($C_{1-6}$alkyloxycarbonyl$C_{1-6}$alkyl)amino; mono- or di($C_{1-6}$alkyloxycarbonyl)amino; mono-or di($C_{2-6}$alkenyl)amino; mono- or di(aryl$C_{1-6}$alkyl)amino; mono- or diarylamino; aryl$C_{2-6}$alkenyl; furanyl$C_{2-6}$alkenyl; piperididinyl; piperazinyl; indolyl; furyl; benzofuryl; terahydrofuryl; indenyl; adamantyl; pyridinyl; pyrazinyl; aryl; aryl$C_{1-6}$alkylthio or a radical of formula (a-1);
a sulfonamid —NH—$SO_2$—$R^{10}$ wherein $R^{10}$ represents $C_{1-6}$alkyl, mono- or poly halo$C_{1-6}$alkyl, aryl$C_{1-6}$alkyl, aryl$C_{2-6}$alkenyl, aryl, quinolinyl, isoxazolyl or di($C_{1-6}$alkyl)amino;

$R^3$ and $R^4$ each independently represent hydrogen; halo; hydroxy; cyano; $C_{1-6}$alkyl; $C_{1-6}$alkyloxy; $C_{1-6}$alkyloxy$C_{1-6}$alkyl; $C_{1-6}$alkylcarbonyl; $C_{1-6}$alkyloxycarbonyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di($C_{1-6}$alkyl)amino; mono- or di($C_{1-6}$alkyloxy$C_{1-6}$alkyl)amino; mono- or di($C_{1-6}$alkylthio$C_{1-6}$alkyl)amino; aryl; morpholinyl$C_{1-6}$alkyl or piperidinyl $C_{1-6}$alkyl; or $R^2$ and $R^3$ may be taken together to form —$R^2$—$R^3$—, which represents a bivalent radical of formula —$(CH_2)_3$—, —$(CH_2)_4$—, —$(CH_2)_5$—, —$(CH_2)_6$—, —CH=CH—CH=CH—, -$Z_4$-CH=CH—, —CH=CH-$Z_4$-, -$Z_4$-$CH_2$—$CH_2$—$CH_2$—, —$CH_2$-$Z_4$-$CH_2$—$CH_2$—, —$CH_2$—$CH_2$-$Z_4$-$CH_2$—, —$CH_2$—$CH_2$—$CH_2$-$Z_4$-, -$Z_4$-$CH_2$—$CH_2$—, —$CH_2$-$Z_4$-$CH_2$— or —$CH_2$—$CH_2$-$Z_4$-, with $Z_4$ being O, S, $SO_2$ or $NR^{11}$ wherein $R^{11}$ is hydrogen, $C_{1-6}$alkyl, benzyl or $C_{1-6}$alkyloxycarbonyl; and wherein each bivalent radical is optionally substituted with $C_{1-6}$alkyl.

or $R^3$ and $R^4$ may be taken together to form a bivalent radical of formula —CH=CH—CH=CH— or —$CH_2$—$CH_2$—$CH_2$—$CH_2$—;

$R^5$ represents hydrogen; cyclo$C_{3-12}$alkyl; piperidinyl; oxothienyl; tetrahydrothienyl; aryl$C_{1-6}$alkyl; $C_{1-6}$alkyloxy$C_{1-6}$alkyl; $C_{1-6}$alkyloxycarbonyl$C_{1-6}$alkyl or $C_{1-6}$alkyl optionally substituted with a radical C(=O)$NR_xR_y$, in which $R_x$ and $R_y$, each independently are hydrogen, cyclo$C_{3-12}$alkyl, $C_{2-6}$alkynyl or $C_{1-6}$alkyl optionally substituted with cyano, $C_{1-6}$alkyloxy, $C_{1-6}$alkyloxycarbonyl, furanyl, pyrrolidinyl, benzylthio, pyridinyl, pyrrolyl or thienyl;

Y represents O or S;

or Y and $R^5$ may be taken together to form =Y—$R^5$— which represents a radical of formula —CH=N—N= (c-1);

—N=N—N= (c-2); or

—N—CH=CH— (c-3).

aryl represents phenyl or naphthyl optionally substituted with one or more substituents selected from halo, hydroxy, $C_{1-6}$alkyl, $C_{1-6}$alkyloxy, phenyloxy, nitro, amino, thio, $C_{1-6}$alkylthio, halo$C_{1-6}$alkyl, polyhalo$C_{1-6}$alkyl, polyhalo$C_{1-6}$alkyloxy, hydroxy$C_{1-6}$alkyl, $C_{1-6}$alkyloxy$C_{1-6}$alkyl, amino$C_{1-6}$alkyl, mono- or di($C_{1-6}$alkyl)amino; mono- or di($C_{1-6}$alkyl)amino$C_{1-6}$alkyl, cyano, —CO—$R^{12}$, —CO—$OR^{13}$, —$NR^{13}SO_2R^{12}$, —$SO_2$—$NR^{13}R^{14}$, —$NR^{13}C(O)R^{12}$, —C(O)$NR^{13}R^{14}$, —$SOR^{12}$, —$SO_2R^{12}$; wherein each $R^{12}$, $R^{13}$ and $R^{14}$ independently represent $C_{1-6}$alkyl; cyclo$C_{3-6}$alkyl; phenyl; phenyl substituted with halo, hydroxy, $C_{1-6}$alkyl, $C_{1-6}$alkyloxy, halo$C_{1-6}$alkyl, polyhalo$C_{1-6}$alkyl, furanyl, thienyl, pyrrolyl, imidazolyl, thiazolyl or oxazolyl;

and when the $R^1$—C(=X) moiety is linked to another position than the 7 or 8 position, then said 7 and 8 position may be substituted with $R^{15}$ and $R^{16}$ wherein either one or both of $R^{15}$ and $R^{16}$ represents $C_{1-6}$alkyl, $C_{1-6}$alkyloxy or $R^{15}$ and $R^{16}$ taken together may form a bivalent radical of formula —CH=CH—CH=CH—.

As used in the foregoing definitions and hereinafter $C_{1-6}$alkyl as a group or part of a group encompasses the straight and branched chain saturated hydrocarbon radicals having from 1 to 6 carbon atoms such as, for example, methyl, ethyl, propyl, butyl, pentyl or hexyl; $C_{2-6}$alkenyl as a group or part of a group encompasses the straight and branched chain hydrocarbon radicals having from 2 to 6 carbon atoms and having a double bond such as ethenyl, propenyl, butenyl, pentenyl, hexenyl, 3-methylbutenyl and the like; $C_{2-6}$alkynyl as a group or part of a group defines straight or branched chain hydrocarbon radicals having from 2 to 6 carbon atoms and having a triple bond such as ethynyl, propynyl, butynyl, pentynyl, hexynyl, 3-methylbutynyl and the like; cyclo$C_{3-6}$alkyl encompasses monocyclic alkyl ring structures such as cyclopropyl, cyclobutyl, cyclopentyl, and cyclohexyl; cyclo$C_{3-12}$alkyl encompasses mono-, bi- or tricyclic alkyl ring structures and is generic to for example cyclopropyl, cyclobutyl, cyclopentyl, cyclohexyl, cycloheptyl, cyclooctyl, norbornanyl, adamantyl.

The term halo is generic to fluoro, chloro, bromo and iodo. As used in the foregoing and hereinafter, polyhalo$C_{1-6}$alkyl as a group or part of a group is defined as mono- or polyhalosubstituted $C_{1-6}$alkyl, in particular methyl with one or more fluoro atoms, for example, difluoromethyl or trifluoromethyl. In case more than one halogen atoms are attached to an alkyl group within the definition of polyhalo$C_{1-6}$alkyl, they may be the same or different.

When any variable, e.g. aryl, occurs more than one time in any constituent, each definition is independent.

When any bond is drawn into a ring structure, it means that the corresponding substituent may be linked to any atom of said ring structure. This means for instance that the $R^1$—C (=X) moiety may be linked to the quinoline or quinolinone moiety in position 5, 6, 7, 8 but also position 3 or position 4.

For therapeutic use, salts of the compounds of formula (I-A) and (I-B) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I-A) and (I-B) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I-A) and (I-B) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I-A) and (I-B) are able to form. Examples of such forms are e.g. hydrates, alcoholates and the like.

The term "quaternary amine" as used hereinbefore defines the quaternary ammonium salts which the compounds of formula (I-A) and (I-B) are able to form by reaction between a basic nitrogen of a compound of formula (I-A) or (I-B) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that some of the compounds of formula (I-A) and (I-B) and their N-oxides, salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I-A) and (I-B), and their N-oxides, salts, quaternary amines or physiologically functional derivatives may possess. Unless otherwise mentioned or indicated, the chemical designation of compounds denotes the mixture of all possible stereoisomeric forms, said mixtures containing all diastereomers and enantiomers of the basic molecular structure as well as each of the individual isomeric forms of formula (I-A) and (I-B) and their N-oxides, salts, solvates or quaternary amines substantially free, i.e. associated with less than 10%, preferably less than 5%, in particular less than 2% and most preferably less than 1% of the other isomers. Stereochemically isomeric forms of the compounds of formula (I-A) and (I-B) are obviously intended to be embraced within the scope of the present invention. The same applies to the intermediates as described herein, used to prepare end products of formula (I-A) and (I-B).

The terms cis and trans are used herein in accordance with Chemical Abstracts nomenclature.

In some compounds of formula (I-A) and (I-B) and in the intermediates used in their preparation, the absolute stereochemical configuration has not been determined. In these cases, the stereoisomeric form which was first isolated is designated as "A" and the second as "B", without further reference to the actual stereochemical configuration. However, said "A" and "B" stereoisomeric forms can be unambiguously characterized by physicochemical characteristics such as their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the second as "A2" and "B2", without further reference to the actual stereochemical configuration.

The N-oxide forms of the present compounds are meant to comprise the compounds of formula (I-A) and (I-B) wherein one or several nitrogen atoms are oxidized to the so-called N-oxide.

Some of the compounds of formula (I-A) and (I-B) may also exist in their tautomeric form. Such forms although not explicitly indicated in the above formula are intended to be included within the scope of the present invention.

Whenever used hereinafter, the term "compounds of formula (I-A) and (I-B)" is meant to also include their N-oxide forms, their salts, their quaternary amines and their stereochemically isomeric forms. Of special interest are those compounds of formula (I-A) and (I-B) which are stereochemically pure.

An interesting group of compounds are those compounds of formula (I-A) and (I-B) wherein X represents O; $C(R^6)_2$ with $R^6$ being hydrogen or aryl; or —$R^7$ with $R^7$ being amino or hydroxy;

$R^1$ represents $C_{1-6}$alkyl, aryl; thienyl; quinolinyl; cyclo$C_{3-12}$ alkyl or (cyclo$C_{3-12}$alkyl)$C_{1-6}$alkyl, wherein the cyclo $C_{3-12}$alkyl moiety optionally may contain a double bond and wherein one carbon atom in the cyclo$C_{3-12}$alkyl moiety may be replaced by an oxygen atom or an $NR^8$-moiety with $R^8$ being benzyl or $C_{1-6}$alkyloxycarbonyl; wherein one or more hydrogen atoms in a $C_{1-6}$alkyl-moiety or in a cyclo$C_{3-12}$alkyl-moiety optionally may be replaced by $C_{1-6}$alkyl, halo$C_{1-6}$alkyl, hydroxy, $C_{1-6}$allyloxy, aryl$C_{1-6}$alkyloxy, halo, aryl, mono- or di($C_{1-6}$alkyl)amino, $C_{1-6}$alkyloxycarbonylamino, halo, piperazinyl, pyridinyl, morpholinyl, thienyl or a bivalent radical of formula —O— or —O—CH$_2$—CH$_2$—O—;

or a radical of formula (a-1)

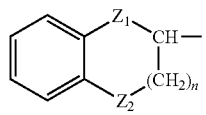

wherein
  $Z_1$ is a single covalent bond, O or CH$_2$;
  $Z_2$ is a single covalent bond, O or CH$_2$;
  n is an integer of 0, 1, or 2;
  and wherein each hydrogen atom in the phenyl ring independently may optionally be replaced by halo or hydroxy;

or X and $R^1$ may be taken together with the carbon atom to which X and $R^1$ are attached to form a radical of formula (b-1), (b-2) or (b-3);

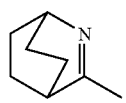

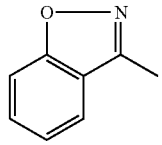

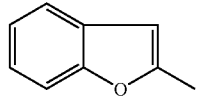

$R^2$ represents hydrogen; halo; cyano; $C_{1-6}$alkyl; $C_{1-6}$alkyloxy; $C_{1-6}$alkylthio; $C_{1-6}$alkylcarbonyl; $C_{1-6}$alkyloxycarbonyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di($C_{1-6}$alkyl)amino; mono- or di($C_{1-6}$ alkyloxy$C_{1-6}$alkyl)amino; mono- or di($C_{1-6}$alkylthio$C_{1-6}$ alkyl)amino; aryl; aryl$C_{1-6}$alkyl; aryl$C_{2-6}$alkynyl; $C_{1-6}$alkyloxy$C_{1-6}$alkylamino$C_{1-6}$alkyl; aminocarbonyl optionally substituted with $C_{1-6}$alkyloxycarbonyl$C_{1-6}$ alkyl; a heterocycle selected from thienyl, furanyl, thiazolyl and piperidinyl, optionally N-substituted with morpholinyl or thiomorpholinyl; a radical —NH—C(=O)$R^9$ wherein $R^9$ represents $C_{1-6}$alkyl optionally substituted with cyclo$C_{3-12}$alkyl, $C_{1-6}$alkyloxy, $C_{1-6}$alkyloxycarbonyl, aryl, aryloxy, thienyl, pyridinyl, mono- or di($C_{1-6}$alkyl) amino, $C_{1-6}$alkylthio, benzylthio, pyridinylthio or pyrimidinylthio; cyclo$C_{3-12}$alkyl; cyclohexenyl; amino; arylcyclo$C_{3-12}$alkylamino; mono-or-di($C_{1-6}$alkyl)amino; mono- or di($C_{1-6}$alkyloxycarbonyl$C_{1-6}$alkyl)amino; mono- or di($C_{1-6}$alkyloxycarbonyl)amino; mono-or di($C_{2-6}$alkenyl) amino; mono- or di(aryl$C_{1-6}$alkyl)amino; mono- or diarylamino; aryl$C_{2-6}$alkenyl; furanyl$C_{2-6}$alkenyl; piperididinyl; piperazinyl; indolyl; furyl; benzofuryl; tetrahydrofuryl; indenyl; adamantyl; pyridinyl; pyrazinyl; aryl or a radical of formula (a-1); a sulfonamid —NH— SO$_2$—$R^{10}$ wherein $R^{10}$ represents $C_{1-6}$alkyl, mono- or poly halo$C_{1-6}$alkyl, aryl$C_6$alkyl or aryl;

$R^3$ and $R^4$ each independently represent hydrogen; $C_{1-6}$alkyl; $C_{1-6}$alkyloxy$C_{1-6}$alkyl; $C_{1-6}$alkyloxycarbonyl; or $R^2$ and $R^3$ may be taken together to form —$R^2$—$R^3$—, which represents a bivalent radical of formula —(CH$_2$)$_4$—, —(CH$_2$)$_5$—, -$Z_4$-CH=CH—, -$Z_4$-CH$_2$—CH$_2$—CH$_2$— or -$Z_4$-CH$_2$—CH$_2$—, with $Z_4$ being O, S, SO$_2$ or NR$^{11}$ wherein $R^{11}$ is hydrogen, $C_{1-6}$alkyl, benzyl or $C_{1-6}$alkyloxycarbonyl; and wherein each bivalent radical is optionally substituted with $C_{1-6}$alkyl;

or $R^3$ and $R^4$ may be taken together to form a bivalent radical of formula —CH=CH—CH=CH— or —CH$_2$—CH$_2$— CH$_2$—CH$_2$—;

$R^5$ represents hydrogen; piperidinyl; oxo-thienyl; tetrahydrothienyl, aryl$C_{1-6}$alkyl; $C_{1-6}$alkyloxycarbonyl$C_{1-6}$alkyl or $C_{1-6}$alkyl optionally substituted with a radical C(=O) NR$_x$R$_y$, in which R$_x$ and R$_y$ each independently are hydrogen, cyclo$C_{3-12}$alkyl, $C_{2-6}$alkynyl or $C_{1-6}$alkyl optionally substituted with cyano, $C_{1-6}$alkyloxy or $C_{1-6}$alkyloxycarbonyl;

Y represents O or S;

or Y and $R^5$ may be taken together to form $=Y-R^5-$ which represents a radical of formula $-CH=N-N=$ (c-1); or $-N=N-N=$ (c-2);

aryl represents phenyl or naphthyl optionally substituted with one or more substituents selected from halo, $C_{1-6}$alkyloxy, phenyloxy, mono-or di($C_{1-6}$alkyl)amino and cyano;

and when the $R^1-C(=X)$ moiety is linked to another position than the 7 or 8 position, then said 7 and 8 position may be substituted with $R^{15}$ and $R^{16}$ wherein either one or both of $R^{15}$ and $R^{16}$ represents $C_{1-6}$alkyl or $R^{15}$ and $R^{16}$ taken together may form a bivalent radical of formula $-CH=CH-CH=CH-$.

A further most interesting group of compounds comprises those compounds of formula (I-A) and (I-B) wherein X represents O;

$R^1$ represents $C_{1-6}$alkyl; cyclo$C_{3-12}$alkyl or (cyclo$C_{3-12}$alkyl)$C_{1-6}$alkyl, wherein one or more hydrogen atoms in a $C_{1-6}$alkyl-moiety or in a cyclo$C_{3-12}$alkyl-moiety optionally may be replaced by $C_{1-6}$alkyloxy, aryl, halo or thienyl;

$R^2$ represents hydrogen; halo; $C_{1-6}$alkyl or amino;

$R^3$ and $R^4$ each independently represent hydrogen or $C_{1-6}$alkyl; or $R^2$ and $R^3$ may be taken together to form $-R^2-R^3-$, which represents a bivalent radical of formula -$Z_4$-$CH_2$-$CH_2$-$CH_2$- or -$Z_4$-$CH_2$-$CH_2$- with $Z_4$ being O or $NR^{11}$ wherein $R^{11}$ is $C_{1-6}$alkyl; and wherein each bivalent radical is optionally substituted with $C_{1-6}$alkyl;

or $R^3$ and $R^4$ may be taken together to form a bivalent radical of formula $-CH_2-CH_2-CH_2-CH_2-$;

$R^5$ represents hydrogen;

Y represents O; and aryl represents phenyl optionally substituted with halo.

A further interesting group of compounds comprises those compounds of formula (I-A) and (I-B) wherein the $R^1-C$ $(=X)$ moiety is linked to the quinoline or quinolinone moiety in position 6.

In order to simplify the structural representation of some of the present compounds and intermediates in the following preparation procedures, the quinoline or the quinolinone moiety will hereinafter be represented by the symbol Q.

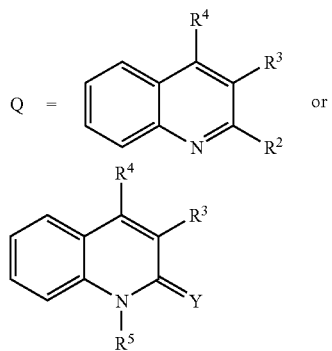

The compounds of formula (I-A) or (I-B), wherein X represents O, said compounds being represented by formula ($I_{A/B}$-a), can be prepared by oxidizing an intermediate of formula (II) in the presence of a suitable oxidizing agent, such as potassium permanganate, and a suitable phase-transfer catalyst, such as tris(dioxa-3,6-heptyl)amine, in a suitable reaction-inert solvent, such as for example dichloromethane.

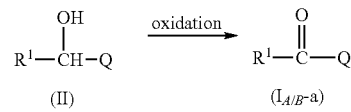

Compounds of formula ($I_{A/B}$-a) may also be prepared by reacting an intermediate of formula (III) with an intermediate of formula (IV), wherein $W_1$ represents a halo atom, e.g. bromo, in the presence of butyl lithium and a suitable reaction-inert solvent, such as for example tetrahydrofuran.

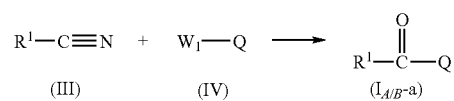

Alternatively, compounds of formula ($I_{A/B}$-a) may also be prepared by reacting an intermediate of formula (V) with an intermediate of formula (IV) in the presence of butyl lithium and a suitable reaction-inert solvent, such as for example tetrahydrofuran.

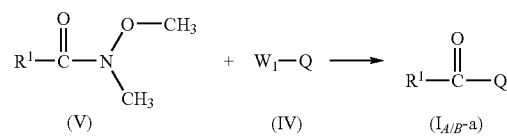

Compounds of formula ($I_{A/B}$-a), wherein the $R^1$ substituent is linked to the carbonyl moiety via an oxygen atom, said $R^1$ substituent being represented by O—$R^{1a}$ and said compounds by formula ($I_{A/B}$-a-1), can be prepared by reacting an intermediate of formula (VI) with an intermediate of formula (VII) in the presence of a suitable acid, such as sulfuric acid.

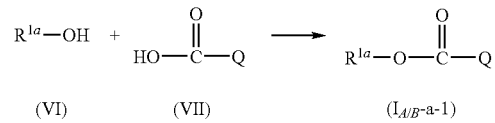

Compounds of formula (I-A), wherein $R^2$ represents methylcarbonyl, said compounds being represented by formula (I-A-1), can be prepared by reacting an intermediate of formula (VIII) in the presence of a suitable acid, such as hydrochloric acid, and a suitable reaction-inert solvent, such as for example tetrahydrofuran.

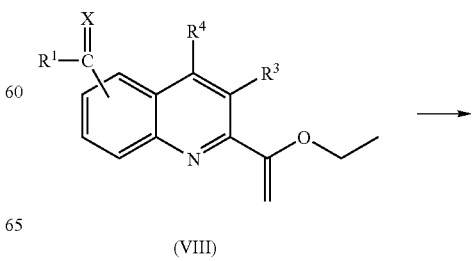

-continued

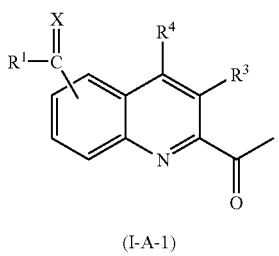

(I-A-1)

The compounds of formula (I) may also be converted into each other following art-known transformations.

Compounds of formula (I-A) wherein $R^2$ is a halo atom, such as chloro, can be converted into a compound of formula (I-A), wherein $R^2$ is another halo atom, such as fluoro or iodo, by reaction with a suitable halogenating agent, such as for example potassium fluoride or sodium iodide, in the presence of a suitable reaction-inert solvent, e.g. dimethyl sulfoxide or acetonitrile and optionally in the presence of acetyl chloride.

Compounds of formula (I-A), wherein $R^2$ is a suitable leaving group, such as a halo atom, e.g. chloro, iodo, said leaving group being represented by $W^2$ and said compounds by (I-A-2), can be converted into a compound of formula (I-A) wherein $R^2$ is cyano, said compound being represented by formula (I-A-3), by reaction with a suitable cyano-introducing agent, such as for example trimethylsilanecarbonitrile, in the presence of a suitable base such as N,N-diethylethanamine and a suitable catalyst, such as for example tetrakis(triphenylphosphine)palladium.

Compounds of formula (I-A-2) can also be converted into a compound of formula (I-A-4) by reaction with $C_{2-6}$alkynyl-tri($C_{1-6}$alkyl)silane in the presence of CuI, an appropriate base, such as for example N,N-ethylethanamine, and an appropriate catalyst, such as for example tetrakis(triphenylphosphine)palladium. Compounds of formula (I-A-4) can on their turn be converted into a compound of formula (I-A-5) by reaction with potassium fluoride in the presence of a suitable acid such as acetic acid, or by reaction with a suitable base, such as potassium hydroxide, in the presence of a suitable reaction-inert solvent, such as an alcohol, e.g. methanol and the like.

Compounds of formula (I-A-2) can also be converted into a compound of formula (I-A-6) by reaction with an intermediate of formula (IX) in the presence of CuI, a suitable base, such as for example N,N-diethylethanamine, and a suitable catalyst such as tetrakis(triphenylphosphine)palladium.

Compounds of formula (I-A-2) can also be converted into a compound wherein $R^2$ is $C_{1-6}$alkyl, said compound being represented by formula (I-A-8) in the presence of a suitable alkylating agent, such as for example $Sn(C_{1-6}alkyl)_4$, or into a compound wherein $R^2$ is $C_{2-6}$alkenyl, said compound being represented by formula (I-A-9) in the presence of a suitable alkenylating agent, such as for example $Sn(C_{2-6}alkenyl)(C_{1-6}alkyl)_3$, both reactions in the presence of a suitable catalyst, such as for example tetrakis(triphenylphosphine)palladium and a reaction-inert solvent, such as for example toluene or dioxane.

Compounds of formula (I-A-2) can also be converted into a compound of formula (I-A-7) wherein Z represents O or S, by reaction with an intermediate of formula (X) optionally in the presence of a suitable base such as dipotassium carbonate and a reaction-inert solvent, such as N,N-dimethyl formamide.

Compounds of formula (I-A-2) can also be converted into a compound of formula (I-A), wherein $R^2$ is $C_{1-6}$alkyloxycarbonyl, said compound being represented by formula (I-A-10) and a compound of formula (I-A), wherein $R^2$ is hydrogen, said compound being represented by formula (I-A-11), by reaction with a suitable alcohol of formula $C_{1-6}$alkylOH and CO in the presence of a suitable catalyst, such as for example palladium(II)acetate, triphenylphosphine, a suitable base such as dipotassium carbonate and a reaction-inert solvent, such as N,N-dimethylformamide.

Compounds of formula (I-A-11) can also be prepared by reacting a compound of formula (I-A-2) with Zn in the presence of a suitable acid such as acetic acid.

Compounds of formula (I-A-2) can also be converted into a compound of formula (I-A), wherein $R^2$ is aminocarbonyl substituted with $C_{1-6}$alkyloxycarbonyl$C_{1-6}$alkyl, said compound being represented by formula (I-A-12), by reaction with an intermediate of formula $H_2N-C_{1-6}alkyl-C(=O)-O-C_{1-6}alkyl$ in the presence of CO, a suitable catalyst such as tetrakis(triphenylphosphine)palladium, a suitable base, such as for example N,N-diethylethanamine, and a suitable reaction-inert solvent, such as for example toluene.

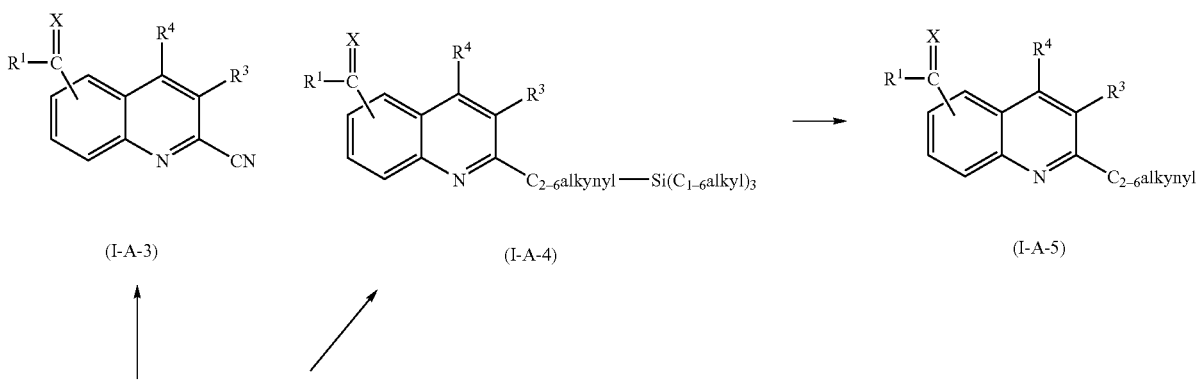

(I-A-3)  (I-A-4)  (I-A-5)

-continued

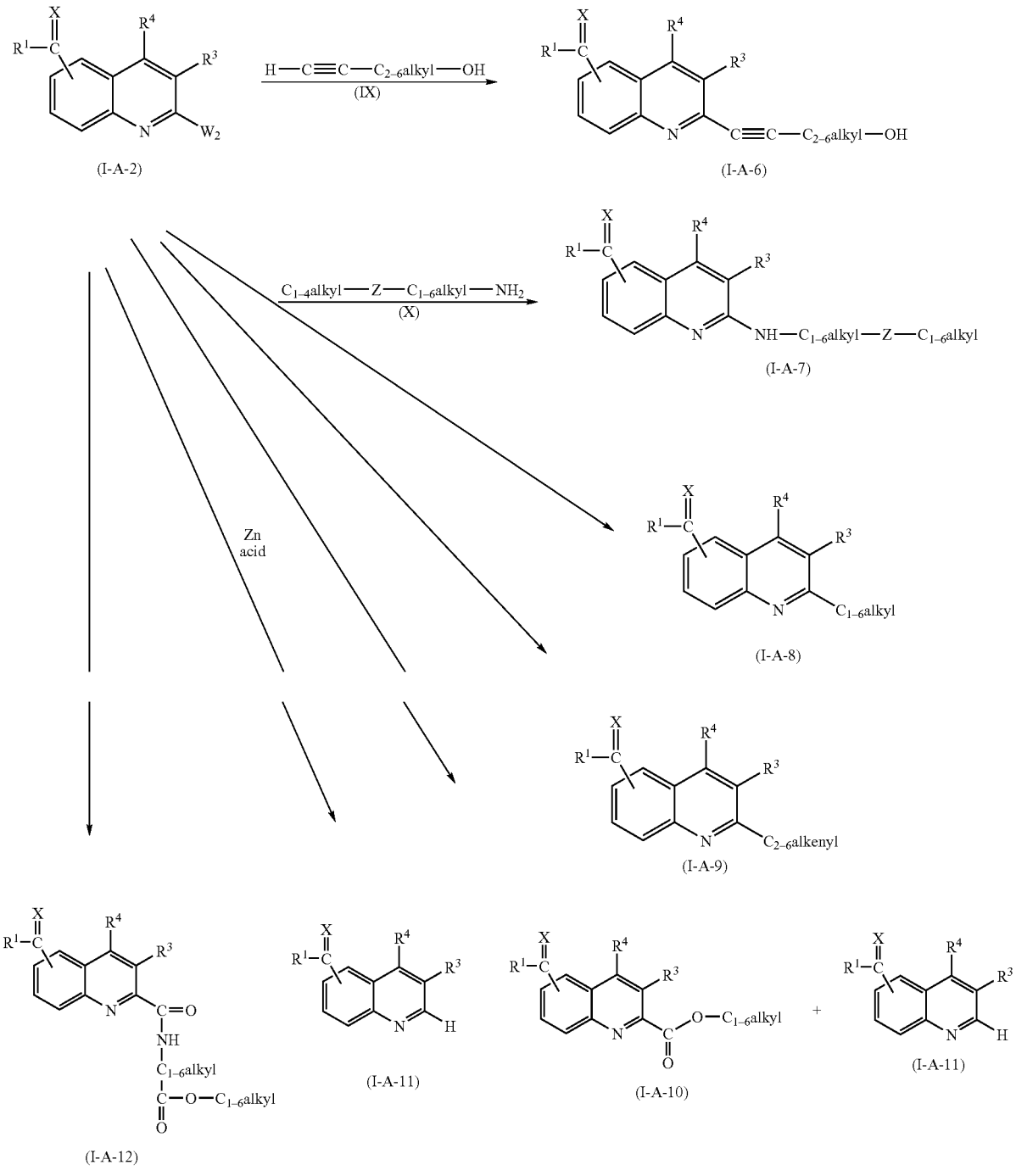

Compounds of formula (I-A-2) can also be converted into a compound of formula (I-A) wherein $R^2$ is aryl or a heterocycle selected from the group described in the definition of $R^2$ hereinabove, said $R^2$ being represented by $R^{2a}$ and said compound by formula (I-A-13) by reaction with an intermediate of formula (XI), (XII) or (XIII) in the presence of a suitable catalyst such as for example tetrakis(triphenylphosphine)palladium and a suitable reaction-inert solvent, such as for example dioxane.

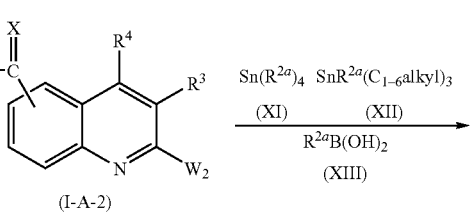

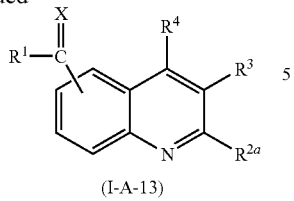

(I-A-13)

Compounds of formula (I-A-2) can also be converted into a compound of formula (I-B), wherein Y and $R^5$ are taken together to form a radical of formula (b-1) or (b-2), said compound being represented by formula (I-B-1) or (I-B-2), by reaction with hydrazincarboxaldehyde or sodium azide in a suitable reaction-inert solvent, such as an alcohol, e.g. butanol, or N,N-diethylformamide.

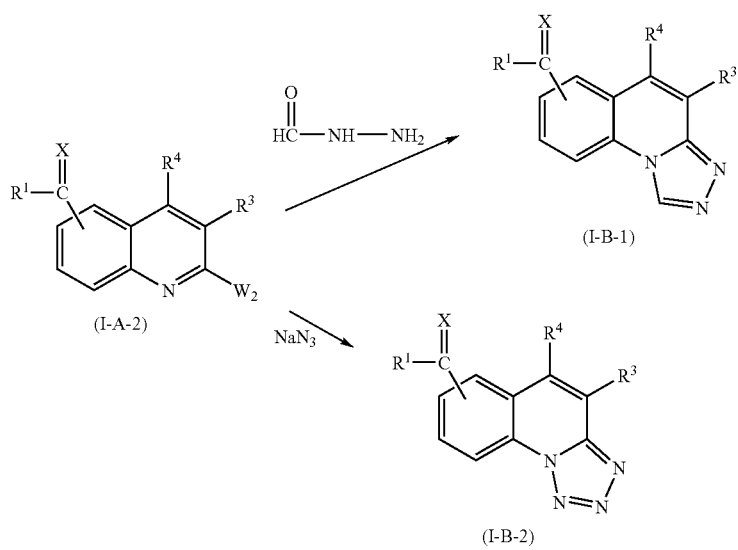

Compounds of formula (I-A-11) can be converted into the corresponding N-oxide, represented by formula (I-A-14), by reaction with a suitable peroxide, such as 3-chloro-benzenecarboperoxoic acid, in a suitable reaction-inert solvent, such as for example methylene chloride. Said compound of formula (I-A-14) can further be converted into a compound of formula (I-B), wherein $R^5$ is hydrogen, said compound being represented by formula (I-B-3), by reaction with 4-methylbenzene sulfonyl chloride in the presence of a suitable base, such as for example dipotassium carbonate and a suitable reaction-inert solvent, such as for example methylene chloride.

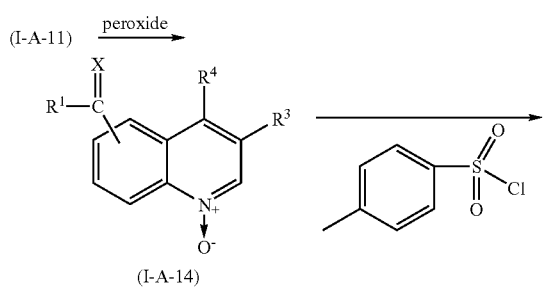

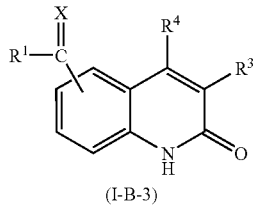

(I-B-3)

Compounds of formula (I-B-3) can also be prepared from a compound of formula (I-A), wherein $R^2$ is $C_{1-6}$alkyloxy, said compound being represented by formula (I-A-15), by reaction with a suitable acid, such as hydrochloric acid, in the presence of a suitable reaction-inert solvent, such as for example tetrahydrofuran.

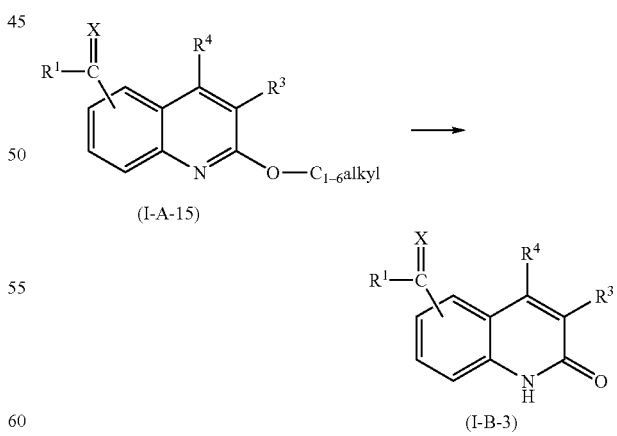

Compounds of formula (I-B-3) can be converted into a compound of formula (I-B), wherein $R^5$ represents $C_{1-6}$alkyl, said compound being represented by formula (I-B-4), by reaction with an appropriate alkylating agent, such as for example an intermediate of formula (XIV), wherein $W_3$ represents a suitable leaving group such as a halo atom e.g. iodo, in the presence of potassium tert. butoxide and in the presence of a suitable reaction-inert solvent, such as for example tetrahydrofuran.

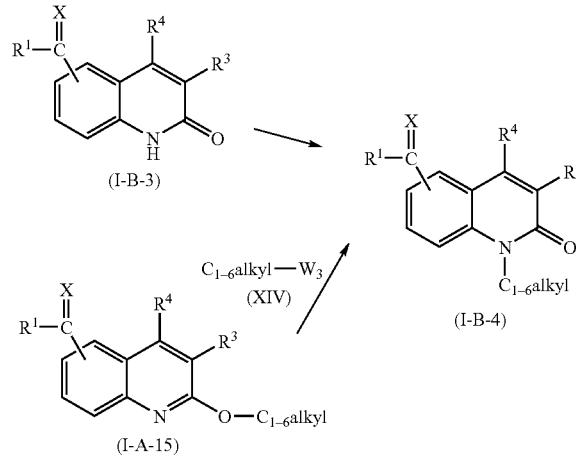

Compounds of formula (I-B-3) can also be converted into a compound of formula (I-B), wherein $R^5$ is $C_{1-6}$alkyloxycarbonyl$C_{1-6}$alkyl or aryl$C_{1-6}$alkyl, said $R^5$ being represented by $R^{5a}$ and said compound being represented by formula (I-B-5), by reaction with an intermediate of formula (XV), wherein $W_4$ represents a suitable leaving group, such as a halo atom, e.g. bromo, chloro and the like, in the presence of a suitable base, such as for example sodium hydride and a suitable reaction-inert solvent, such as for example N,N-dimethylformamide.

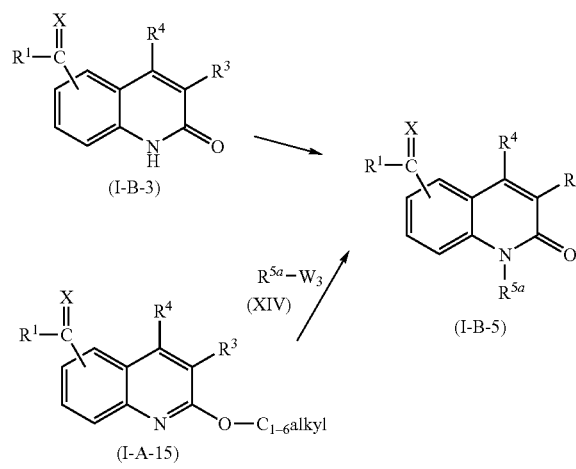

Compounds of formula (I-A-2) can also be converted into a compound of formula (I-B), wherein $R^5$ is hydrogen and Y is S, said compound being represented by formula (I-B-6), by reaction with $H_2N-C(=S)-NH_2$ in the presence of a suitable base, such as potassium hydroxide, and a suitable reaction-inert solvent, such as an alcohol, for example ethanol, or water. Compounds of formula (I-B-6) can further be converted into a compound of formula (I-A), wherein $R^2$ is $C_{1-6}$alkylthio, said compound being represented by formula (I-A-16), by reaction with a suitable $C_{1-6}$alkylhalide, such as for example $C_{1-6}$alkyliodide, in the presence of a suitable base, such as dipotassium carbonate, and a suitable solvent, such as for example acetone.

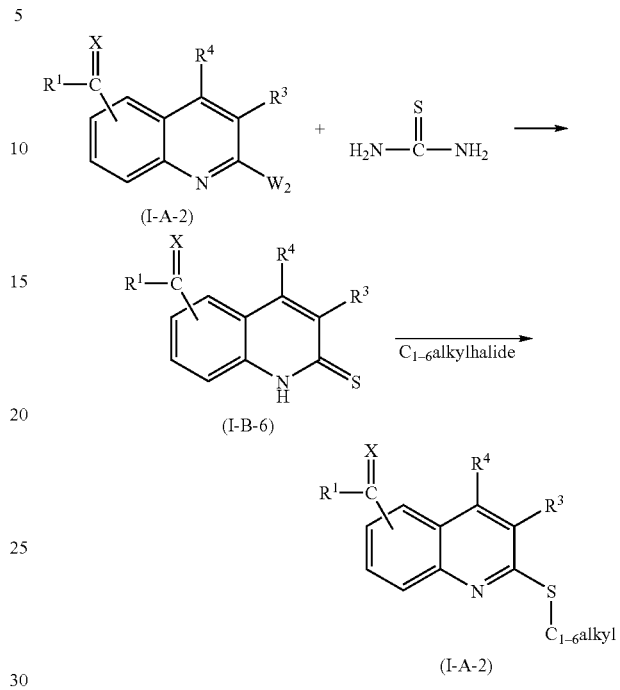

Compounds of formula ($I_{A/B}$-a) can be converted into a compounds of formula (I-A) or (I-B), wherein X is N—$R^7$, said compound being represented by formula ($I_{A/B}$-b), by reaction with an intermediate of formula (XVI), optionally in the presence of a suitable base, such as for example N,N-diethylethanamine, and in the presence of a suitable reaction-inert solvent, such as an alcohol, e.g. ethanol.

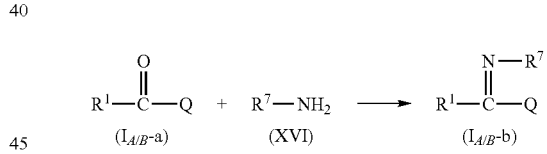

As already indicated in the preparation procedure of compounds of formula (I-A-13) described above, the compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, allylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Some of the intermediates and starting materials used in the above reaction procedures are commercially available, or may be synthesized according to procedures already described in the literature.

Intermediates of formula (II) may be prepared by reacting an intermediate of formula (XVII) with an intermediate of formula (XVIII), wherein $W_5$ represents a suitable leaving group such as a halo atom, e.g. chloro, bromo and the like, in the presence of magnesium, diethylether and a suitable reaction-inert solvent, such as diethylether.

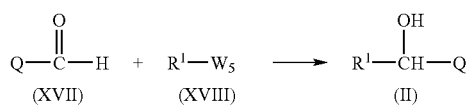

Intermediates of formula (XVII) may be prepared by oxidizing an intermediate of formula (XIX) in the presence of a suitable oxidizing agent, such as $MnO_2$, and a suitable reaction-inert solvent, such as methylene chloride.

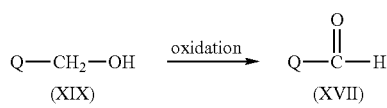

Intermediates of formula (XIX) can be prepared by reducing an intermediate of formula (XX) in the presence of a suitable reducing agent such as lithium aluminium hydride, and a suitable reaction-inert solvent, such as tetrahydrofuran.

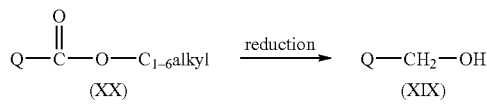

Intermediates of formula (XX), wherein Q represents a quinoline moiety optionally substituted in position 3 with $C_{1-6}$alkyl and wherein the carbonyl moiety is placed in position 6, said intermediates being represented by formula (XX-a), can be prepared by reacting an intermediate of formula (XXI) with an intermediate of formula (XXII) in the presence of sodium 3-nitro-benzene sulfonate, a suitable acid, such as sulfuric acid, and a suitable alcohol, e.g. methanol, ethanol, propanol, butanol and the like.

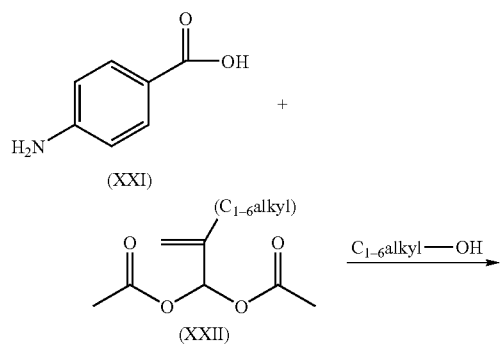

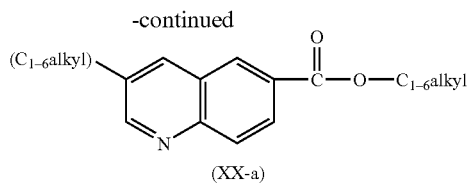

Alternatively, intermediates of formula (II) can also be prepared by reacting an intermediate of formula (XXIII) with an intermediate of formula (XXIV), wherein $W_6$ is a suitable leaving group, such as a halo atom, e.g. bromo, chloro and the like, in the presence of a suitable agent, such as butyl lithium and a suitable reaction-inert solvent, such as tetrahydrofuran.

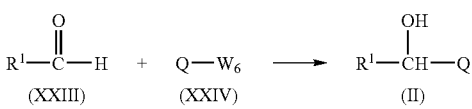

Intermediates of formula (XXIII) can be prepared by oxidizing an intermediate of formula (XXV) using the Moffatt Pfitzner or Swern oxidation (dimethylsulfoxide adducts with dehydrating agents e.g. DCC, $Ac_2O$, $SO_3$, $P_4O_{10}$, $COCl_2$ or Cl—CO—COCl) in an inert solvent such as methylene chloride.

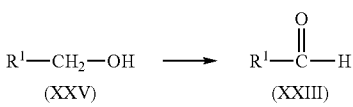

Intermediates of formula (XXV) can be prepared by reducing an intermediate of formula (XXVI) in the presence of a suitable reducing agent, such as for example lithium aluminium hydride and a suitable reaction-inert solvent, such as benzene.

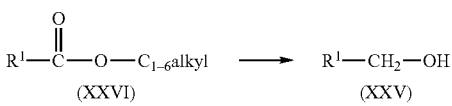

Intermediates of formula (XXVI) can be prepared from an intermediate of formula (XXVII) by esterification in the presence of a suitable alcohol, such as methanol, ethanol, propanol, butanol and he like, and a suitable acid, such as sulfuric acid.

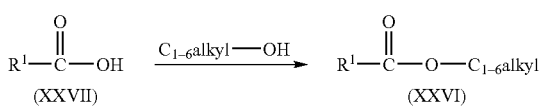

Intermediates of formula (XXVII), wherein $R^1$ represents a radical of formula (a-1) with $Z_1$ being O, $Z_2$ being $CH_2$ and n being 1, said intermediates being represented by formula (XXVII-a), can be prepared by reducing an intermediate of formula (XXVIII) in the presence of a suitable reducing agent such as hydrogen, and a suitable catalyst, such as palladium on charcoal, and a suitable acid such as acetic acid. When $R^1$ of intermediate (XXVII) represents an optionally substituted phenyl moiety, it can also be converted into an optionally substituted cyclohexyl moiety by reduction in the presence of a suitable reducing agent such as rhodium on $Al_2O_3$, and a suitable reaction-inert solvent, such as tetrahydrofuran.

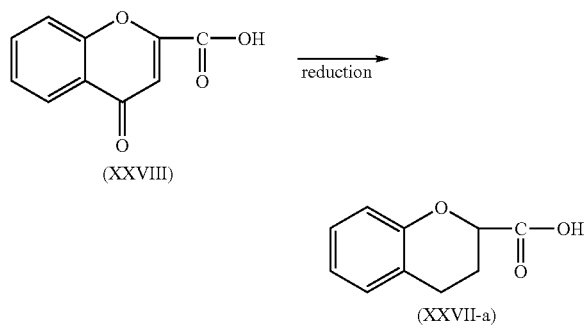

Intermediates of formula (IV), wherein Q represents a quinoline moiety substituted in position 2 with halo, e.g. chloro, said intermediates being represented by formula (IV-a), can be prepared by reacting an intermediate of formula (IV), wherein Q represents a quinolinone moiety with $R^5$ being hydrogen, said intermediate being represented by formula (IV-b), in the presence of $POCl_3$.

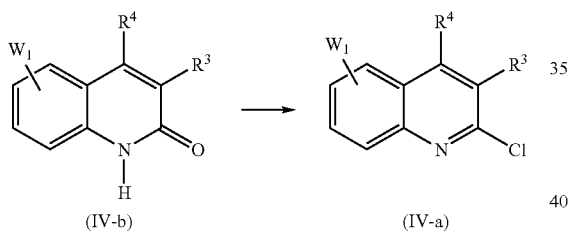

Intermediates of formula (IV-a), wherein $R^4$ is hydrogen, said intermediates being represented by formula (IV-a-1), can also be prepared by reacting an intermediate of formula (XXIX) with $POCl_3$ in the presence of N,N-diethylformamide (Vilsmeier-Haack formylation followed by cyclization).

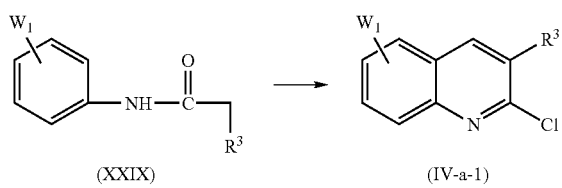

Intermediates of formula (XXIX) may be prepared by reacting an intermediate of formula (XXX) with an intermediate of formula (XXXI), wherein $W_7$ represents a suitable leaving group, such as a halo atom, e.g. chloro, in the presence of a suitable base, such as for example N,N-diethylethanamine, and a suitable reaction-inert solvent, such as methylene chloride.

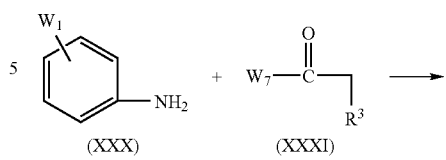

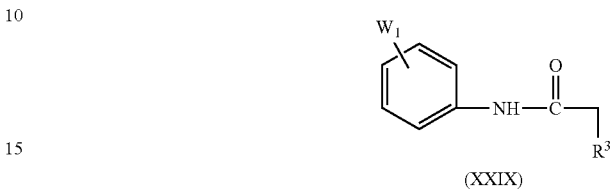

Intermediates of formula (IV-a) can be converted into an intermediate of formula (IV-c) by reaction with an intermediate of formula (XXXII) in the presence of a suitable reaction-inert solvent, such as an alcohol, e.g. methanol and the like.

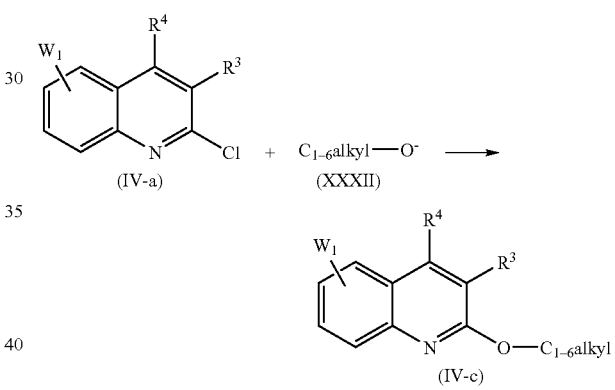

Intermediates of formula (IV-a) can also be converted into an intermediate of formula (IV-d-1) by reaction with a suitable amine of formula (XXXIII-a), wherein $Z_3$ and $Z_4$ each independently represent hydrogen, $C_{1-6}$alkyl, $C_{1-6}$alkyloxy$C_{1-6}$alkyl, $C_{1-6}$alkylthio$C_{1-6}$alkyl or into an intermediate of formula (IV-d-2) by reaction with a suitable amine of formula (XXXIII-b), wherein $Z_3$ and $Z_4$ are taken together to form a heterocycle as defined hereinabove in the definition of $R^2$ provided that the heterocycle comprises at least one nitrogen atom, in the presence of a suitable base, such as for example dipotassium carbonate, and a reaction-inert solvent, such as N,N-dimethylformamide.

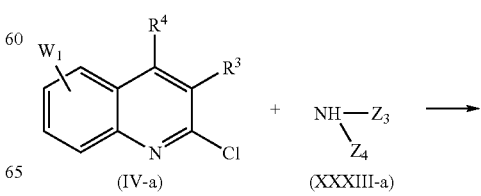

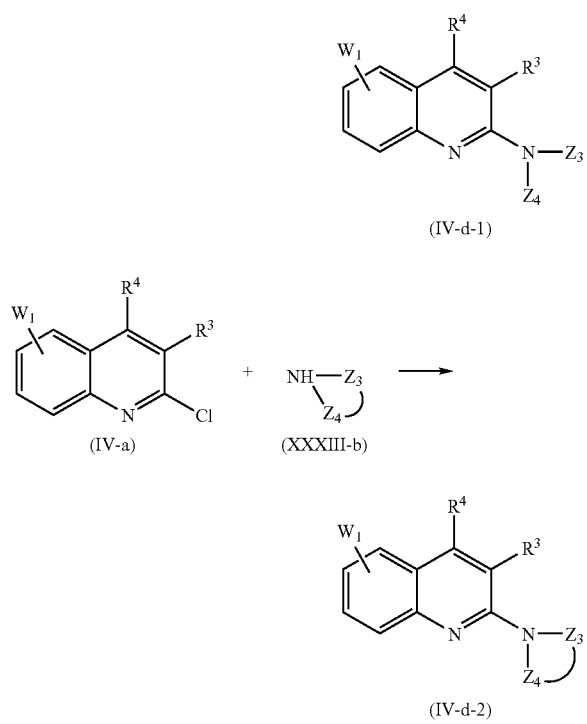

(IV-d-1)

(IV-a) (XXXIII-b)

(IV-d-2)

Intermediates of formula (IV-a), wherein $R^3$ represents $CH_2—CH_2—CH_2—Cl$, said intermediates being represented by formula (IV-a-2), can also be converted into an intermediate of formula (IV), wherein $R^2$ and $R^3$ are taken together to form a bivalent radical of formula $—O—CH_2—CH_2—CH_2—$, said intermediate being represented by formula (IV-e-1), by reaction with a suitable acid, such as hydrochloric acid and the like. Intermediates of formula (IV-a-2) can also be converted into an intermediate of formula (IV), wherein $R^2$ and $R^3$ are taken together to form a bivalent radical of formula $—S—CH_2—CH_2—CH_2—$, said intermediate being represented by formula (IV-e-2), by reaction with $H_2N—C(=S)—NH_2$ in the presence of a suitable reaction-inert solvent, such as an alcohol, e.g. ethanol.

Intermediates of formula (V) may be prepared by reacting an intermediate of formula (XXVII) with an intermediate of formula $CH_3—NH—O—CH_3$ in the presence of 1,1'-carbonyldiimidazole and a suitable reaction-inert solvent, such as methylene chloride.

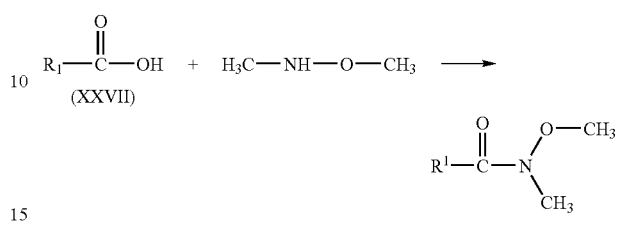

(XXVII)

(V)

Intermediates of formula (VII), wherein Q represents a quinoline moiety, in particular a quinoline moiety wherein $R^2$ is ethyl, $R^3$ is methyl and $R^4$ is hydrogen, and the carboxyl moiety is placed in position 6, said intermediates being represented by formula (VII-a), can be prepared by reaction an intermediate of formula (XXXIV) in the presence of a suitable aldehyde, such as $CH_3—CH_2—CH(=O)$, $(CH_2O)_n$, $ZnCl_2$, $FeCl_3$ and a suitable reaction-inert solvent, such as an alcohol, for example ethanol.

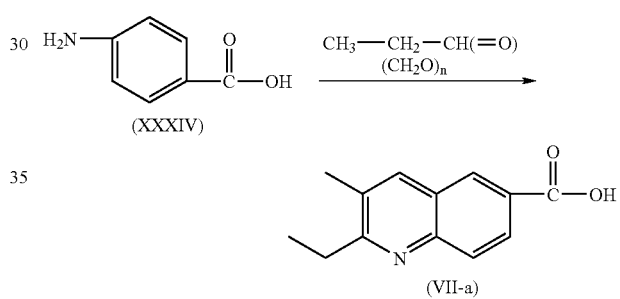

(XXXIV)

(VII-a)

Intermediates of formula (VIII) can be prepared by reacting an intermediate of formula (XXXV) with an intermediate of formula (XXXVI) in the presence of a suitable catalyst, such as for example tetrakis(triphenylphosphine)palladium and a suitable reaction-inert solvent, such as for example dioxane.

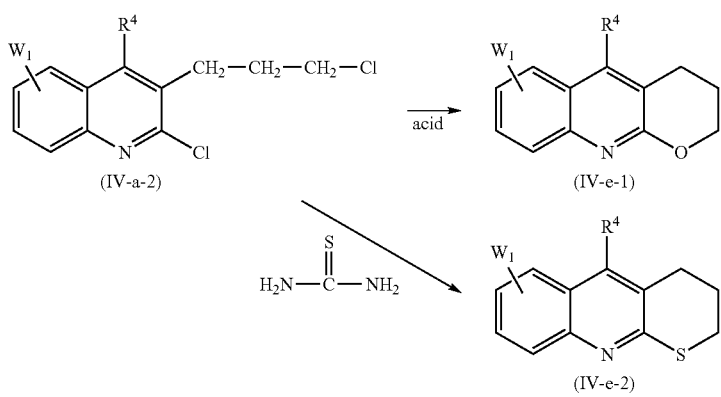

(IV-a-2) (IV-e-1)

(IV-e-2)

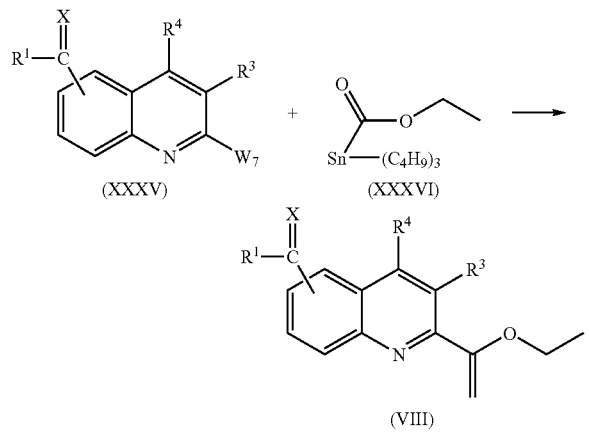

Still some other preparations can be devised, some of them are disclosed further in this application with the Examples.

Pure stereoisomeric forms of the compounds and the intermediates of this invention may be obtained by the application of art-known procedures. Diastereomers may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromato-graphic techniques using chiral stationary phases. Said pure stereoisomeric forms may also be derived from the corresponding pure stereoisomeric forms of the appropriate starting materials, provided that the reaction occurs stereo-selectively or stereospecifically. Preferably, if a specific stereoisomer is desired, said compound will be synthesized by stereoselective or stereospecific methods of preparation. These methods will advantageously employ chirally pure starting materials. Stereoisomeric forms of the compounds of formula (I) are obviously intended to be included within the scope of the invention.

A stereoisomer of a compound of formula (I-A) or (I-B) such as a cis form, may be converted into another stereoisomer such as the corresponding trans form by reacting the compound with a suitable acid, such as hydrochloric acid, in the presence of a suitable reaction-inert solvent, such as for example tetrahydrofuran.

The compounds of formula (I-A) and (I-B), the N-oxides, the pharmaceutically acceptable addition salts, the quaternary amines and the stereochemically isomeric forms thereof show mGluR antagonistic activity, more in particular Group I mGluR antagonistic activity. The Group I mGluR specifically antagonized by the present compounds is the mGluR1.

The mGluR1 antagonistic activity of the present compounds can be demonstrated in the Signal transduction on cloned rat mGluR1 in CHO cells test and the Cold allodynia test in rats with a Bennett ligation, as described hereinafter.

Due to their mGluR antagonistic activity, more in particular their Group I mGluR antagonistic activity and even more in particular, their mGluR1 antagonistic activity, the compounds of formula (I-A) or (I-B), their N-oxides, pharmaceutically acceptable addition salts, quaternary amines and stereochemically isomeric forms are useful in the treatment or prevention of glutamate-induced diseases of the central nervous system. Diseases in which a role for glutamate has been demonstrated include drug addiction or abstinence (dependence, opioid tolerance, opioid withdrawal), hypoxic, anoxic and ischemic injuries (ischemic stroke, cardiac arrest), pain (neuropathic pain, inflammatory pain, hyperalgesia), hypoglycemia, diseases related to neuronal damage, brain trauma, head trauma, spinal cord injury, myelopathy, dementia, anxiety, schizophrenia, depression, impaired cognition, amnesia, bipolar disorders, conduct disorders, Alzheimer's disease, vascular dementia, mixed (Alzheimer's and vascular) dementia, Lewy Body disease, delirium or confusion, Parkinson's disease, Huntington's disease, Down syndrome, epilepsy, aging, Amyotrophic Lateral Sclerosis, multiple sclerosis, AIDS (Acquired Immune Deficiency Syndrome) and AIDS related complex (ARC).

In view of the utility of the compounds of formula (I-A) and (I-B), there is provided a method of treating warm-blooded animals, including humans, suffering from glutamate-induced diseases of the central nervous system. Said method comprises the administration, preferably oral administration, of an effective amount of a compound of formula (I-A) or (I-B), a N-oxide form, a pharmaceutically acceptable addition salt, a quaternary amine or a possible stereoisomeric form thereof, to warm-blooded animals, including humans.

In view of the above described pharmacological properties, the compounds of formula (I-A) and (I-B) or any subgroup thereof, their N-oxides, pharmaceutically acceptable addition salts, quaternary amines and stereochemically isomeric forms, may be used as a medicine. In particular, the use of a compound of formula (I-A) and (I-B) in the manufacture of a medicament for treating or preventing glutamate-induced diseases of the central nervous system is provided. More in particular, the present compounds may be used as neuroprotectants, analgesics or anticonvulsants.

The present invention also provides compositions for treating or preventing glutamate-induced diseases of the central nervous system comprising a therapeutically effective amount of a compound of formula (I-A) or (I-B) and a pharmaceutically acceptable carrier or diluent.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, a therapeutically effective amount of a particular compound, in base or addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, topically, percutaneously or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, emulsions, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. As appropriate compositions for topical application there may be cited all compositions usually employed for topically administering drugs e.g. creams, gel, dressings, shampoos, tinctures, pastes, ointments, salves, powders and the like. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used in the specification and claims herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions, teaspoonfuls, tablespoonfuls and the like, and segregated multiples thereof.

The therapeutically effective dose or frequency of administration depends on the particular compound of formula (I-A) or (I-B) used, the particular condition being treated, the severity of the condition being treated the age, weight, sex, fed or fasted state, and the general physical condition of the particular patient as well as other medication the individual may be taking, as is well known to those skilled in the art. Furthermore, it is evident that said therapeutically effective dose or the effective daily dose may be lowered or increased depending on the response of the treated subject and/or depending on the evaluation of the physician prescribing the compounds of the instant invention. It may be appropriate to administer the required dose as two, three, four or more sub-doses at appropriate intervals throughout the day. Said sub-doses may be formulated as unit dosage forms.

The following examples are intended to illustrate the present invention.

EXPERIMENTAL PART

Hereinafter, "DMF" is defined as N,N-dimethylformamide, "DIPE" is defined as diisopropylether, "DMSO" is defined as dimethylsulfoxide, "BHT" is defined as 2,6-bis(1,1-dimethylethyl)-4-methylphenol, and "THF" is defined as tetrahydrofuran.

Preparation of the Intermediates

EXAMPLE A1

Preparation of

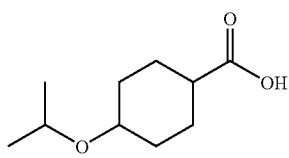

(interm. 1)

A mixture of 4-(1-methylethoxy)benzoic acid (0.083 mol) and Rh/Al$_2$O$_3$ 5% (10 g) in THF (220 ml) was hydrogenated at 50° C. (under 3 bar pressure of H$_2$) for 1 night. The mixture was filtered over celite, washed with THF and evaporated. Yield: 16 g of intermediate 1 (100%).

EXAMPLE A2

Preparation of 2-ethyl-3-methyl-6-quinolinecarboxylic acid (interm. 2)

A mixture of 4-aminobenzoic acid (0.299 mol) in ethanol (250 ml) was stirred at room temperature. ZnCl$_2$ (0.0367 mol) and (CH$_2$O)$_n$ (10 g) were added. FeCl$_3$.6H$_2$O (0.5 mol) was added portionwise and the temperature rised till 60-65° C. Propanal (30 ml) was added dropwise over a 2 hours period. The mixture was refluxed for 2 hours and kept at room temperature for 12 hours. The mixture was poured into water and filtered through celite. The filtrate was acidified till pH=7 with HCl 6N and the mixture was evaporated till dryness. The residue was used without further purification. Yield: 56.1 g of 2-ethyl-3-methyl-6-quinolinecarboxylic acid (interm. 2).

EXAMPLE A3

Preparation of

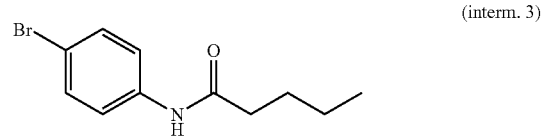

(interm. 3)

Pentanoyl chloride (0.2784 mol) was added at 5° C. to a mixture of 4-bromobenzenamine (0.232 mol) and N,N-ethylethanamine (0.2784 mol) in CH$_2$Cl$_2$ (400 ml). The mixture was stirred at room temperature overnight, poured out into water and extracted with CH$_2$Cl$_2$. The organic layer was separated, washed with a concentrated NH$_4$OH solution and water, dried (MgSO$_4$), filtered and the solvent was evaporated. The residue (60 g) was crystallized from diethylether. The precipitate was filtered off and dried. The residue (35 g, 63%) was taken up in CH$_2$Cl$_2$. The organic layer was separated, washed with a 10% K$_2$CO$_3$ solution, washed with water, dried (MgSO$_4$), filtered and the solvent was evaporate Yield: 30 g of intermediate (3) (54%).

EXAMPLE A4

Preparation of

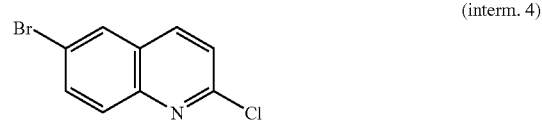

(interm. 4)

A mixture of 6-bromo-2(1H)-quinolinone (0.089 mol) in POCl$_3$ (55 ml) was stirred at 60° C. overnight, then at 100° C. for 3 hours and the solvent was evaporated. The residue was taken up in CH$_2$Cl$_2$, poured out into ice water, basified with NH$_4$OH conc., filtered over celite and extracted with CH$_2$Cl$_2$. The organic layer was separated, dried (MgSO$_4$), filtered and the solvent was evaporated. Yield. 14.5 g of intermediate (4) (67%).

EXAMPLE A5 a) Preparation of

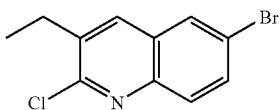
(interm. 5)

DMF (37 ml) was added dropwise at 10° C. under N₂ flow to POCl₃ (108 ml). After complete addition, the mixture was allowed to warm to room temperature. N-(4-bromophenyl)butanamide (0.33 mol) was added portionwise. The mixture was stirred at 85° C. overnight, then allowed to cool to room temperature and poured out on ice (exothermic reaction). The precipitate was filtered off, washed with a small amount of water and dried (vacuum). The residue was washed with EtOAc/diethyl ether and dried. Yield: 44.2 g of intermediate (5) (50%).

b) Preparation of

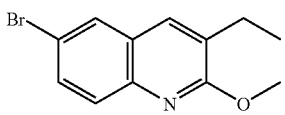
(interm. 6)

A mixture of intermediate (5) (0.162 mol) in methanol (600 ml), and a solution of methanol sodium salt in methanol at 35% (154 ml) was stirred and refluxed overnight. The mixture was poured out on ice. The precipitate was filtered off, washed with a small amount of water and taken up in CH₂Cl₂, K₂CO₃ 10% was added and the mixture was extracted with CH₂Cl₂. The organic layer was separated, washed with water, dried (MgSO₄), filtered and the solvent was evaporated. Yield: 31.9 g of intermediate (6) (74%).

EXAMPLE A6

Preparation of

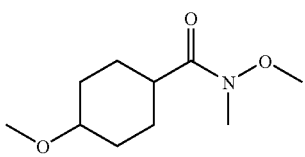
(interm. 7)

1,1'-Carbonylbis-1H-imidazole (0.074 mol) was added portionwise to a mixture of 4-methoxycyclohexanecarboxylic acid (0.063 mol) in CH₂Cl₂ (200 ml). The mixture was stirred at room temperature for 1 hour. Then N-methoxymethanamine (0.074 mol) was added. The mixture was stirred at room temperature overnight, poured out into H₂O and extracted with CH₂Cl₂. The organic layer was separated, washed several times with H₂O, drized (MgSO₄), filtered and the solvent was evaporated. Yield: 12.6 g of interm. 7.

EXAMPLE A7 a) A mixture of 6-fluoro-4-oxo-4H-1-benzopyran-2-carboxylic acid (0.30 mol) in acetic acid (400 ml) was hydrogenated with Pd/C (3 g) as a catalyst. After uptake of H₂ (3 equiv), the catalyst was filtered off. The filtrate was evaporated. The residue was stirred in petroleum ether. The precipitate was filtered off and dried (vacuum; 70° C.). After recrystallization from CHCl₃/CH₃OH, the precipitate was filtered off and dried (vacuum; 80° C. and high vacuum; 85° C.). Yield: 8.8 g of 6-fluoro-3,4-dihydro-2H-1-benzopyran-2-carboxylic acid (interm. 8) (15.0%).

b) A mixture of intermediate (8) (0.255 mol) in ethanol (400 ml) and H₂SO₄ (5 ml) was stirred and refluxed for 8 hours. The solvent was evaporated till dryness. The residue was dissolved in CH₂Cl₂. The organic layer was separated, washed with K₂CO₃ 10%, dried (MgSO₄), filtered and the solvent was evaporated. Yield: 45 g of ethyl 6-fluoro-3,4-dihydro-2H-1-benzopyran-2-carboxylate (interm. 9) (79%).

c) Reaction under N₂. A mixture of sodium bis(2-methoxyethoxy)aluminumhydride, 70 wt % solution in methylbenzene 3.4 M (0.44 mol) in benzene (150 ml) (reflux) was added dropwise during 1 hour to a refluxed mixture of interm. 9 (0.22 mol) and benzene (600 ml). After stirring for 2.5 hours at reflux temperature, the mixture was cooled to ±15° C. The mixture was decomposed by adding dropwise ethanol (30 ml) and water (10 ml). This mixture was poured out onto ice/water and this mixture was acidified with concentrated hydrochloric acid. This mixture was extracted with diethyl ether (500 ml). The separated organic layer was washed with water, dried, filtered and the solvent was evaporated. The residue was purified by column chromotoghaphy over silica gel (eluent: CHCl₃). The desired fraction was collected and the eluent was evaporated. Yield. 34 g of 6-fluoro-3,4-dihydro-2H-1-benzopyran-2-methanol (interm. 10) (85%).

d) Reaction under N₂. To a stirred and cooled (−60° C.; 2-propanone/CO₂ bath) mixture of ethanedioyl dichloride (0.1 mol) in CH₂Cl₂ (350 ml) was added sulfinylbis[methane] (30 ml) during 10 minutes. After stirring 10 minutes, a mixture of interm. 10 in CH₂Cl₂ (90 ml) was added during 5 minutes. After stirring for 15 minutes, N,N-diethylethanamine (125 ml) was added. When the mixture was warmed up to room temperature, it was poured out in water. The product was extracted with CH₂Cl₂. The organic layer was washed with water, HCl (1 M), water, NaHCO₃ (10%) and water, dried and evaporated. The residue was dissolved in diethyl ether, washed with water, dried, filtered and evaporated. The residue was purified by column chromotoghaphy over silica gel (eluent: CHCl₃). The desired fraction was collected and the eluent was evaporated. Yield: 21.6 g of 6-fluoro-3,4-dihydro-2H-1-benzopyran-2-carboxaldehyde (interm. 11)

e) Preparation of

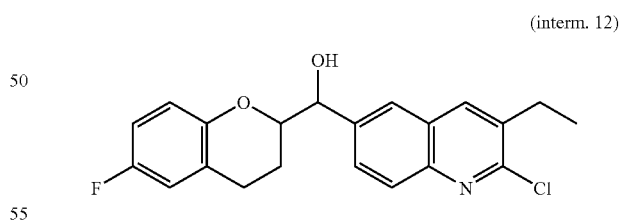
(interm. 12)

nButyllithium 1.6 M (0.056 mol) was added slowly at −70° C. to a solution of intermediate (5) (0.046 mol) in THF (100 ml). The mixture was stirred at −70° C. for 30 minutes. A suspension of interm. 11 (0.056 mol) in THF (100 ml) was added slowly. The mixture was stirred at −70° C. for 1 hour, then brought to room temperature, poured out into H₂O and extracted with EtOAc. The organic layer was separated, dried (MgSO₄), filtered and the solvent was evaporated. The residue (21 g) was purified by column chromatography over silica gel (eluent: cyclohexane/EtOAc 80/10; 15-35 μm). The pure fractions were collected and the solvent was evaporated. Yield: 9.5 g of interm. 12 (55%).

EXAMPLE A8 a) Preparation of

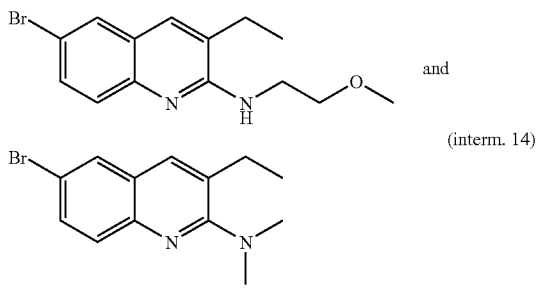

A mixture of intermediate (5) (0.1127 mol), 2-methoxy-ethanamine (0.2254 mol) and K$_2$CO$_3$ (0.2254 mol) in DMF (500 ml) was stirred at 120° C. for 15 hours and then cooled. The solvent was evaporated. The residue was taken up in CH$_2$Cl$_2$ and H2O. The organic layer was separated, dried (MgSO$_4$), filtered and the solvent was evaporated till dryness. The residue (33.53 g) was purified by column chromatography over silica gel (eluent: CH$_2$Cl$_2$/CH$_3$OH 99.5/0.5; 15-40 µm). Two fractions were collected and their solvents were evaporated. Yield: 5.7 g of interm. 14 (38%) and interm. 13 (34%).

b) Preparation of

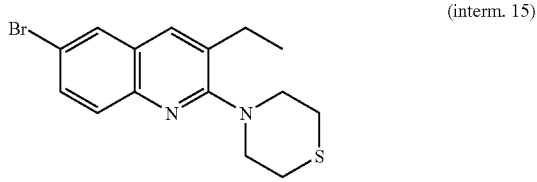

A mixture of intermediate (5) (0.0751 mol), thiomorpholine (0.0891 mol) and K$_2$CO$_3$ (0.15 mol) in DMF (200 ml) was stirred at 120° C. for 12 hours. The solvent was evaporated till dryness. The residue was taken up in CH$_2$Cl$_2$ and H$_2$O. The organic layer was separated, dried (MgSO$_4$), filtered and the solvent was evaporated. The residue (26 g) was purified by column chromatography over silica gel (eluent: cyclohexane/EtOAc 80/20; 20-45 µm). Two factions were collected and their solvents were evaporated. The two fractions were combined. Yield: 9.4 g of interm. 15 (37%); mp. 82° C.

EXAMPLE A9 a) 4-Aminobenzoic acid (0.219 mol) was added to a solution of sodium 3-nitrobenzenesulfonate (0.118 mol) in H$_2$SO$_4$ 70% (230 ml) and the mixture was stirred and refluxed. 2-propene-1,1-diol, 2-methyl-, diacetate (0.216 mol) was added dropwise and the mixture was refluxed for 4 hours. Ethanol (200 ml) was added and the mixture was stirred at 80° C. for 48 hours. The mixture was evaporated, the residue was poured into ice water/NH$_4$OH and extracted with CH$_2$Cl$_2$. The organic layer was dried (MgSO$_4$) and evaporated. The residue was purified by column chromatography over silica gel (eluent: CH$_2$Cl$_2$/2-propanol 99/1). The pure fractions were collected and evaporated. Yield: 21 g of ethyl 3-methyl-6-quinolinecarboxylate (interm. 16) (45%).

b) Interm. 16 (0.098 mol) in THF (270 ml) was added at 0° C. to a solution of LiAlH$_4$ (0.098 mol) in THF under N$_2$. When the addition was complete, water (10 ml) was added. The precipitate was filtered off and washed with CH$_2$Cl$_2$. The organic layer was dried (MgSO$_4$), filtered off and evaporated. The product was used without further purification. Yield: 16.71 g of 3-methyl-6-quinolinemethanol (interm. 17).

c) MnO$_2$ (0.237 mol) was added to a solution of interm. 17 (0.096 mol) in CH$_2$Cl$_2$ (200 ml) and the mixture was stirred at room temperature for 12 hours. The mixture was filtered through celite and the filtrate was stirred again with MnO$_2$ (20 g) for 12 hours. MnO$_2$ (10 g) was added again. The mixture was stirred for 12 hours. The mixture was filtered through celite and evaporated. The product was used without further purification. Yield: 11.71 g of 3-methyl-6-quinolinecarboxaldehyde (71%) (interm. 18).

d) A solution of bromocyclohexyl (0.14 mol) in 1,1'-oxybisethane (50 ml) and Mg turnings (50 ml) was added at 10° C. to a mixture of THF (0.14 mol) in 1,1'-oxybisethane (10 ml). A solution of interm. 18 (0.07 mol) in Mg turnings (100 ml) was added carefully at 5° C., the mixture was poured into ice water and extracted with EtOAc. Yield: 11.34 g of (±)-α-cyclohexyl-3-methyl-6-quinolinemethanol (63%) (interm. 19).

EXAMPLE A10

Preparation of

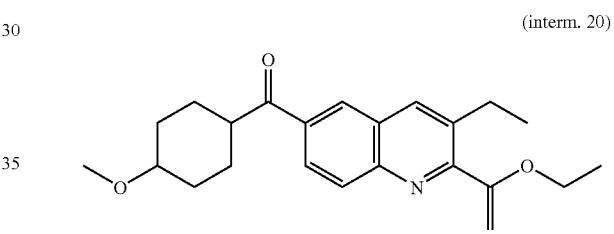

A mixture of compound (5) (0.001507 mol), tributyl(1-ethoxyethenyl)stannane (0.00226 mol) and Pd(PPh$_3$)$_4$ (0.000151 mol) in 1,4-dioxane (5 ml) was stirred at 80° C. for 3 hours. Water was added. The mixture was extracted with EtOAc. The organic layer was separated, dried (MgSO$_4$), filtered and the solvent was evaporated. This product was used without further purification. Yield: 1.4 g of interm. 20.

EXAMPLE A11

Preparation of

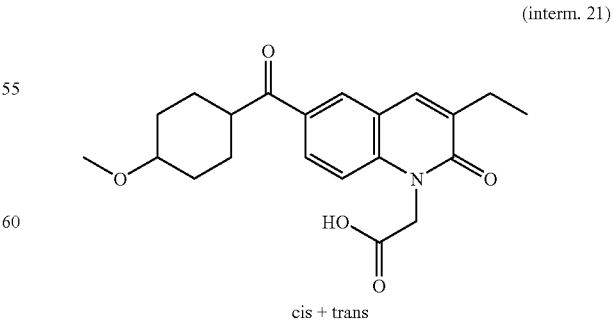

cis + trans

A mixture of compound (45) (prepared according to B6) (0.00125 mol) in NaOH 3N (5 ml) and iPrOH (1.7 ml) was stirred at room temperature overnight, then poured out into H₂O, acidified with HCl 3N and extracted with EtOAc. The organic layer was separated, dried (MgSO₄), filtered and the solvent was evaporated. The residue was taken up in diethyl ether. The precipitate was filtered off and dried. Yielding: 0.26 g of intermediate 23 (56%). (mp.: 232° C.)

EXAMPLE A12 a. Preparation of

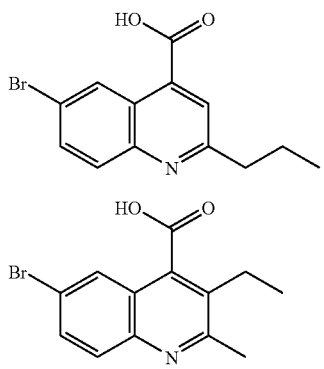

(interm. 22)

(interm. 23)

A mixture of 5-bromo-1H-indole-2,3-dione (0.221 mol) in NaOH 3N (500 ml0 was stirred at 80° C. for 30 minutes, brought to room temperature and 2-pentanone (0.221 mol) was added. The mixture was stir and refluxed for 1 hour and 30 minutes and acidified with AcOH until pH=5. The precipitate was filtered, washed with water and dried. Yielding 52.3 g of intermediate 24 and intermediate 25. (Total yielding: 80%).

b. Preparation of

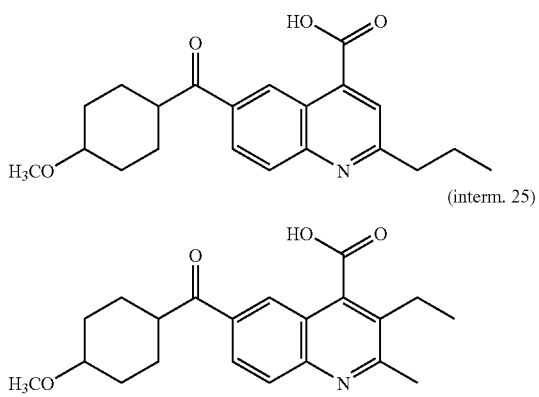

(interm. 24)

(interm. 25)

nBuLi 1.6 M (0.0816 mol) was added dropwise at −78° C. to a suspension of intermediate 25 (0.034 mol) and intermediate 26 (0.034 mol) in THF (300 ml) under N₂ flow. The mixture was stirred at −78° C. for 30 minutes. nBuLi 1.6 M (0.0816 mol) was added dropwise. The mixture was stirred for 1 hour. A mixture of intermediate 9 (0.102 mol) in THF (250 ml) was added slowly. The mixture was stirred for −78° C. to −20° C., poured out into H₂O/HCl 3N and extracted with EtOAc. The organic layer was separated, dried (MgSO₄), filtered, and the solvent was evaporated till dryness. Yielding: 20.89 g of compound intermediate 26 and intermediate 27 (86%).

EXAMPLE A13 a. Preparation of

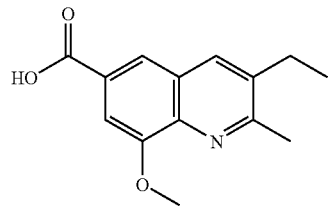

(interm. 26)

4-amino-3-methoxybenzoic acid (0.054 mol) was added portionwise at room temperature to a solution of 3-chloro-2-ethyl-2-butenal (0.065 mol) in AcOH (100 ml). The mixture was stirred and refluxed for 8 hours and evaporated to dryness. The residue was taken up in CH₂Cl₂, water was added and the solution was basified by Et₃N. The organic layer was separated, dried (MgSO₄), filtered, and the solvent was evaporated. The residue was crystallized from 2-propanone. The precipitate was filtered off and dried. Yielding: 2.5 g of interm. 26 (18%).

b. Preparation of

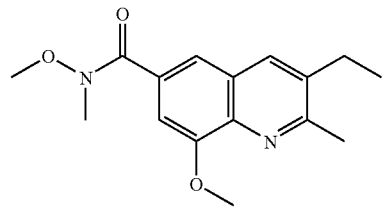

(interm. 27)

CDI (0.012 mol) was added at room temperature to a solution of interm. 26 (0.011 mol) in CH₂Cl₂ (30 ml). The mixture was sired at room temperature for 1 hour. methoxyaminomethyl (0.012 mol) was added and the mixture was stirred at room temperature for 8 hours. H₂O was added. A precipitate was filtered off. The filtrate was extracted with CH₂Cl₂. The organic layer was separated, dried (MgSO₄), filtered, and the solvent was evaporated. The residue was crystallized from diethyl ether. The precipitate was filtered off and dried. Yielding: 0.95 g of interm. 27 (31%) (mp.:148° C.).

EXAMPLE A14

Preparation of

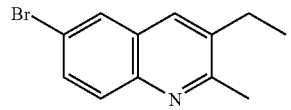

(interm. 28)

4-Bromobenzenamine (0.034 mol) was added at room temperature to a solution of 3-chloride-2-ethyl-2-butanal (0.041 mol) in AcOH (60 ml). The mixture was stirred and refluxed for 8 hours, brought to room temperature and evaporated to dryness. The product was crystallized from EtOAc. The precipitate was filtered, washed with K2CO3 10% and taken up in CH2Cl2. The organic layer was separated, dried (MgSO4), filtered, and the solvent was evaporated. Yielding: 4.6 g of interm. 28 (54%).

EXAMPLE A15 a. Preparation of

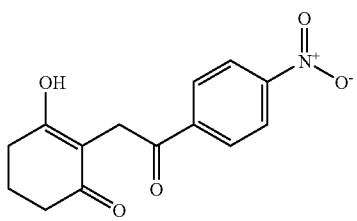 (interm. 29)

A solution of KOH (0.326 mol) in H₂O (150 ml) was added slowly at 5° C. to a solution of 1,3-cyclohexanedione (0.268 mol) in H₂O (150 ml). The temperature must not reach 12° C. KI (2 g) then 2-bromo-1-(4-nitrophenyl)ethanone (0.294 mol) were added portionwise. The mixture was stirred at room temperature for 48 hours. The precipitate was filtered, washed with H₂O then with diethyl ether and dried. Yielding: 63 g (85%). A part of this fraction (1 g) was crystallized from EtOH. The precipitate was filtered off and dried. Yielding: 0.5 g of interm. 29 (42%) (mp.: 100° C.).

b. Preparation of

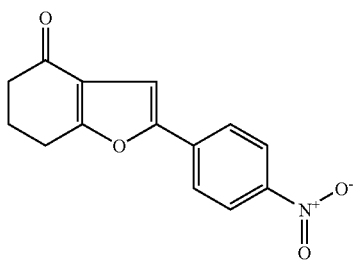 (interm. 30)

A mixture of interm. 29 (0.145 mol) in H₂SO₄ (40 ml) was stirred at room temperature for 1 hour, poured out into ice, basified with NH₄OH and extracted with CH₂Cl₂. The organic layer was separated, dried (MgSO₄), filtered, and the solvent was evaporated. The residue was crystallized from EtOH. The precipitate was filtered off and dried. Yielding: 31 g (58%). A part of this fraction (1 g) was crystallized from EtOH. The precipitate was filtered off and dried. Yielding: 0.7 g of interm. 30 (58%) (mp.:200° C.).

c. Preparation of

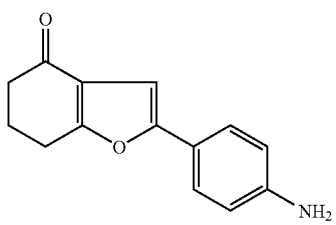 (interm. 31)

A mixture of interm. 30 (0.039 mol), Raney Ni (10 g) in EtOH (100 ml) was hydrogenated at room temperature under a 3 bar pressure for 1 hour. The mixture was filtered over celite and washed with CH₂Cl₂. The organic layer was separated, dried (MgSO₄), filtered, and the solvent was evaporated. The residue (9.5 g) was crystallized from diethyl ether. The precipitate was filtered off and dried. Yielding: 4.6 g (52%). The filtrate was evaporated. The residue (2.7 g) was purified by column chromatography over silica gel (eluent: CH₂Cl₂/CH₃OH; 99/1; 15-40 μm). Two fractions were collected and the solvent was evaporated. Yielding: 1.6 g F1 and 1.2 g F2. F2 was crystallized from EtOH. The precipitate was filtered off and dried. Yielding: 0.24 g of interm. 31 (2%) (mp.:202° C.).

d. Preparation of

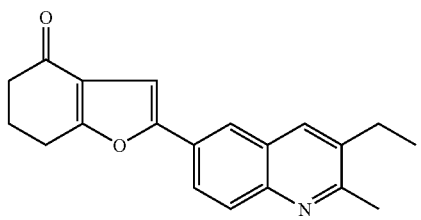 (interm. 32)

Interm. 30 (0.02 mol) was added at room temperature to a solution of 3-chloro-2-ethyl-2-butenal (0.04 mol) in AcOH (50 ml). The mixture was stirred and refluxed for 4 hours. The solvent was evaporated till dryness. The residue was crystallized from EtOAc. The precipitate was filtered off and dried. The residue was taken up in CH₂Cl₂. The mixture was basified with K₂CO₃ 10% and extracted with CH₂Cl₂. The organic layer was separated, dried (MgSO₄), filtered, and the solvent was evaporated. The residue was crystallized from EtOH. The precipitate was filtered off and dried. Yielding: 2.5 g of interm. 32 (40%).

EXAMPLE A16

Preparation of

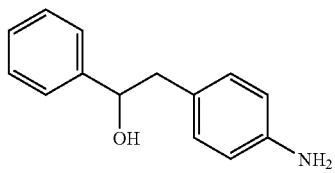 (interm. 33)

A mixture of 2-(4-nitrophenyl)-1-phenylethanone (0.083 mol) and Raney Ni (20 g) in EtOH (200 ml) was hydrogenated at room temperature for 1 hour under a 3 bar pressure, then filtered over celite, washed with CH₂Cl₂/CH₃OH and dried. Yielding: 17.5 g of interm. 33 (97%).

B. Preparation of the Final Compounds

EXAMPLE B1

Preparation of

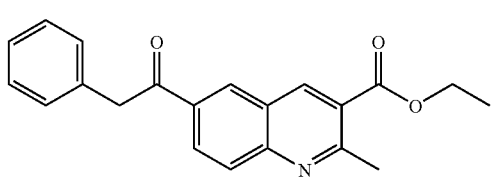 (compound 306)

POCl₃ (0.024 mol) was added slowly at 5° C. to DMF (0.024 mol). The mixture was stirred at room temperature for 30 minutes, then cooled to 5° C. 3-Oxo-butanoic acid ethyl ester (0.024 mol) was added slowly. The mixture was stirred at 5° C. for 30 minutes. 1-(4-aminophenyl)-2-phenylethanone (0.024 mol) was added portionwise. The mixture was stirred at 90° C. for 3 hours and dissolved in CH₂Cl₂. Ice water was added. The mixture was basified with NH₄OH and extracted with CH₂Cl₂. The organic layer was separated, dried (MgSO₄), filtered, and the solvent was evaporated. The residue was crystallized from 2-propanone/diethyl ether. The precipitate was filtered off and dried. Yielding: 0.9 g of compound 306 (11%) (mp.:136° C.).

EXAMPLE B2

Preparation of (compound 2)

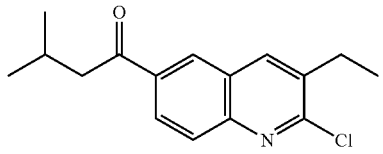

KMnO₄ (10 g) was added portionwise at room temperature to a solution of

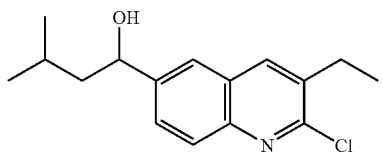

(prepared according to example A7.e) (0.022 mol) in tris (dioxa-3,6-heptyl)amine (1 ml) and CH₂Cl₂ (100 ml). The mixture was stirred at room temperature for 8 hours, filtered over celite, washed with CH₂Cl₂ and dried. The residue (6 g, 100%) was crystallized from diethyl ether/petroleum ether. The precipitate was filtered off and dried. Yield: 2 g of compound (2) (33%); mp. 82° C.

EXAMPLE B3 a) Preparation of (compound 3)

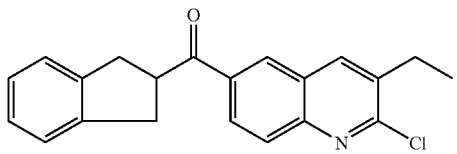

nBuLi 1.6 M (0.07 mol) was added slowly at –70° C. to a solution of intermediate (5) (0.058 mol) in THF (150 ml). The mixture was stirred at –70° C. for 30 minutes. A solution of 2,3-dihydro-1H-Indene-2-carbonitrile (0.07 mol) in THF (100 ml) was added slowly. The mixture was stirred at –70° C. for 1 hour, brought slowly to room temperature, hydrolized with H₂O and extracted with EtOAc. The organic layer was separated, dried (MgSO₄), filtered and the solvent was evaporated. The residue (22 g) was purified by column chromatography over silica gel (eluent: CH₂Cl₂/cyclohexane 80/20 to 100; 15-35 μm). The pure fractions were collected and the solvent was evaporated. The second fraction was crystallized from 2-propanone/diethyl ether. The precipitate was filtered off and dried. Yield: 0.11 g of compound (3). The filtrate was concentrated. Yield: 0.55 g of compound (3); mp. 145° C.

b) Preparation of (compound 4)

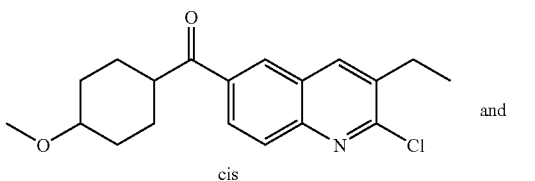

and (compound 5)

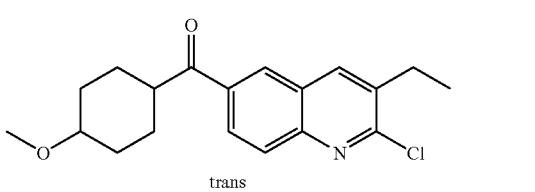

trans nBuLi 1.6 M (0.022 mol) was added slowly at –70° C. to a solution of intermediate (5) (0.018 mol) in THF (50 ml). The mixture was stirred at –70° C. for 1 hour, brought to –40° C., then cooled to –70° C. A solution of interm. 7 (0.018 mol) in THF (40 ml) was added slowly. The mixture was stirred at –70° C. for 1 hour, then brought to –20° C., hydrolyzed with H₂O and extracted with EtOAc. The organic layer was separated, dried (MgSO₄), filtered and the solvent was evaporated. The residue (6.5 g) was purified by column chromatography over silica gel (eluent: toluene/EtOAc 90/10; 15-40 μM). Two fractions (F1 and F2) were collected and the solvent was evaporated. F1 (2.4 g) was crystallized from diethyl ether. The precipitate was filtered off and dried. Yield: 1.8 g of compound (4) (29%); mp. 123° C. F2 (0.9 g) was crystallized from diethyl ether. The precipitate was filtered off and dried. Yield: 0.2 g of compound (5) (3%); mp. 120° C.

c) Preparation of (compound 7)

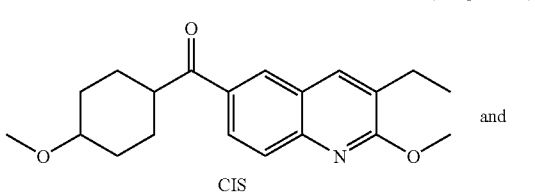

and

CIS (compound 8)

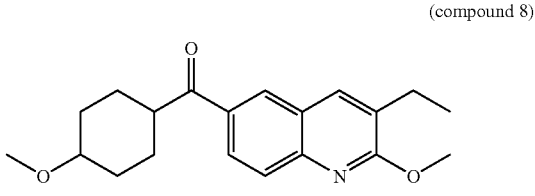

TRANS nBuLi 1.6 M in exane (0.107 mol) was added dropwise at −78° C. under N₂ flow to a mixture of intermediate (6) (0.089 mol) in THF. The mixture was stirred at −78° C. for 1 hour. A mixture of interm. 7 (150 ml) was added at −78° C. under N₂ flow. The mixture was stirred at −78° C. for 2 hours, brought to 0° C., poured out into H₂O and extracted with EtOAc. The organic layer was separated, dried (MgSO₄), filtered and the solvent was evaporated. The residue (31 g) was purified by column chromatography over silica gel (eluent: cyclohexane/ EtOAc 85/15; 20-45 µm). Two pure fractions were collected and their solvents were evaporated. Yielding: 11 g of compound (7) (38%) and 8.2 g of compound (8) (28%).

d) Preparation of (compound 503)

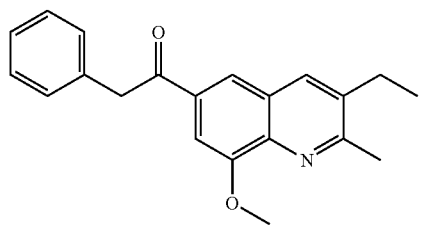

A solution of chloromethylbenzeen (0.0069 mol) in diethyl ether (8 ml) was added slowly to a suspension of Mg (0.0069 mol) in a small amount of diethyl ether. The mixture was stirred at room temperature for 30 minutes (disparition of Mg), then cooled to 5° C. A solution of interm. 27 (0.0027 mol) in THF (8 ml) was added slowly. The mixture was stirred at 5° C. for 15 minutes, then at room temperature for 2 hours, poured out into H₂O and filtered over celite. The precipitate was washed with EtOAc. The filtrate was extracted with EtOAc. The organic layer was separated, dried (MgSO₄), filtered, and the solvent was evaporated. The residue (1 g) was purified by column chromatography over kromasil (eluent: CH₂Cl₂ 100 to CH₂Cl₂/CH₃OH 99/1; 15-40 µm). The pure fractions were collected and the solvent was evaporated. The residue (0.5 g, 56%) was crystallized from diethyl ether. The precipitate was filtered off and dried. Yielding: 0.14 g of compound 503 (15%).

EXAMPLE B4

Examples of Endgoup Modifications a) Preparation of (compound 156)

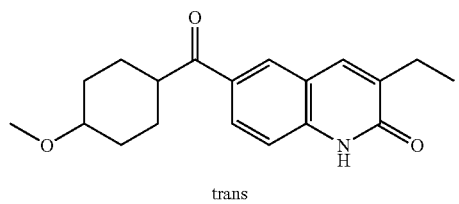

A mixture of (compound 8)

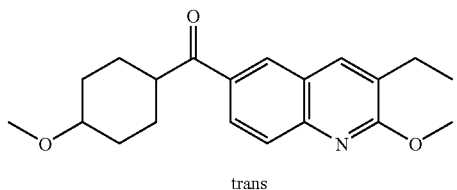

(prepared according to example B3.c) (0.018 mol) in HCl 3N (60 ml) and THF (60 ml) was stirred at 60° C. overnight. The mixture was basified with a K₂CO₃ 10% solution and extracted with CH₂C₂. The organic layer was separated, dried (MgSO₄), filtered and the solvent was evaporated. Yield: 4.6 g of compound (156) (82%).

b) Preparation of (compound 9)

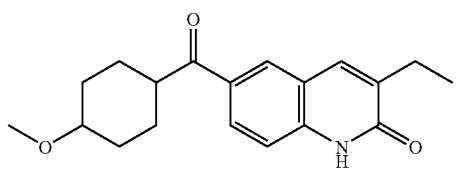

A mixture of (compound 7)

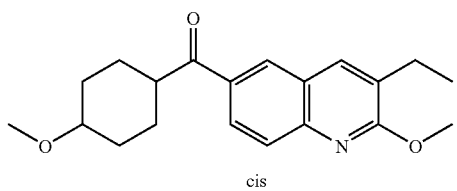

(prepared according to example B3.c) (0.0122 mol) in HCl 3N (40 ml) and THF (40 ml) was stirred and refluxed overnight, poured out into water, basified with K₂CO₃ 10% and extracted with CH₂Cl₂. The organic layer was separated, dried (MgSO₄), filtered and the solvent was evaporated. The residue was purified by column chromatography over silica gel (eluent: cyclohexane/EtOAc 40/60; 15-40 µm). The pure fractions were collected and the solvent was evaporated. Yield: 2 g of compound (9) (52%); mp. 226° C.

c) Preparation of (compound 10)

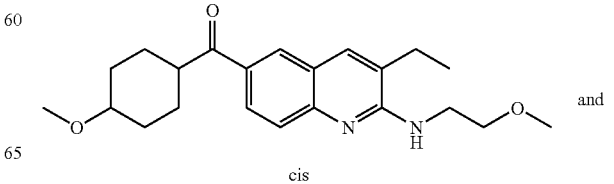

and

-continued (compound 11)

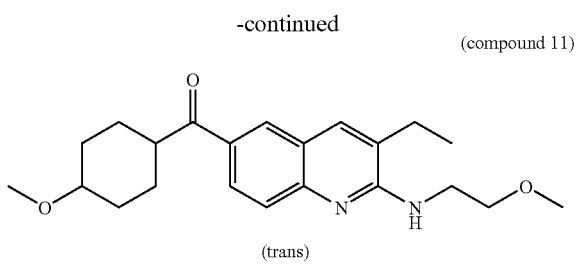
(trans)

A mixture of compound (4) (0.0015 mol), 2-methoxyethanamine (0.003 mol) and K₂CO₃ (0.003 mol) in DMF (5 ml) was stirred at 140° C. for 48 hours. H₂O was added. The mixture was extracted with EtOAc. The organic layer was separated, dried (MgSO₄), filtered and the solvent was evaporated. The residue (1 g) was purified by column chromatography over silica gel (eluent: cyclohexane/EtOAc 60/40; 15-40 µm). Two fractions were collected and the solvent was evaporated. Both fractions were crystallized separately from pentane. The precipitate was filtered off and dried. Yield: 0.05 g of compound (10) (9%; mp. 115° C.) and 0.057 g of compound (11) (10%; mp. 107° C.).

d) Preparation of (compound 12)

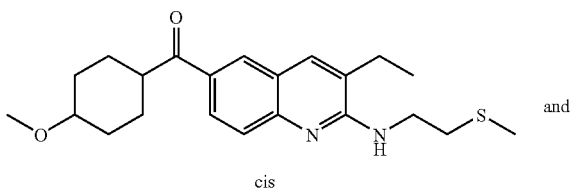
cis (compound 13)

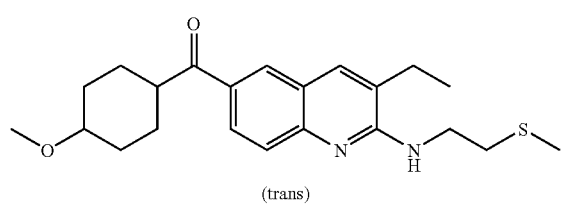
(trans)

A mixture of compound (4) (0.0015 mol) in 2-(methylthio)ethanamine (2 ml) was stirred at 120° C. for 8 hours. K₂CO₃ 10% was added. The mixture was extracted with CH₂Cl₂. The organic layer was separated, dried (MgSO₄), filtered and the solvent was evaporated. The residue (2.2 g) was purified by column chromatography over silica gel (eluent: cyclohexane/EtOAc 70/30; 15-40 µm). Two fractions were collected and the solvent was evaporated. The first fraction was crystallized from diethyl ether/petroleum ether. The precipitate was filtered off and dried. Yield: 0.08 g of compound (12) (14%); mp. 120° C. The second fraction was crystallized from diethyl ether. The precipitate was filtered off and dried. Yield: 0.18 g of compound (13) (31%); mp. 125° C.

e) Preparation of (compound 14)

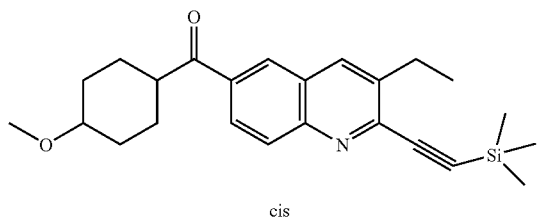
cis

A mixture of compound (4) (0.001507 mol), ethynyltrimethylsilane (0.003013 mol), CuI (0.000151 mol) and Pd(PPh₃)₄ (0.000151 mol) in N,N-diethylethanamine (5 ml) was stirred at 100° C. for 24 hours. Water was added. The mixture was filtered over celite, washed with EtOAc and the filtrate was extracted with EtOAc. The organic layer was separated, dried (MgSO₄), filtered and the solvent was evaporated. The residue (1.3 g) was purified by column chromatography over silica gel (eluent: cyclohexane/EtOAc 85/15; 15-40 µm). The pure fractions were collected and the solvent was evaporated. The residue (0.3 g) was crystallized from pentane. The precipitate was filtered off and dried. Yield: 0.11 g of compound (14) (18%); mp. 114° C.

f) Preparation of (compound 15)

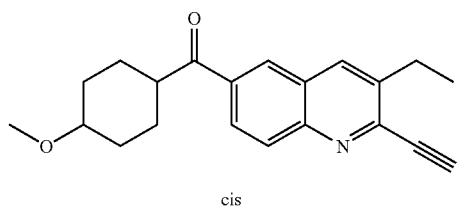
cis

A mixture of compound (14) (0.013 mol) and KF (0.038 mol) in acetic acid (50 ml) was stirred at room temperature for 2 hours. H₂O was added and the mixture was extracted with diethyl ether. The organic layer was separated, dried (MgSO₄), filtered and the solvent was evaporated. The residue (4.4 g) was purified by column chromatography over silica gel (eluent: cyclohexane/EtOAc 70/30; 15-40 µm). One fraction was collected and the solvent was evaporated. This fraction (3 g, 73%) was crystallized from diethyl ether. The precipitate was filtered off and dried. Yield: 2.45 g of compound (15) (60%); mp. 132° C.

g) Preparation of (compound 15)

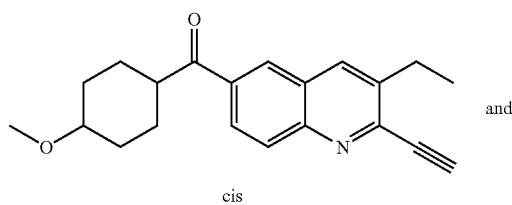
cis
and (compound 17)

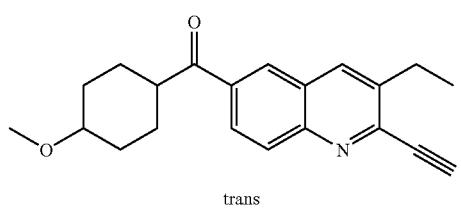
trans

A mixture of (compound 14)

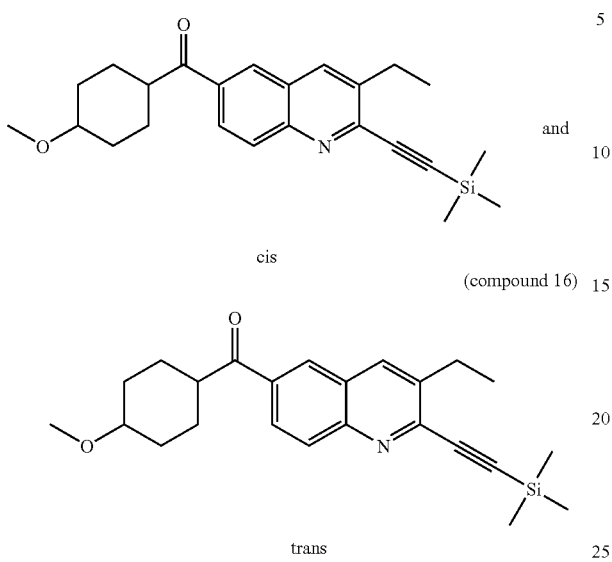

cis (compound 16)

trans prepared according to example B.7.a) (0.0056 mol) in KOH [1M, H₂O] (10 ml) and methanol (30 ml) was stirred at room temperature for 1 hour, poured out into water and extracted with EtOAc. The organic layer was separated, dried (MgSO₄), filtered and the solvent was evaporated. The residue (2.2 g) was purified by column chromatography over silica gel (eluent: cyclohexane/EtOAc 85/15 to 70/30; 15-40 µm). Two fractions were collected and the solvent was evaporated.

The first fraction was crystallized from diethyl ether. The precipitate was filtered off and dried. Yield: 0.2 g of compound (15) (11%); mp. 133° C.

The second fraction was crystallized from diethyl ether. The precipitate was filtered off and dried. Yield: 0.3 g of compound (17) (16%); mp. 128° C.

h) Preparation of (compound 18)

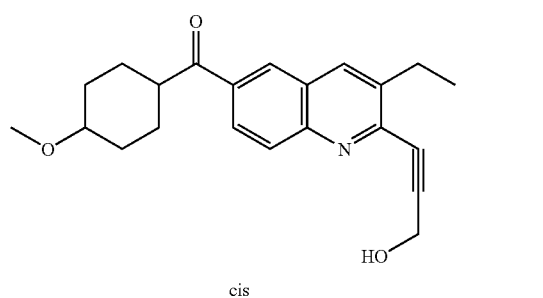

cis

A mixture of compound (4) (0.001205 mol), 2-propyn-1-ol (0.002411 mol), Pd(PPh₃)₄ (0.000121 mol) and CuI (0.000121 mol) in N,N-diethylethanamine (5 ml) was stirred at 100° C. for 2 hours. Water was added. The mixture was filtered over celite, washed with EtOAc and extracted aith EtOAc. The organic layer was separated, dried (MgSO₄), filtered and the solvent was evaporated. The residue (0.7 g) was purified by column chromatography over silica gel (eluent: CH₂Cl₂/CH₃OH 98/2; 15-40 µm). The pure fractions were collected and the solvent was evaporated. The residue was crystallized from petroleum ether and diethyl ether. The precipitate was filtered off and dried. Yield. 0.1 g of compound (18) (23%); mp. 113° C.

i) Preparation of (compound 19)

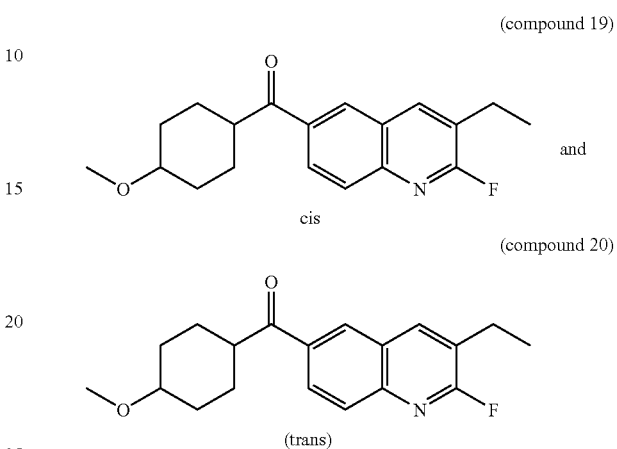

cis (compound 20)

(trans)

A mixture of compound (4) (0.006027 mol) and KF (0.024108 mol) in DMSO (20 ml) was stirred at 140° C. The solvent was evaporated till dryness. The residue was solidified in water and diethyl ether. The mixture was extracted with diethyl ether. The organic layer was separated, washed with diethyl ether, washed with a saturated solution of NaCl, dried (MgSO₄), filtered and the solvent was evaporated. The residue (1.7 g) was purified by column chromatography over silica gel (eluent: cyclohexane/EtOAc 85/15; 15-40 µm). Three fractions were collected and their solvents were evaporated.

The first fraction was crystallized from petroleum ether. The precipitate was filtered off and dried. Yield: 0.21 g of compound (19) (11%); mp. 92° C.

The second fraction was crystallized from petroleum ether. The precipitate was filtered off and dried. Yield: 0.33 g of compound (20) (17%); mp. 114° C.

j) Preparation of (compound 21)

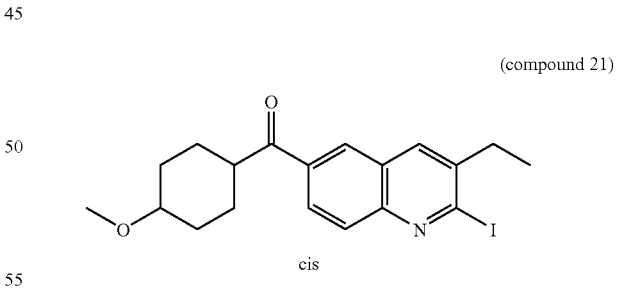

cis

A mixture of compound (4) (0.003013 mol), acetyl chloride (0.003315 mol) and sodium iodide (0.006027 mol) in CH₃CN (10 ml) was stirred and refluxed for 1 hour. K₂CO₃ 10% was added. The mixture was extracted with CH₂Cl₂. The organic layer was separated, dried (MgSO₄), filtered and the solvent was evaporated. The residue (1 g) was purified by column chromatography over silica gel (eluent: cyclohexane/ EtOAc 80/20; 15-40 µm). Two fractions were collected and their solvents were evaporated. The first fraction was crystallized from petroleum ether. The precipitate was filtered off and dried. Yield: 0.12 g of compound (21); mp. 110° C.

k) Preparation of (compound 22)

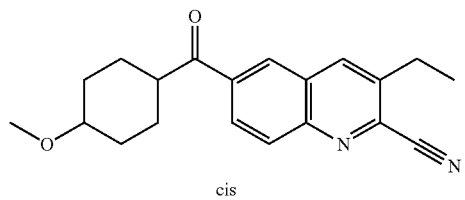

cis

A mixture of compound (21) (0.000898 mol), trimethylsilanecarbonitrile (0.001347 mol) and Pd(PPh₃)₄ (0.00009 mol) in N,N-diethylethanamine (5 ml) was stirred at 100° C. for 2 hours. Water was added. The mixture was extracted with EtOAc. The organic layer was separated, dried (MgSO₄), filtered and the solvent was evaporated. The residue (0.4 g) was purified by column chromatography over silica gel (eluent: cyclohexane/EtOAc 80/20; 15-40 μm). The pure fractions were collected and the solvent was evaporated. The residue (0.18 g, 62%) was crystallized from petroleum ether. The precipitate was filtered off and dried. Yield: 0.13 g of compound (22) (45%); mp. 138° C.

l) Preparation of (compound 23)

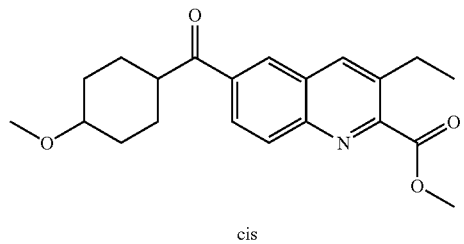

cis (compound 24)

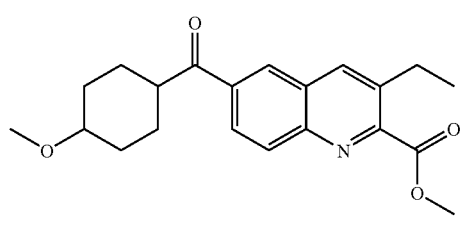

(trans)

(compound 25)

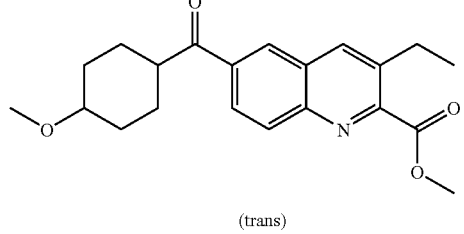

cis (compound 26)

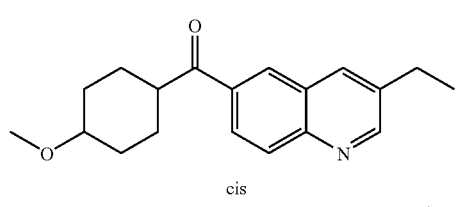

(trans)

A mixture of compound (4) (0.00603 mol), Pd(OAc)₂ (0.000603 mol), PPh₃ (0.00904 mol) and K₂CO₃ (0.012054 mol) in CO (gas) and methanol (40 ml) was stirred at 90° C. for 8 hours under a 5 bar pressure of CO. H₂O was added. The mixture was extracted with EtOAc. The organic layer was separated, dried (MgSO₄), filtered and the solvent was evaporated. The residue (6 g) was purified by column chromatography over silica gel (eluent: CH₂Cl₂/CH₃OH 100/0 to 98/2; 15-35 μm). Four fractions (F1-F4) were collected and the solvent was evaporated. Yield: 0.13 g (cis) F1; 0.02 g F2 (cis, compound 25); 0.055 g F3 (trans, 3%) and 0.11 g F4 (trans; compound 26).

F1 was crystallized from petroleum ether. The precipitate was filtered off and dried. Yield: 0.03 g of compound (23) (1%); mp. 91° C.

F3 was crystallized from petroleum ether. The precipitate was filtered off and dried. Yield: 0.035 g of compound (24) (1%); mp. 99° C.

m) Preparation of (compound 25)

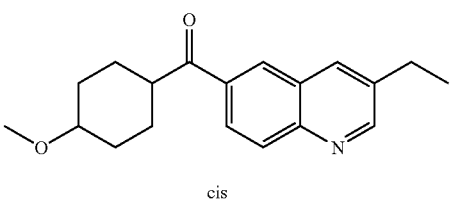

cis

A mixture of compound (4) (0.009 mol) and Zn (0.027 mol) in acetic acid (30 ml) was stirred at 60° C. for 4 hours, filtered over celite, washed with CH₂Cl₂, evaporated till dryness, solubilized in CH₂Cl₂ and washed with K₂CO₃ 10%. The organic layer was separated, dried (MgSO₄), filtered and the solvent was evaporated. The residue (4 g) was purified by column chromatography over silica gel (eluent: cyclohexane/EtOAc 75/25; 15-40 μm). One fraction was collected and the solvent was evaporated. This fraction (1 g 37%) was crystallized from petroleum ether. The precipitate was filtered off and dried. Yield: compound (25); mp. 88° C.

n) Preparation of (compound 27)

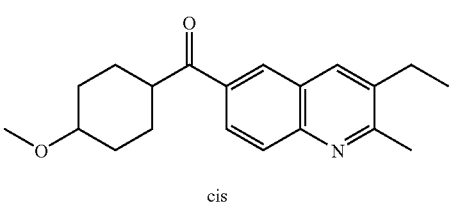

cis

A mixture of compound (4) (0.001502 mol), Sn(CH₃)₄ (0.003004 mol) and Pd(PPh₃)₄ (0.00015 mol) in methylbenzene (5 ml) was stirred and refluxed for 3 hours. K₂CO₃ 10% was added. The mixture was extracted with EtOAc. The organic layer was separated, dried (MgSO₄), filtered and the solvent was evaporated. The residue (0.7 g) was purified by column chromatography over silica gel (eluent: cyclohexane/EtOAc 85/15; 15-40 μm). Two fractions (F1 and F2) were collected and their solvents were evaporated. Yield: 0.27 g (F 1, starting material) and 0.14 g (F2). F2 was crystallized from o) Preparation of (compound 28)

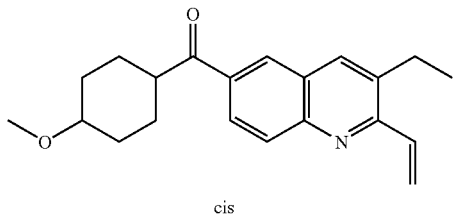

cis

A mixture of compound (4) (0.001507 mol), tributylethenylstannane (0.002260 mol) and Pd(PPh$_3$)$_4$ (0.000151 mol) in dioxane (5 ml) was stirred at 80° C. for 8 hours. Water was added. The mixture was filtered over celite, washed with EtOAc and extracted with EtOAc. The organic layer was separated, dried (MgSO$_4$), filtered and the solvent was evaporated. The residue (0.65 g) was purified by column chromatography over silica gel (eluent: cyclohexane/EtOAc 90/10; 15-40 μm). The pure fractions were collected and the solvent was evaporated. The residue was crystallized from petroleum ether. The precipitate was filtered off and dried. Yield: 0.07 g of compound (28) (14%); mp. 108° C.

p) Preparation of (compound 29)

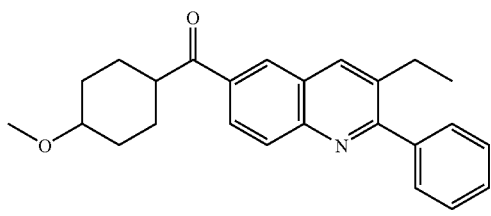

trans

A mixture of compound (5) (0.001507 mol), triphenyl (phenylmethyl)stannane (0.002260 mol) and Pd(PPh$_3$)$_4$ (0.000151 mol) in dioxane (5 ml) was stirred at 80° C. for 8 hours. Water was added. The mixture was extracted with EtOAc. The organic layer was separated, dried (MgSO$_4$), filtered and the solvent was evaporated. The residue (1.4 g) was purified by column chromatography over silica gel (eluent: CH$_2$Cl$_2$/EtOAc 96/4; 15-40 μm). The pure fractions were collected and the solvent was evaporated. The residue (0.38 g) was crystallized from petroleum ether. The precipitate was filtered off and dried. Yield: 0.16 g of compound (29) (28%); mp. 112° C.

q) Preparation of (compound 30)

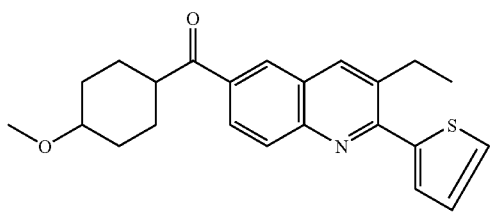

cis

A mixture of compound (4) (0.001507 mol), tributyl-2-thienylstannane (0.00226 mol) and Pd(PPh$_3$)$_4$ (0.0001507 mol) in dioxane (5 ml) was stirred at 80° C. for 8 hours. K$_2$CO$_3$ 10% was added. The mixture was extracted with EtOAc. The organic layer was separated, dried (MgSO$_4$), filtered and the solvent was evaporated. The residue (1.7 g) was purified by column chromatography over silica gel (eluent: cyclohexane/EtOAc 85/15; 15-40 μm). The pure fractions were collected and the solvent was evaporated. The residue (0.65 g) was crystallized from diethyl ether. The precipitate was filtered off and dried. Yield: 0.35 g of compound (30) (61%); mp. 142° C.

r) Preparation of (compound 31)

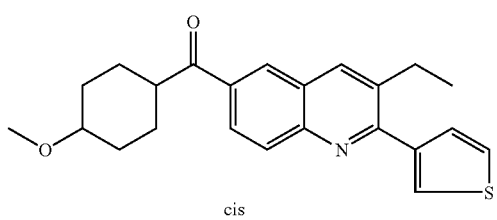

cis

A mixture of compound (4) (0.0015 mol), 3-thienyl boronic acid (0.00226 mol), Pd(PPh$_3$)$_4$ (0.00015 mol) and dioxane was stirred and refluxed for 24 hours. K$_2$CO$_3$ 10% was added. The mixture was extracted with EtOAc. The organic layer was separated, dried (MgSO$_4$), filtered and the solvent was evaporated. The residue (0.8 g) was purified by column chromatography over silica gel (eluent: cyclohexane/EtOAc is 80/20; 15-40 μm). The pure fractions were collected and the solvent was evaporated. The residue (0.4 g, 70%) was crystallized from petroleum ether. The precipitate was filtered off and dried. Yield: 0.39 g of compound (31) (68%); mp. 113° C.

s) Preparation of (compound 32)

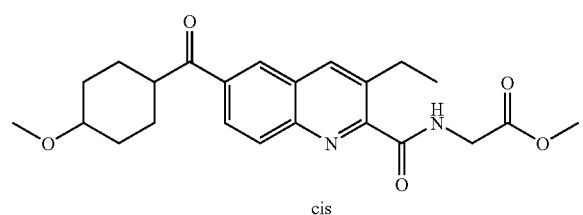

cis

A mixture of compound (4) (0.003 mol), glycine methyl ester monohydrochloride (0.0066 mol) and Pd(PPh)$_4$ (0.0003 mol) in Et$_3$N (2 ml) and toluene (10 ml) was stirred at 100° C. under 5 bar pressure of CO for 8 hours, filtered over celite, washed with CH$_2$Cl$_2$ and evaporated. The residue (2 g) was purified by column chromatography over silica gel (eluent: cyclohexane/EtOAc 80/20; 75-35 μm). One fraction was collected and the solvent was evaporated. This fraction (1 g 80%) was crystallized from diethyl ether. The precipitate was filtered off and dried. Yielding: 0.46 g of compound (32) (37%).

t) Preparation of (compound 33)

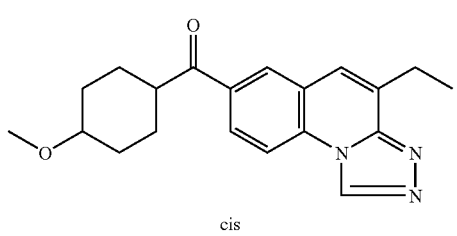

cis (compound 34)

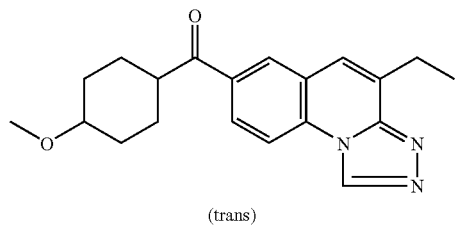

(trans)

A mixture of compound (4) (0.003 mol) and hydrazinecarboxaldehyde (0.0045 mol) in 1-butanol (15 ml) was stirred and refluxed overnight, poured out into water and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/CH$_3$OH/NH$_4$OH 95/5/0.1; 15-40 μm). Two fractions (F1 and F2) were collected and their solvents were evaporated. Yield: 0.3 g F1 and 0.3 g F2.

F1 was crystallized from CH$_3$CN and diethyl ether. The precipitate was filtered off and dried. Yield: 0.102 g of compound (33); mp. 224° C.

F2 was crystallized from CH$_3$CN and diethyl ether. The precipitate was filtered off and dried. Yield: 0.2 g of compound (34); mp. 185° C.

u) Preparation of (compound 35)

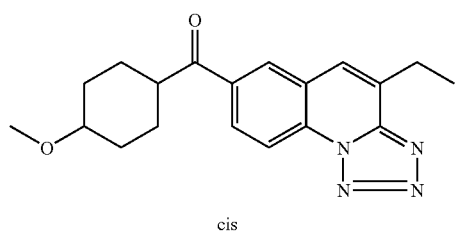

cis

A mixture of compound 4 (0.015 mol) and NaN$_3$ (0.045 mol) in DMF (50 ml) was stirred at 140° C. for 2 hours. K$_2$CO$_3$ 10% was added and the mixture was extracted with EtOAc. The organic layer was separated, dried (MgSO$_4$), filtered and the solvent was evaporated. The residue (6 g) was purified by column chromatography over silica gel (eluent: cyclohexane/EtOAc 60/40; 15-40 μm). The first fraction was collected and the solvent was evaporated. The residue was crystallized from diethyl ether. The precipitate was filtered off and dried. Yield: 1.26 g of compound (35) (24%); mp. 160° C.

v) Preparation of (compound 36)

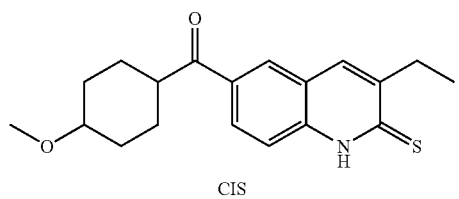

CIS (compound 37)

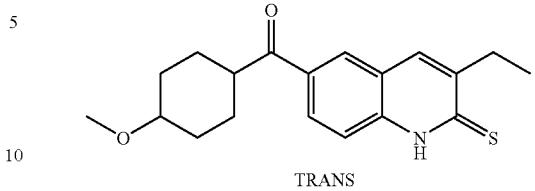

TRANS

A mixture of compound (4) (0.009 mol) and thiourea (0.0099 mol) in ethyl alcohol (30 ml) was stirred and refluxed for 12 hours and a solution of KOH (0.0149 mol) in H$_2$O (5 ml) was added slowly. The mixture was stirred and refluxed for 1 hour, poured out into water and extracted with CH$_2$Cl$_2$. The organic layer was separated, dried (MgSO$_4$), filtered and the solvent was evaporated. The residue was purified by column chromatography over silica gel (cyclohexane/EtOAc 70/30; 15-40 μm). The pure fractions were collected and the solvent was evaporated. Yielding: 1.1 g of F1 (37%) and 0.4 g of F2 (13%). F1 was crystallized from 2-propanone. The precipitate was filtered off and dried. Yielding: compound (36). F2 was crystallized from 2-propanone. The precipitate was filtered off and dried. Yielding: compound (37).

w) Preparation of (compound 38)

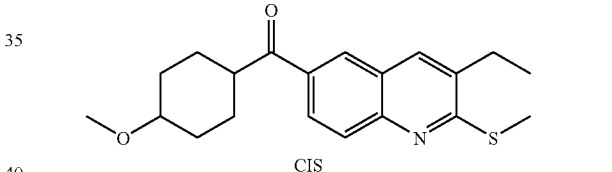

CIS (compound 39)

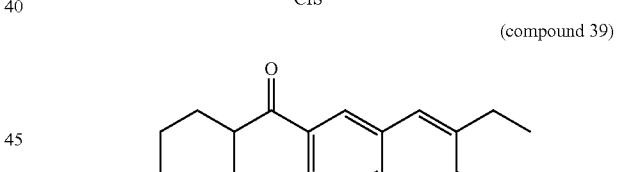

TRANS

CH$_3$I (0.0034 mol) was added slowly at room temperature to a solution of compound (36) (0.0015 mol), compound (37) (0.0015 mol) and K$_2$CO$_3$ (0.0034 mol) in acetone (15 ml). The mixture was stirred at room temperature for 8 hours. Water was added and the mixture was extracted with CH$_2$Cl$_2$. The organic layer was separated, dried (MgSO$_4$), filtered and the solvent was evaporated. The residue (1.2 g) was purified by column chromatography over silica gel (eluent: cyclohexane/EtOAc 85/15; 15-40 μm). The pure fractions were collected and the solvent was evaporated. Yielding: 0.6 g F1 (57%), and 0.18 g F2 (17%). F1 was crystallized from diethyl ether. The precipitate was filtered off and dried. Yielding: 0.28 g compound (38) (27%). F2 was crystallized from diethyl ether. The precipitate was filtered off and dried. Yielding: 0.065 g of compound (39) (6%).

x) Preparation of

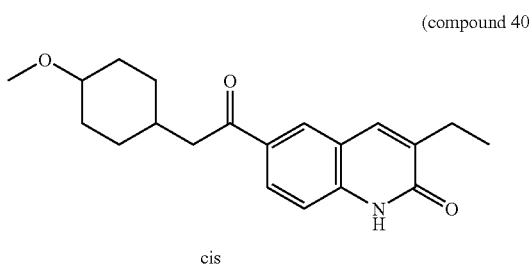
(compound 40)

A mixture of

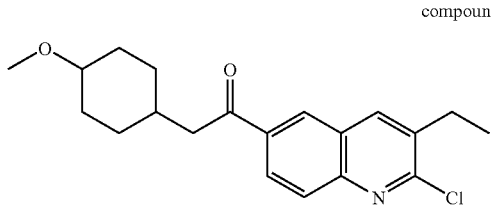
compound (41)

prepared according to example B3b (0.0014 mol) in HCl 3N (5 ml) and THF (5 ml) was stirred and refluxed for a weekend, then poured out into H₂O, basified with K₂CO₃ and extracted with CH₂Cl₂. The organic layer was separated, dried (MgSO₄), filtered and the solvent was evaporated. Yielding: 0.5 g of F. This fraction F was crystallized from 2-propanone. The precipitate was filtered off and dried. Yielding: 0.35 g of compound (40) (74%).

y) Preparation of

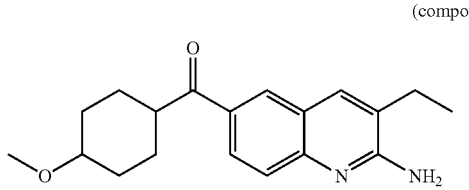
(compound 188)

A mixture of compound (5) (0.045 mol), acetamide (0.90013 mol) and K₂CO₃ (0.225 mol) was stirred and refluxed at 200° C. for 2 hours, cooled at room temperature, poured out into H₂O/CH₂Cl₂; and extracted with CH₂Cl₂. The organic layer was separated, dried (MgSO₄), filtered and the solvent was evaporated till dryness. The residue (14.4 g) was crystallized from CH₃OH. The precipitate was filtered off and dried. The filtrate was evaporated. The residue (11.27 g) was purified by column chromatography over silica gel (eluent CH₂Cl₂/CH₃OH/NH₄OH 96/4/0.1; 15-35 µm). The pure fractions were collected and the solvent was evaporated. Yielding: 4.2 g of compound (188) (65%).

z) Preparation of

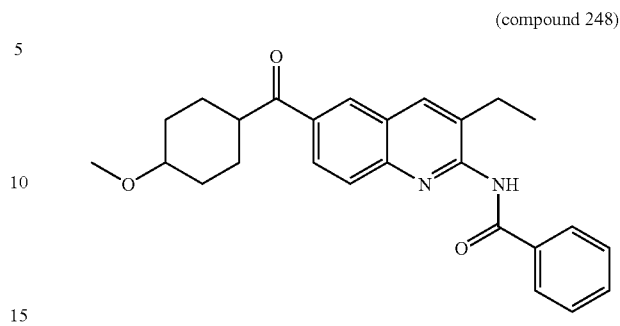
(compound 248)

A mixture of compound (188) (0.00032 mol), benzoic acid (1.5 equiv., 0.00048 mol), 1-ethyl-3-(3'-dimethylaminopropyl)carbodiimide. HCl (1:1) (1.5 equiv., 0.00048 mol), N-hydroxybenzotriazole (1.5 equiv., 0.00048 mol) and Et₃N (1 equiv., 0.00032 mol) in CH₂CL₂ (2 ml) was stirred at room temperature for 15 hours. The solvent was evaporated. The residue was purified by HPLC and the product fractions were collected and the solvent was evaporated. Yield: 0.066 g of compound (205) (49.50%).

aa) Preparation of

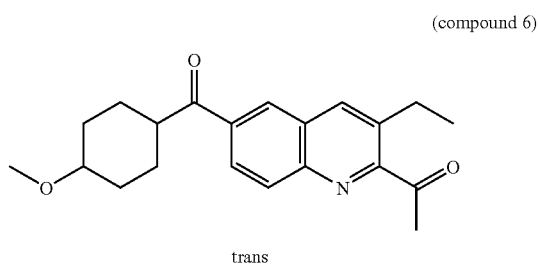
(compound 6)

A mixture of interm. 20 (0.001507 mol) in HCl 3N (10 ml) and THF (10 ml) was stirred at room temperature for 8 hours, basified with K₂CO₃ 10% and extracted with CH₂Cl₂. The organic layer was separated, dried (MgSO₄), filtered and the solvent was evaporate. The residue (1.2 g) was purified by column chromatography over silica gel (eluent: cyclohexane/EtOAc 85/15; 15-40 µm). The pure fractions were collected and the solvent was evaporated. The residue (0.4 g) was crystallized from petroleum ether. The precipitate was filtered off and dried. Yield: 0.3 g of compound (6) (58%); mp. 108° C.

ab) Preparation of

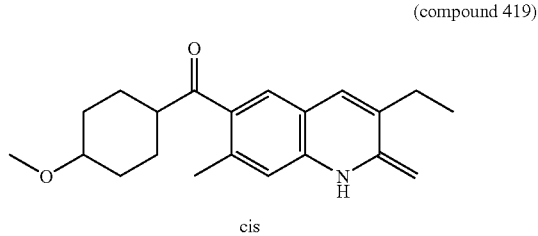
(compound 419)

A mixture of compound 213 (prepared according to B4) (0.00305 mol) and CH₃ONa (30% in CH₃OH) (0.00916 mol) in CH₃OH (25 ml) was stirred and refluxed for 15 hours then cooled to room temperature, poured out into H₂O and extracted with EtOAc. The organic layer was separated, dried (MgSO₄), filtered, and the solvent was evaporated till dryness. The residue (1.1 g) was purified by column chromatography over silica gel (eluent: cyclohexane/EtOAc; 40/60; 15-40 μm). Two fractions were collected and the solvent was evaporated. Yielding: 0.3 g F1 and 0.5 g F2 (50%) F2 was crystallized from diethyl ether/petroleum ether. The precipitate was filtered off and dried. Yielding: 0.26 g F1 was crystallized from pentane. The precipitate was filtered off and dried. Yielding: 0.19 g. This fraction was purified by column chromatography over silica gel (eluent: CH₂Cl₂/CH₃OH; 98/2; 15-40 μm). The pure fractions were collected and the solvent was evaporated. Yielding: 0.11 g. This fraction was purified by column chromatography over kromasil (eluent: CH₃OH/H₂O; 70/30). The pure fractions were collected and the solvent was evaporated. Yielding: 0.09 g. (9%) This fraction was crystallized from diethyl ether. The precipitate was filtered off and dried. Yielding: 0.08 g of compound 419 (8%).

EXAMPLE B5

Preparation of

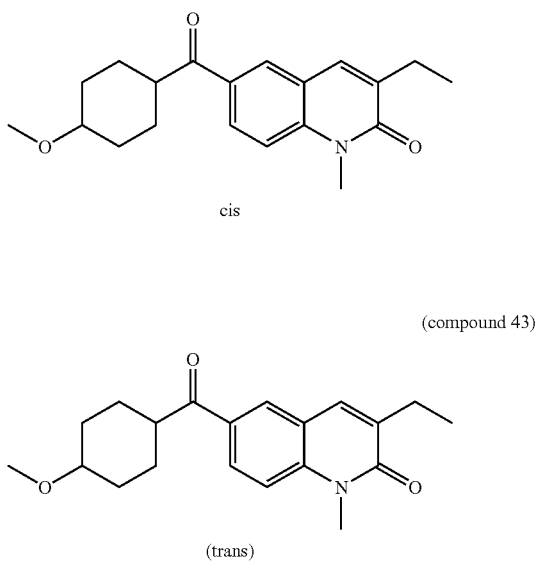

(compound 42)

cis (compound 43)

(trans)

Iodomethane (0.00456 mol) was added at 5° C. to a mixture of compound (9) (0.0019 mol), compound (8) (0.0019 mol) and tBuOK (0.00456 mol) in THF (30 ml) under N₂ flow. The mixture was stirred at room temperature overnight, poured out into H₂O and extracted with CH₂Cl₂. The organic layer was separated, dried (MgSO₄), filtered and the solvent was evaporated. The residue was purified by column chromatography over silica gel (eluent: cyclohexane/EtOAc 65/35; 15-40 μm). Two fractions were collected and the solvent was evaporated. Yield: 0.35 g of compound (42) (30%; mp. 125° C.) and 0.35 g of compound (43) (30%; mp. 116° C.).

EXAMPLE B6 a) Preparation of

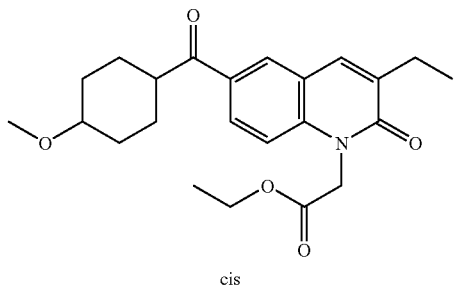

(compound 44)

cis

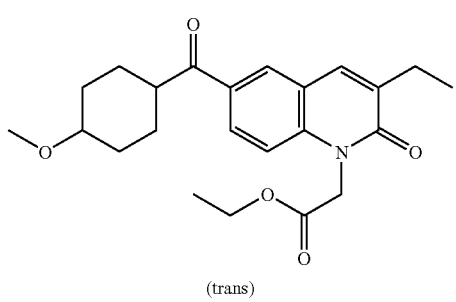

(compound 45)

(trans)

NaH 60% (0.01068 mol) was added at 0° C. under N₂ flow to a mixture of compound (8) and compound (9) (0.0089 mol). The mixture was stirred for 30 minutes.

Ethyl bromoacetate (0.01068 mol) was added at 0° C. The mixture was stirred at room temperature for 1 hour, hydrolized with water and extracted with EtOAc. The organic layer was separated, dried (MgSO₄), filtered and the solvent was evaporated. The residue was purified by column chromatography over silica gel (eluent: cyclohexane/EtOAc 60/40; 15-40 μm). The desired fractions (F1-F4) were collected and the solvent was evaporated. Yield: 0.11 g F1; 0.13 g F2; 0.75 g F3 and 0.8 g F4.

F3 was crystallized from diethyl ether. The precipitate was filtered off and dried. Yield: compound (44); mp. 152° C.

F4 was crystallized from diethyl ether. The precipitate was filtered off and dried. Yield: compound (45); mp. 147° C.

b) Preparation of

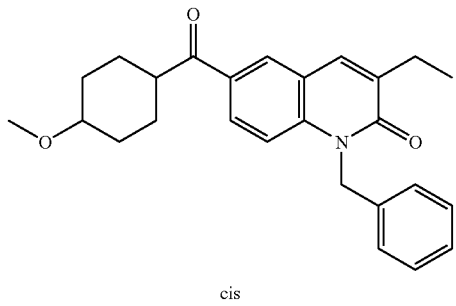

(compound 46)

cis

-continued (compound 47)

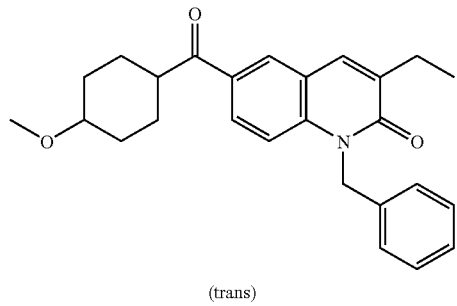

(trans)

Bromomethylbenzene (0.007 mol) was added dropwise at 0° C. under N₂ flow to a solution of compound (8) and compound (9) (0.0064 mol) and NaH 60% (0.007 mol) in DMF (40 ml). The mixture was stirred at room temperature for 1 hour, hydrolized with water and extracted with EtOAc. The organic layer was separated, washed with water, dried (MgSO₄), filtered and the solvent was evaporated. The residue was purified by column chromatography over silica gel (eluent: cyclohexane/EtOAc 70/30; 15-40 μm). The desired fractions (F1-F4) were collected and the solvent was evaporated. Yield: 0.15 g F1, 0.1 g F2, 0.6 g F3 (23%) and 0.8 g F4.

F3 was crystallized from diethyl ether. The precipitate was filtered off and dried. Yield: 0.13 g of compound (46); mp. 137° C.

F4 was crystallized from DIPE and petroleum ether. The precipitate was filtered off and dried. Yield: compound (47); mp. 130° C.

EXAMPLE B7 a) 3-Chlorobenzenecarboperoxoic acid (0.088 mol) was added at 0° C. to a solution of compound (48) (prepared according to example B2) (0.044 mol) in CH₂Cl₂ (200 ml) and the mixture was stirred at room temperature for 12 hours. The mixture was washed with K₂CO₃ 10%. The organic layer was dried (MgSO₄), filtered off and evaporated. The residue was recrystallized from (C₂H₅)₂O. Yield: 8.2 g of cyclohexyl (3-methyl-6-quinolinyl)methanone,1-oxide (compound 49) (69%).

b) 4-Methyl benzenesulfonyl chloride (0.043 mol) was added to a solution of compound (49) (0.028 mol) in K₂CO₃ (400 m) and CH₂Cl₂ (400 ml) and the mixture was stirred at room temperature for 1 hour. The mixture was extracted with CH₂Cl₂. The organic layer was dried (MgSO₄), filtered off and evaporated. The residue was recrystallized from (C₂H₅)₂O. Yield: 6.64 g of 6-(cyclohexylcarbonyl)-3-methyl-2(1H)-quinolinone (compound 50) (85%); mp. 256.1° C.

EXAMPLE B8 a) Preparation of (compound 51)

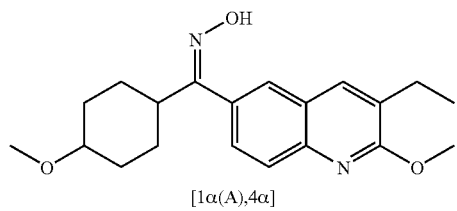

[1α(A),4α]

(compound 52)

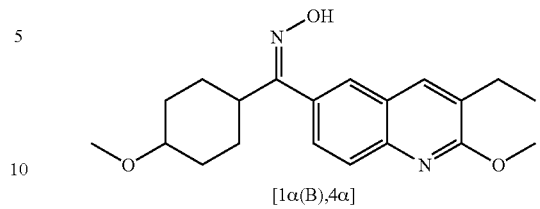

[1α(B),4α]

A mixture of compound (7) (0.0229 mol), hydroxylamine (0.0252 mol) and N,N-diethylethanamine (0.0252 mol) in ethanol (100 ml) was stirred and refluxed for 6 hours, poured out into water and extracted with CH₂Cl₂. The organic layer was separated, dried (MgSO₄), filtered and the solvent was evaporated. The residue was crystallized from CH₃CN. The precipitate was filtered off and dried. The residue was purified by column chromatography over silica gel (eluent: CH₂Cl₂/EtOAc 80/20; 15-40 μm). Two fractions were collected and the solvent was evaporated. Yielding: 2.8 g of compound (44) (36%; mp. 133° C.) and 3 g of compound (45) (38%; mp. 142° C.).

b) Preparation of (compound 53)

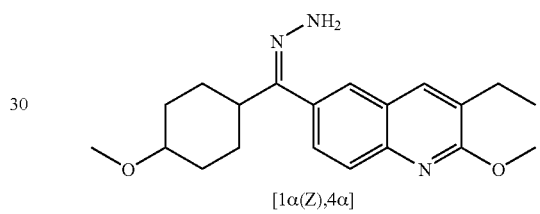

[1α(Z),4α]

Hydrazine (0.41 mol) was added at room temperature to a solution of compound (7) (0.015 mol) in ethanol (75 ml). The mixture was stirred and refluxed for 1 night, poured out into water and extracted with CH₂Cl₂. The organic layer was separated, dried (MgSO₄), filtered and the solvent was evaporated. The residue was purified by column chromatography over silica gel (eluent: CH₂Cl₂/CH₃OH/NH₄OH 98/2/0.1). The pure fractions were collected and the solvent was evaporated. The residue was crystallized from diethyl ether. The precipitate was filtered off and dried. Yielding: 0.8 g of compound (53) (15%); mp. 110° C.

EXAMPLE B9

Preparation of (compound 520)

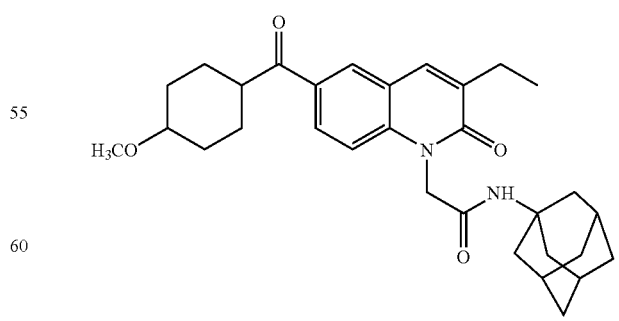

Procedure for compounds 400, 401, 402, 403, 404 and 405.
A mixture of interm. 21 (prepared according to A11) (0.000269 mol), amantadine hydrochloride (0.000404 mol; 1.5 eq.), N'-(ethylcarbonimidoyl)-N,N-dimethyl-1,3-propanediamine hydrochloride (0.000404 mol; 1.5 equiv.), 1-hydroxy-1H-benzotriazole (0.000404 mol; 1.5 equiv.) and Et₃N (0.000269 mol) in CH₂Cl₃ (2 ml) was stirred at room temperature for 12 hours. The solvent was evaporated. The residue was purified by HPLC. The product fractions were collected and the solvent was evaporated. Yield: 0.063 g of compound 520 (46.37%).

EXAMPLE B10

Preparation of

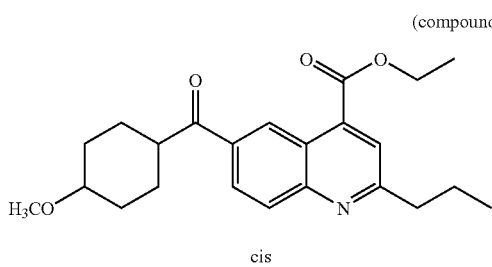

(compound 233)

cis

A mixture of intermediate 27 (0.0026 mol) and intermediate 26 (0.0026 mol) in EtOH (380 ml) and H₂SO₄ conc. (19 ml) was stirred and refluxed for 15 hours, the cooled to room temperature, poured out into ice water, basified with K₂CO₃ and extracted with EtOAc. The organic layer was separated, dried (MgSO₄), filtered, and the solvent was evaporated. The residue (17.9 g) was purified by column chromatography over silica gel (eluent: cyclohexane/EtOAc; 80/20; 15-35 μm). The pure fractions were collected and the solvent was evaporated. Yielding: 0.85 g of F1, 1.1 g F2 and 11.5 g of F3. F1 and F2 were crystallized separately from petroleum ether. The precipitate was filtered off and dried. Yielding: 0.34 g of compound 233.

EXAMPLE B11

Preparation of

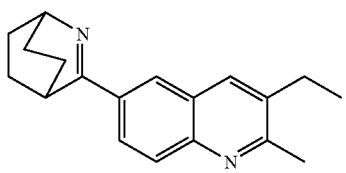

(compound 511)

A mixture of compound 22 (prepared according to B4) (0.004 mol) in HCl (3N) (20 ml) and THF (20 ml) was stirred and refluxed for 8 hours, poured out on ice, basified with NH₄OH and extracted with CH₂Cl₂. The organic layer was separated, dried (MgSO₄), filtered, and the solvent was evaporated. The residue (1.2 g) was purified by column chromatography over silica gel (eluent: CH₂Cl₂/CH₃OH/NH₄OH; 93/7/0.5; 15-40 μm). Two fractions were collected and the solvent was evaporated. Yielding: 0.5 g F1 (41%) and 0.4 g of F2. F1 was crystallized from petroleum ether. The precipitate was filtered off and dried. Yielding: 0.17 g of compound 511 (14%).

EXAMPLE B12

Preparation of

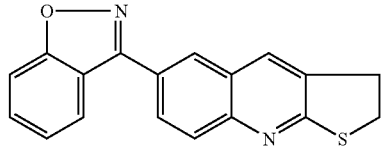

(compound 514)

A mixture of compound 524 (prepared according to B9a) (0.0018 mol) and KOH 85% (0.0094 mol) in EtOH (15 ml) was stirred and refluxed for 24 hours, poured out into H₂O and extracted with CH₂Cl₂. The organic layer was separated, dried (MgSO4), filtered, and the solvent was evaporated. The residue was purified by column chromatography over silica gel (eluent: CH₂Cl₂/Cyclohexane 80/20; 15-40 μm). Two fractions were collected and the solvent was evaporated. Yielding: 0.35 g F1 (64%) and 0.17 g (SM) F1 was crystallized from diethyl ether. The precipitate was filtered off and dried. Yielding: 0.33 g of compound 514 (60%) (mp.:185° C.).

EXAMPLE B13

Preparation of

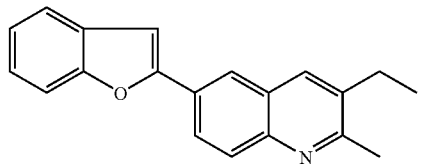

(compound 515)

A mixture of interm. 28 (0.019 mol), 2-benzofuranylboronic acid (0.028 mol), Pd(PPh₃)₄ (0.001 mol) and BHT (a few quantity) in dioxane (25 ml) and Na₂CO₃ [2] (25 ml) was stirred and refluxed for 8 hours and extracted with EtOAc. The aqueous layer was basified with NH₄OH and extracted with CH₂Cl₂. The organic layer was separated, dried (MgSO₄), filtered, and the solvent was evaporated. The residue (3.6 g) was purified by column chromatography over silica gel (eluent: CH₂Cl₂/CH₃OH 99/1; 15-40 μm). The pure fractions were collected and the solvent was evaporated. Yielding: 1.8 g (33%). This fraction was crystallized from 2-propanone/diethyl ether. The precipitate was filtered off and dried. Yielding: 0.39 g of compound 515 (7%) (mp.:134° C.).

EXAMPLE B14

Preparation of

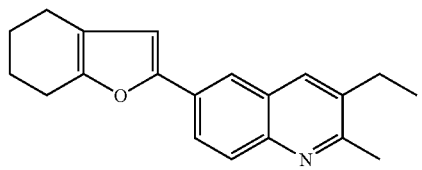

(compound 526)

Triethylsilane (0.0012 mol) was added slowly at room temperature to a solution of interm. 32 (0.004 mol) in CF₃COOH (5 ml) and AcOH (10 ml). NaBH₄ (0.0012 mol) was added portionwise under N₂ flow. The mixture was stirred at room temperature for 8 hours, poured out on ice, basified with K₂CO₃ and extracted with CH₂Cl₂. The organic layer was separated, dried (MgSO₄), filtered, and the solvent was evaporated. The residue (1.2 g) was purified by column chromatography over silica gel (eluent: CH₂Cl₂/CH₃OH 99/1; 15-40 μm). Two fractions were collected and the solvent was evaporated. Yielding: 0.5 g F1 (43%) and 0.4 g F2. F1 was dissolved in iPrOH. HCl/iPrOH (1 eq) were added. The precipitate was filtered off and dried; Yielding: 0.32 g of compound 526 (mp.: 248° C.).

EXAMPLE B15

Preparation of

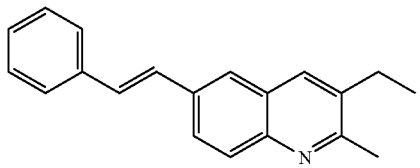

(compound 471)

A mixture of interm. 33 (0.082 mol) and 3-chloro-2-ethyl-2-butenal (0.098 mol) in AcOH (200 ml) was stirred and refluxed for 8 hours. The solvent was evaporated till dryness. The residue was dissolved in $CH_2Cl_2$ and washed with $K_2CO_3$ 10%. The organic layer was separated, dried ($MgSO_4$), filtered, and the solvent was evaporated. The residue (27 g) was purified by column chromatography over silica gel (eluent: $CH_2Cl_2$/EtOAc 95/5 to 92/8; 15-35 μm). Two fractions were collected and the solvent was evaporated. Yielding: 0.7 g of F1 and 5.3 g F2. F1 was crystallized from 2-propanone/diethyl ether. The precipitate was filtered off and dried. Yielding: 0.25 g of compound 471 (2%) (mp.: 140° C.).

Tables 1 to 8 list the compounds of formula (I-A) and (I-B) which were prepared according to one of the above examples.

TABLE 1

| Co. no. | Ex. no. | $R^2$ | $R^3$ | $R^4$ | $R^1$ | physical data |
|---|---|---|---|---|---|---|
| 54 | B2 | Cl | ethyl | H | 6-fluoro-2-methylchroman-2-yl | — |
| 3 | B3a | Cl | ethyl | H | 2-indanyl | mp. 145° C. |
| 55 | B3b | Cl | ethyl | H | 2-norbornyl | mp. 131° C. |
| 56 | B3b | Cl | ethyl | H | benzyloxyethyl | mp. 104° C. |
| 57 | B3b | Cl | ethyl | H | phenylethyl | mp. 100° C. |
| 58 | B3b | Cl | ethyl | H | 2-tetralinyl | mp. 126° C. |
| 59 | B3b | Cl | ethyl | H | 1,4-benzodioxan-2-yl | mp. 150° C. |
| 60 | B3b | Cl | ethyl | H | chroman-3-yl | mp. 138° C. |
| 61 | B3b | $OCH_3$ | ethyl | H | 2-norbornyl | — |

TABLE 1-continued

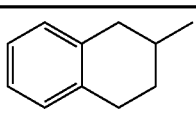

| Co. no. | Ex. no. | R² | R³ | R⁴ | R¹ | physical data |
|---|---|---|---|---|---|---|
| 62 | B3b | OCH₃ | ethyl | H | 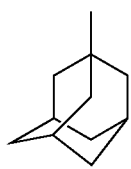 | mp. 130° C. |
| 63 | B3b | OCH₃ | ethyl | H | 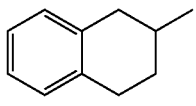 | mp. 116° C. |
| 64 | B3b | Cl | ethyl | H | —(CH₂)₂—O—CH₃ | mp. 82° C. |
| 65 | B3b | OCH₃ | ethyl | H | 1-methylcyclohexyl | mp. 82° C. |
| 66 | B3b | OCH₃ | ethyl | H | 3-methoxycyclohexyl | trans; mp. 94° C. |
| 67 | B3b | OCH₃ | ethyl | H | 3-methoxycyclohexyl | cis; mp. 108° C. |
| 68 | B3b | OCH₃ | ethyl | H | 4-(methylethoxy-cyclohexyl | (A), mp. 820° C. |
| 69 | B3b | OCH₃ | ethyl | H | 4-[C(CH₃)₃]cyclohexyl | cis; mp. 92° C. |
| 70 | B3b | OCH₃ | ethyl | H | 4-[C(CH₃)₃]cyclohexyl | trans; mp. 108° C. |
| 71 | B3b | OCH₃ | ethyl | H | 4-methylcyclohexyl | (B), mp. 92° C. |
| 72 | B3b | OCH₃ | ethyl | H | 4-methylcyclohexyl | (A), mp. 80° C. |
| 2 | B2 | Cl | ethyl | H | CH₂—CH(CH₃)₂ | mp. 82° C. |
| 73 | B3b | Cl | ethyl | H | —CH₂—O—C₂H₅ | mp. 82° C. |
| 48 | B2 | H | methyl | H | cyclohexl | — |
| 74 | B4 | I | ethyl | H | 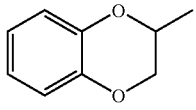 | — |
| 75 | B4 | I | ethyl | H | 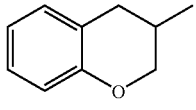 | mp. 124° C. |
| 76 | B4 | I | ethyl | H | 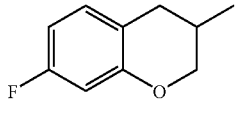 | mp. 138° C. |
| 77 | B4 | I | ethyl | H | 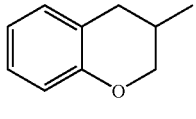 | mp. 120° C. |
| 78 | B4 | CN | ethyl | H | 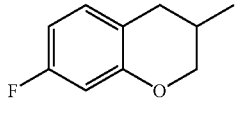 | mp. 128° C. |
| 79 | B4 | CN | ethyl | H |  | mp. 136° C. |

TABLE 1-continued

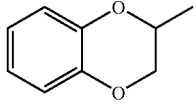

| Co. no. | Ex. no. | R² | R³ | R⁴ | R¹ | physical data |
|---|---|---|---|---|---|---|
| 80 | B4 | CN | ethyl | H | 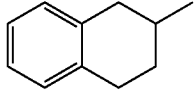 | mp. 120° C. |
| 81 | B4 | CN | ethyl | H | 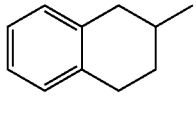 | mp. 139° C. |
| 82 | B4 | methyl | ethyl | H | 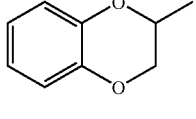 | mp. 106° C. |
| 83 | B4 | methyl | ethyl | H | 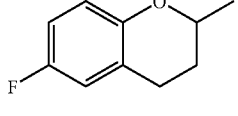 | mp. 149° C. |
| 84 | B4 | methyl | ethyl | H |  | mp. 118° C. |
| 85 | B4 | methyl | ethyl | H | 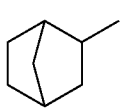 | mp. 180° C. |
| 86 | B4 | methyl | ethyl | H | phenylethyl | mp. 53° C. |
| 87 | B4 | methyl | ethyl | H | 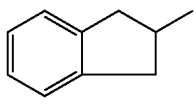 | mp. 87° C. |
| 88 | B4 | methyl | ethyl | H | —CH₂—CH(CH₃)₂ | mp. 68° C. |
| 89 | B4 | methyl | ethyl | H | | mp. 120° C. |
| 31 | B4 | 3-thiazolyl | ethyl | H | 4-methoxycyclohexyl | cis; 113° C. |
| 90 | B3b | OCH₃ | H | H | 4-methoxycyclohexyl | trans, mp. 126° C. |
| 91 | B3b | OCH₃ | H | H | 4-methoxycyclohexyl | cis, mp. 100° C. |
| 92 | B3b | OCH₃ | H | CH₃ | 4-methoxycyclohexyl | cis; mp. 120° C. |
| 93 | B3b | OCH₃ | H | CH₃ | 4-methoxycyclohexyl | trans, mp. 111° C. |
| 94 | B3b | OCH₃ | methyl | H | 4-methoxycyclohexyl | cis, mp. 96° C. |
| 95 | B3b | OCH₃ | phenyl | H | 4-methoxycyclohexyl | cis; HCl (1:1), mp. 138° C. |
| 96 | B3b | OCH₃ | propyl | H | 4-methoxycyclohexyl | trans; mp. 118° C. |
| 97 | B3b | OCH₃ | propyl | H | 4-methoxycyclohexyl | cis; |

TABLE 1-continued

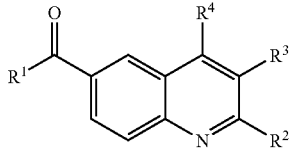

| Co. no. | Ex. no. | R² | R³ | R⁴ | R¹ | physical data |
|---|---|---|---|---|---|---|
| 98 | B3b | OCH₃ | methyl | H | 4-methoxycyclohexyl | mp. 108° C. cis; mp. 104° C. |
| 99 | B4 | N(CH₃)₂ | ethyl | H | 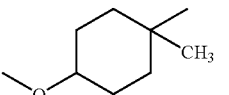 | (B); mp. 102° C. |
| 100 | B3b | Cl | ethyl | H | 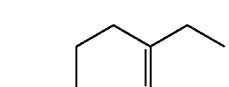 | mp. 114° C. |
| 101 | B4 | methyl | ethyl | H | 4-butoxycyclohexyl | cis; mp. 86° C. |
| 102 | B3b | Cl | ethyl | H | 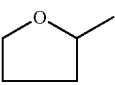 | mp. 78° C. |
| 103 | B3b | Cl | ethyl | H | 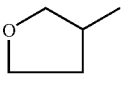 | mp. 91° C. |
| 104 | B4 | N(CH₃)₂ | ethyl | H | 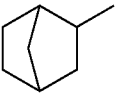 | mp. 103° C. |
| 105 | B4 | N(CH₃)₂ | ethyl | H | 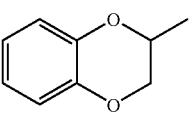 | mp. 170° C. |
| 106 | B3b | Cl | ethyl | H | 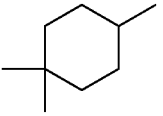 | mp. 137° C. |
| 107 | B3b | Cl | ethyl | H | 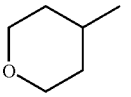 | mp. 137° C. |
| 108 | B4 | methyl | ethyl | ethyl | 4-methoxycyclohexyl | cis; mp. 91° C. |
| 109 | B4 | methyl | ethyl | H | 4-ethoxycyclohexyl | trans; mp. 150° C. |
| 110 | B4 | methyl | ethyl | H | 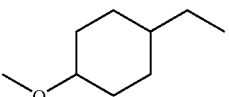 | mp. 90° C. |
| 111 | B4 | methyl | ethyl | H | 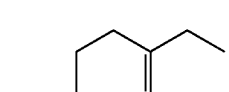 | mp. 94° C. |

TABLE 1-continued

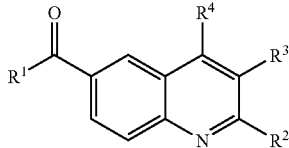

| Co. no. | Ex. no. | R² | R³ | R⁴ | R¹ | physical data |
|---|---|---|---|---|---|---|
| 112 | B4 | methyl | ethyl | H | 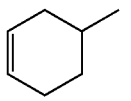 | mp. 176° C. |
| 113 | B4 | methyl | ethyl | H | 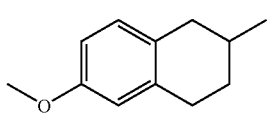 | mp. 106° C. |
| 114 | B4 | propyl | H | H | 4-methoxycyclohexyl | cis; mp. 74° C. |
| 115 | B4 | methyl | ethyl | H | 4-ethoxycyclohexyl | cis; mp. 108° C. |
| 116 | B4 | methyl | ethyl | H | 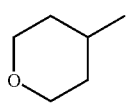 | mp. 110° C. |
| 117 | B3b | Cl | ethyl | H | 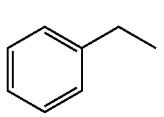 | mp. 124° C. |
| 118 | B3b | Cl | ethyl | H | 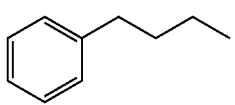 | mp. 107° C. |
| 119 | B3b | Cl | ethyl | H | 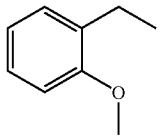 | mp. 129° C. |
| 120 | B4 | methyl | ethyl | H | 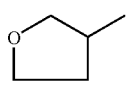 | mp. 106° C. |
| 41 | B3b | Cl | ethyl | H | 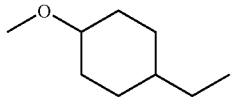 | trans; mp. 157° C. |
| 182 | B3b | methyl | ethyl | H | 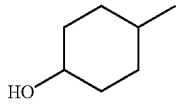 | cis; mp. 170° C. |
| 183 | B3b | methyl | ethyl | H | 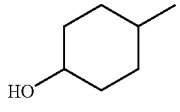 | trans; mp. 144° C. |
| 184 | B3b | methyl | ethyl | H | 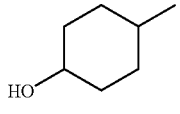 | mp. 138° C. |

TABLE 1-continued
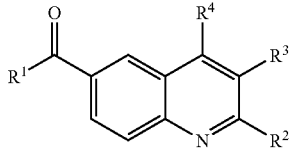
| Co. no. | Ex. no. | R² | R³ | R⁴ | R¹ | physical data |
|---|---|---|---|---|---|---|
| 185 | B3b | Cl | ethyl | H | 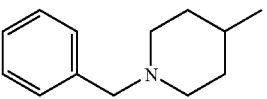 | mp. 120° C. |
| 186 | B3b | Cl | ethyl | H | 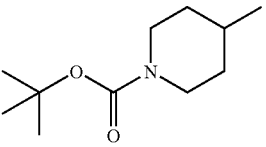 | |
| 187 | B3b | methyl | ethyl | H | 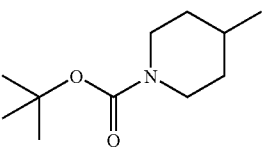 | mp. 162° C. |
| 216 | B4 | C≡N | ethyl | H | 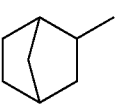 | mp.: 160° C. |
| 217 | B4 | methyl | ethyl | H | 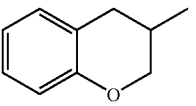 | .ethanedioate (1:1); mp.: 143° C. |
| 218 | B4 | I | ethyl | H | 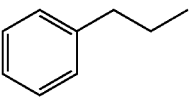 | mp.: 102° C. |
| 219 | B4 | C≡N | ethyl | H | 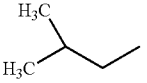 | mp.: 115° C. |
| 220 | B4 | Cl | ethyl | H | 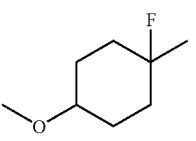 | (A); mp.: 107° C. |
| 221 | B4 | Cl | ethyl | H | 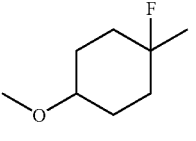 | (B); mp.: 113° C. |
| 222 | B4 | I | ethyl | H |  | mp.: 206° C. |
| 223 | B4 | Cl | ethyl | H | 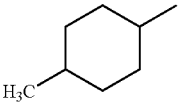 | (trans); mp.;117° C. |

TABLE 1-continued

| Co. no. | Ex. no. | R² | R³ | R⁴ | R¹ | physical data |
|---|---|---|---|---|---|---|
| 224 | B4 | methyl | ethyl | H | 4-methoxy-1-fluoro-1-methylcyclohexyl (H₃CO, F, CH₃) | (A); mp. 103° C. |
| 225 | B2 | Cl | ethyl | H | 4-methylcyclohex-3-enyl | mp.: 94° C. |
| 226 | B3b | Cl | ethyl | H | 4-ethoxy-1-methylcyclohexyl (C₂H₅O) | (trans); mp.: 157° C. |
| 227 | B3c | methoxy | 4-ethylmorpholine | H | 4-methoxy-1-methylcyclohexyl (H₃CO) | mp.: 204° C. |
| 228 | B4 | Cl | ethyl | H | 4-methoxy-1-methylcyclohexyl (H₃CO) | (A); mp.: 136° C. |
| 229 | B3b | n-propyl | H | H | 4-methoxy-1-methylcyclohexyl (H₃CO) | (trans);.HCl (1:1); mp.:150° C. |
| 230 | B3b | Cl | ethyl | H | 5-methoxy-1,2,3,4-tetrahydronaphth-2-yl (OCH₃) | mp.: 116° C. |
| 231 | B3b | Cl | ethyl | H | 3-ethylchroman-3-yl | mp.: 120° C. |
| 232 | B3b | Cl | ethyl | H | 1,2,3,4-tetrahydronaphth-1-yl | mp.: 112° C. |
| 233 | B10 | i-propyl | H | C(=O)O—C₂H₅ | 4-methoxy-1-methylcyclohexyl (H₃CO) | (cis); mp.: 91° C. |

TABLE 1-continued
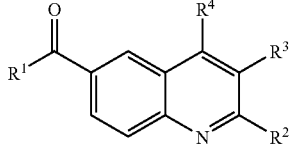
| Co. no. | Ex. no. | R² | R³ | R⁴ | R¹ | physical data |
|---|---|---|---|---|---|---|
| 234 | B4 | methyl | ethyl | H | 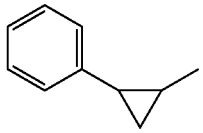 | mp.: 122° C. |
| 235 | B4 | methyl | ethyl | H | 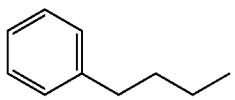 | mp.: 106° C. |
| 236 | B4 | methyl | ethyl | H | 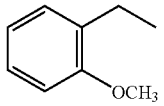 | mp.: 104° C. |
| 237 | B4 | methyl | ethyl | H | 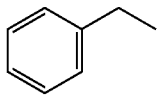 | mp.: 90° C. |
| 238 | B4 | methyl | H | H | 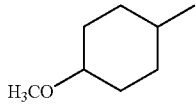 | (cis); mp.: 80° C. |
| 239 | B3b | Cl | ethyl | H | 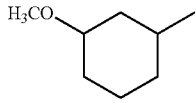 | (trans); mp.: 126° C. |
| 240 | B3b | Cl | ethyl | H | 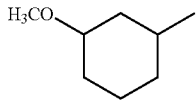 | (cis); mp.: 128° C. |
| 241 | B4 | methyl | ethyl | H | 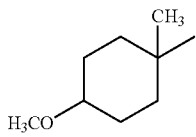 | (A); mp.: 90° C. |
| 242 | B4 | methyl | ethyl | H | 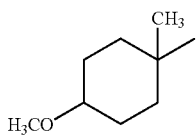 | (B); mp.: 110° C. |
| 243 | B3b | Cl | ethyl | H | 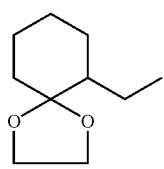 | mp.: 134° C. |

TABLE 1-continued

| Co. no. | Ex. no. | R² | R³ | R⁴ | R¹ | physical data |
|---|---|---|---|---|---|---|
| 244 | B3b | Cl | ethyl | H | norbornyl-ethyl | mp.: 127° C. |
| 245 | B4 | NHC(=O)NH₂ | ethyl | H | 4-methoxy-cyclohexyl-methyl | (cis); mp.: 176° C. |
| 246 | B4 | methyl | ethyl | H | 4-methyl-cyclohexyl-methyl | (B) |
| 247 | B3b | Cl | ethyl | H | tetrahydropyran-3-yl-methyl | mp.: 92° C. |
| 248 | B4 | methyl | ethyl | H | 4-methyl-cyclohexyl-methyl | (A); mp.: 80° C. |
| 249 | B3b | Cl | ethyl | H | norbornyl-methyl | (B); mp.: 138° C. |
| 250 | B4 | methyl | ethyl | H | 4-n-propoxy-cyclohexyl-methyl | (trans); mp.: 118° C. |
| 251 | B4 | methyl | ethyl | H | norbornyl-methyl | (B);.HCl (1:1) |
| 252 | B3b | Cl | ethyl | H | 4-isopropyl-cyclohexyl-methyl | (A) |
| 253 | B3b | Cl | ethyl | H | 4-isopropyl-cyclohexyl-methyl | (B) |
| 254 | B3b | methyl | ethyl | H | phenyl-(CH₂)₄- | mp.: 74° C. |

TABLE 1-continued
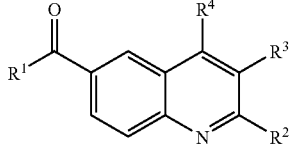
| Co. no. | Ex. no. | R² | R³ | R⁴ | R¹ | physical data |
|---|---|---|---|---|---|---|
| 255 | B4 | methyl | ethyl | H | 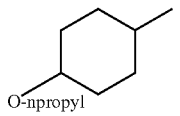 | (cis); mp.: 68° C. |
| 256 | B4 | methyl | ethyl | H | 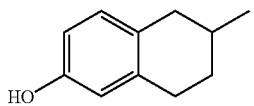 | mp.: 210° C. |
| 257 | B4 | methyl | ethyl | H | 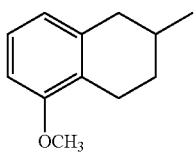 | mp.: 113° C. |
| 258 | B4 | methyl | ethyl | H | 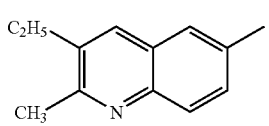 | mp.: 92° C. |
| 259 | B3b | methyl | ethyl | H | 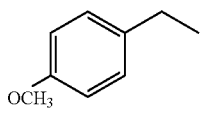 | mp.: 115° C. |
| 260 | B3b | methyl | ethyl | H | 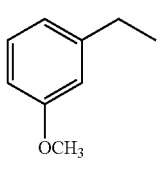 | mp.: 60° C. |
| 261 | B3b | Cl | ethyl | H | 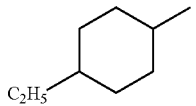 | (A); mp.: 86° C. |
| 262 | B3b | Cl | ethyl | H | 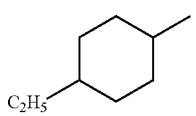 | (B); mp.: 101° C. |
| 263 | B3b | methyl | ethyl | H | 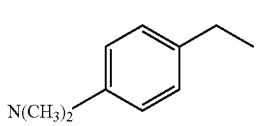 | mp.: 130° C. |
| 264 | B3b | Cl | ethyl | H | 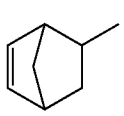 | (A); mp.: 124° C. |

TABLE 1-continued

| Co. no. | Ex. no. | R² | R³ | R⁴ | R¹ | physical data |
|---|---|---|---|---|---|---|
| 265 | B3b | Cl | ethyl | H | norbornenyl | (B); mp.: 126° C. |
| 266 | B4 | N(CH₃)₂ | ethyl | H | 3-methoxycyclohexyl | (trans), mp.: 102° C. |
| 267 | B4 | N(CH₃)₂ | ethyl | H | 3-methoxycyclohexyl | (cis);.HCl (1:1); mp.: 170° C. |
| 268 | B4 | methyl | ethyl | H | norbornyl | (A);.HCl (1:1); mp.: 206° C. |
| 269 | B4 | methyl | ethyl | H | 1,2,3,4-tetrahydronaphthalen-1-yl | mp.: 104° C. |
| 270 | B3b | methyl | ethyl | H | 1,1-diphenylethyl | mp.: 117° C. |
| 271 | B4 | NCH₂H₅OCH₃ | ethyl | H | benzyl (CH(CH₃)Ph) | — |
| 272 | B4 | methyl | ethyl | H | 1-(2-methoxyethyl)-4-methylpiperidinyl | — |
| 273 | B4 | NH₂ | ethyl | H | phenethyl | — |
| 274 | B3b | Cl | ethyl | H | 3,4-difluorobenzyl (ethyl) | — |

TABLE 1-continued
| Co. no. | Ex. no. | R² | R³ | R⁴ | R¹ | physical data |
|---|---|---|---|---|---|---|
| 275 | B3b | Cl | ethyl | H | 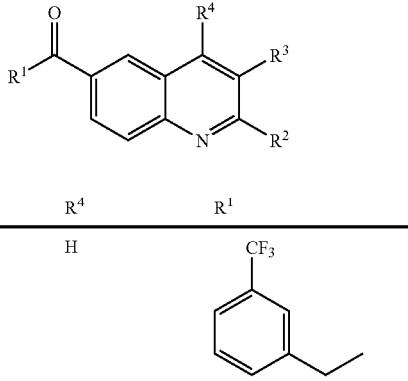 | mp.: 99° C. |
| 276 | B3b | Cl | ethyl | H | 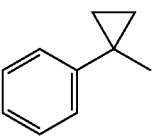 | mp.: 95° C. |
| 277 | B4 | methyl | ethyl | H | 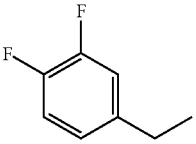 | mp.: 105° C. |
| 278 | B3b | Cl | ethyl | H | 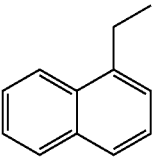 | mp.: 141° C. |
| 279 | B4 | Cl | ethyl | H | 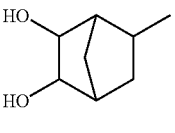 | mp.: 168° C. |
| 280 | B4 | Cl | ethyl | H | 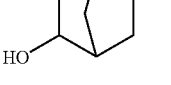 | — |
| 281 | B4 | Cl | ethyl | H | 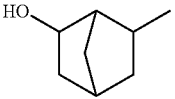 | mp.: 140° C. |
| 282 | B4 | Cl | ethyl | H | 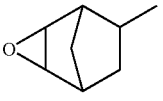 | mp.: 169° C. |
| 283 | B4 | methyl | ethyl | H | 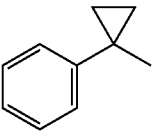 | mp.: 96° C. |
| 284 | B3b | Cl | CH₂N(CH₃)₂ | H | 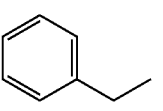 | mp.: 115° C. |

TABLE 1-continued
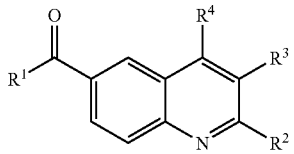
| Co. no. | Ex. no. | R² | R³ | R⁴ | R¹ | physical data |
|---|---|---|---|---|---|---|
| 285 | B4 | methyl | ethyl | H | 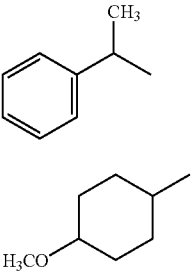 | mp.: 133° C. |
| 286 | B4 | methyl | CH₂OCH₃ | H | 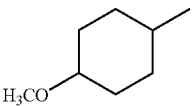 | (trans); mp.: 106° C. |
| 287 | B4 | methyl | CH₂N(CH₃)₂ | H | 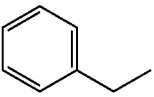 | (cis); mp.: 110° C. |
| 288 | B3b | Cl | n-propyl | H | 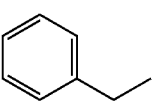 | mp.: 110° C. |
| 289 | B4 | NH₂ | ethyl | H | 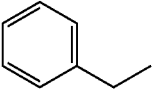 | mp.: 218° C. |
| 290 | B4 | methyl | n-propyl | H | 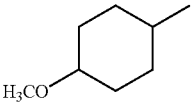 | mp.: 90° C. |
| 291 | B3b | Cl | n-propyl | H | 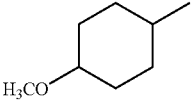 | (cis); mp.: 128° C. |
| 292 | B3b | Cl | n-propyl | H | 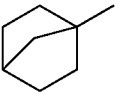 | (trans); mp.: 104° C. |
| 293 | B3b | Cl | ethyl | H | 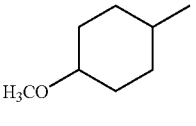 | mp.:106° C. |
| 294 | B4 | methyl | n-propyl | H | 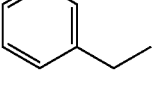 | (cis); mp.: 94° C. |
| 295 | B4 | methyl | CH₂N(CH₃)₂ | H |  | mp.: 83° C. |

TABLE 1-continued
| Co. no. | Ex. no. | R² | R³ | R⁴ | R¹ | physical data |
|---|---|---|---|---|---|---|
| 296 | B3b | Cl | ethyl | H |  | mp.: 99° C. |
| 297 | B3b | Cl | ethyl | H | 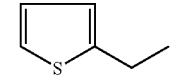 | mp.: 110° C. |
| 298 | B4 | methyl | ethyl | H | 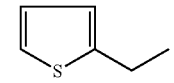 | mp.: 93° C. |
| 299 | B4 | methyl | ethyl | H | 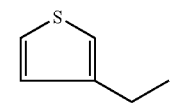 | mp.: 105° C. |
| 300 | B4 | methyl | ethyl | H |  | mp.: 114° C. |
| 301 | B3b | methyl | ethyl | H | 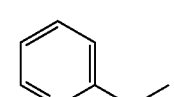 | mp.: 143° C. |
| 302 | B4 | methoxy | ethyl | H | 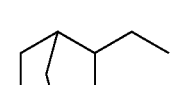 | mp.: 93° C. |
| 303 | B4 | methyl | ethyl | H | 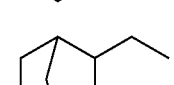 | mp.: 82° C. |
| 304 | B4 | n-butyl | ethyl | H | 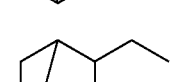 | — |
| 305 | B3b | Cl | n-propyl | H | 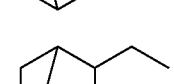 | mp.: 125° C. |
| 306 | B1 | methyl | C(=O)OC₂H₅ | H | 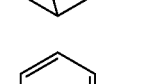 | mp.: 136° C. |
| 307 | B4 | methyl | n-propyl | H | 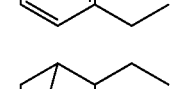 | mp.: 81° C. |

TABLE 1-continued
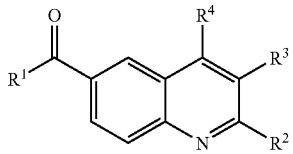
| Co. no. | Ex. no. | R² | R³ | R⁴ | R¹ | physical data |
|---|---|---|---|---|---|---|
| 308 | B4 | methoxy | n-propyl | H | 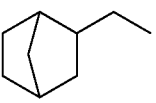 | mp.: 80° C. |
| 309 | B4 | I | n-propyl | H | 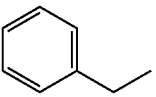 | mp.: 120° C. |
| 310 | B3d | methyl | ethyl | H | 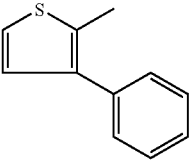 | .HCl(1:1); mp.: 129° C. |
| 311 | B3b | Cl | H | H | 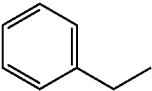 | mp.: 160° C. |
| 312 | B3b | Cl | H | H | 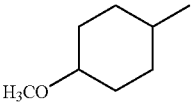 | (trans); mp.: 145° C. |
| 313 | B3b | Cl | H | H | 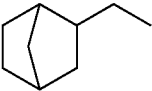 | mp.: 103° C. |
| 314 | B4 | n-propyl | n-propyl | H | 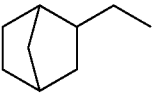 | .HCl (1:1); mp.: 150° C. |
| 315 | B4 | n-propyl | ethyl | H | 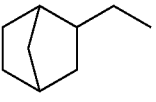 | .HCl (1:1) |
| 316 | B4 | n-propyl | H | H | 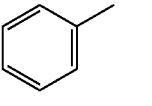 | .HCl (1:1); mp.: 140° C. |
| 317 | B3b | Cl | H | H | 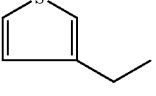 | mp.: 168° C. |
| 318 | B4 | methyl | n-propyl | H | 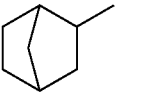 | .HCl (1:1); mp.: 200° C. |

TABLE 1-continued
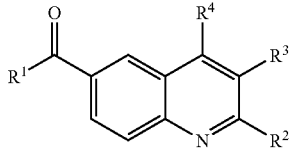
| Co. no. | Ex. no. | R² | R³ | R⁴ | R¹ | physical data |
|---|---|---|---|---|---|---|
| 509 | B3b | Cl | ethyl | H | 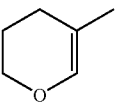 | — |
| 510 | B4 | methyl | ethyl | H | 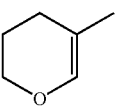 | .H₂O (1:1) |
| 513 | B4 | methyl | ethyl | H | 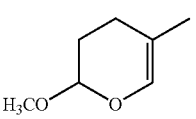 | — |
| 516 | B4 | Cl | ethyl | H | 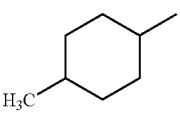 | mp.: 120° C. |
| 517 | B4 | I | ethyl | H | CH₂CH(CH₃)₂ | — |
| 518 | B4 | Cl | ethyl | H |  | — |
| 519 | B4 | Cl | ethyl | H | 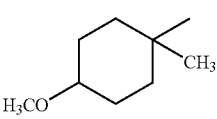 | (A + B) |
| 521 | B4 | I | ethyl | H | 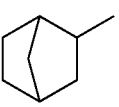 | — |
| 522 | B4 | methyl | ethyl | H | 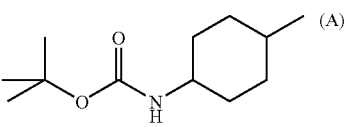 | (A) |
| 1 | B4 | methyl | ethyl | H | 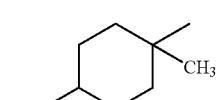 | (A) |
| 525 | B4 | Cl | ethyl | H | 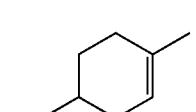 | — |
| 527 | B4 | F | ethyl | H | 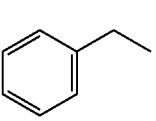 | mp.: 116° C. |

TABLE 2

Structure: 4-methoxycyclohexyl-C(=X)-quinoline with 3-CH₂-CH₃ and 2-R²

| Co. no. | Ex. no. | R² | X | physical data |
|---|---|---|---|---|
| 5 | B3b | Cl | O | trans; mp. 120° C. |
| 121 | B3b | 1-piperidinyl | O | cis; HCl (1:1) |
| 122 | B3b | 1-piperidinyl | O | trans; HCl (1:1); mp. 128° C. |
| 123 | B3b | 4-thiomorpholinyl | O | cis; mp. 105° C. |
| 124 | B3b | 4-thiomorpholinyl | O | trans; mp. 115° C. |
| 125 | B3b | 4-morpholinyl | O | trans; mp. 118° C. |
| 126 | B3b | 4-morpholinyl | O | cis; mp. 118° C. |
| 127 | B3b | —N(CH₃)₂ | O | trans; mp. 96° C. |
| 128 | B3b | —N(CH₃)₂ | O | cis; mp. 114° C. |
| 4 | B3b | Cl | O | cis; mp. 123° C. |
| 8 | B3c | OCH₃ | O | trans, mp. 68° C. |
| 7 | B3c | OCH₃ | O | cis; mp. 116° C. |
| 6 | B4 | acetyl | O | trans; mp. 108° C. |
| 129 | B4 | acetyl | O | cis; mp. 106° C. |
| 11 | B4 | NH—(CH₂)₂—OCH₃ | O | trans; mp. 107° C. |
| 10 | B4 | NH—(CH₂)₂—OCH₃ | O | cis; mp. 115° C. |
| 12 | B4 | NH—(CH₂)₂—SCH₃ | O | cis; mp. 120° C. |
| 13 | B4 | NH—(CH₂)₂—SCH₃ | O | trans; mp. 125° C. |
| 14 | B4 | —C≡C—Si(CH₃)₃ | O | cis; mp. 114° C. |
| 16 | B4 | —C≡C—Si(CH₃)₃ | O | trans; mp. 108° C. |
| 15 | B4 | —C≡CH | O | cis; mp. 132-133° C. |
| 17 | B4 | —C≡CH | O | trans; mp. 128° C. |
| 18 | B4 | —C≡C—CH₂OH | O | cis; mp. 113° C. |
| 130 | B4 | —C≡C—CH₂OH | O | trans; mp. 108° C. |
| 19 | B4 | F | O | cis; mp. 92-99° C. |
| 20 | B4 | F | O | trans; mp. 114° C. |
| 21 | B4 | I | O | mp. 110° C. |
| 22 | B4 | CN | O | cis; mp. 137-138° C. |
| 26 | B4 | H | O | trans |
| 23 | B4 | —C(=O)—OCH₃ | O | cis; mp. 91° C. |
| 24 | B4 | —C(=O)—OCH₃ | O | trans; mp. 99° C. |
| 25 | B4 | H | O | cis; mp. 88° C. |
| 27 | B4 | methyl | O | cis; mp. 110-112° C. |
| 131 | B4 | methyl | O | trans; mp. 25° C. |
| 28 | B4 | ethenyl | O | cis; mp. 108° C. |
| 132 | B4 | ethenyl | O | trans; mp. 103° C. |
| 29 | B4 | phenyl | O | trans; mp. 112° C. |
| 30 | B4 | 2-thienyl | O | cis; mp. 142° C. |
| 133 | B4 | 2-thiazolyl | O | cis; 108° C. |
| 134 | B4 | 2-furanyl | O | cis; mp. 105° C. |
| 51 | B8a | OCH₃ | N—OH | [1α(A), 4α]; mp. 133° C. |
| 52 | B8a | OCH₃ | N—OH | [1α(B), 4α]; mp. 142° C. |
| 53 | B8b | OCH₃ | NNH₂ | [1α(Z), 4α]; mp. 110° C. |
| 135 | B4 | NH₂ | O | cis; mp. 203° C. |
| 136 | B4 | NH₂ | O | trans; mp. 202° C. |
| 137 | B4 | —C(=O)—OCH(CH₃)₂ | O | cis; mp. 105° C. |
| 138 | B4 | —C(=O)—OCH(CH₃)₂ | O | trans; mp. 88° C. |
| 38 | B4 | SCH₃ | O | cis; mp. 124° C. |
| 39 | B4 | SCH₃ | O | trans; mp. 116° C. |
| 32 | B4 | CH₃C(=O)NH-CH₂-C(=O)-OCH₃ | O | cis; mp. 130° C. |
| 139 | B4 | ethyl | O | cis; mp.180° C. |
| 188 | B4 | NH₂ | O | cis + trans |

TABLE 2-continued
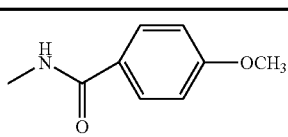
| Co. no. | Ex. no. | R² | X | physical data |
|---|---|---|---|---|
| 189 | B4 | 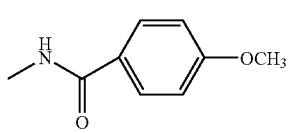 | O | cis; mp. 154° C. |
| 190 | B4 | 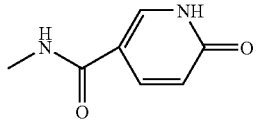 | O | trans; mp. 156° C. |
| 191 | B4 | 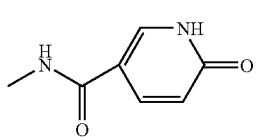 | O | cis; mp. >260° C. |
| 192 | B4 | 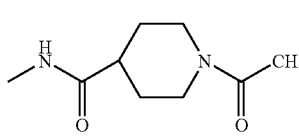 | O | .H₂O (1:1); trans; mp. 248° C. |
| 193 | B4 | 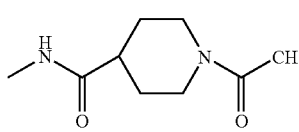 | O | cis; mp. 224° C. |
| 194 | B4 | 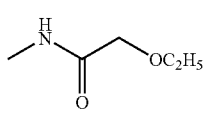 | O | trans; mp. 234° C. |
| 195 | B4 | 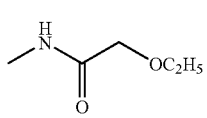 | O | cis; mp. 108° C. |
| 196 | B4 | 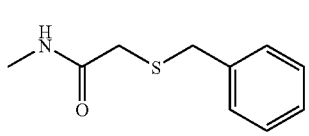 | O | trans; mp. 127° C. |
| 197 | B4 | 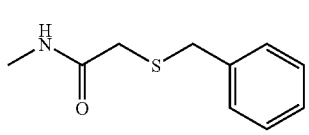 | O | cis; mp. 150° C. |
| 198 | B4 | | O | trans; mp. 90° C. |

TABLE 2-continued

| Co. no. | Ex. no. | R² | X | physical data |
|---|---|---|---|---|
| 199 | B4 | (N-methylamide of adamantane-1-carboxamide) | O | LC/MS [M + H]⁺; 475.4 |
| 200 | B4 | (N-methyl 2-(pyridin-4-ylthio)acetamide) | O | LC/MS [M + H]⁺; 464.3 |
| 201 | B4 | (N-methyl 2-(3-phenoxyphenyl)acetamide) | O | LC/MS [M + H]⁺; 523.3 |
| 202 | B4 | (N-methyl 4-(thiophen-2-yl)butanamide) | O | LC/MS [M + H]⁺; 465.3 |
| 203 | B4 | (N-methyl 4-ethoxybenzamide) | O | LC/MS [M + H]⁺; 475.4 |
| 204 | B4 | (N-methyl 2-(pyrimidin-2-ylthio)acetamide) | O | LC/MS [M + H]⁺; 465.3 |
| 205 | B4 | (N-methyl 2-phenylacetamide) | O | — |
| 319 | B4 | (phenethyl) | O | (cis); .ethanedioate (1:1); mp.: 160° C. |
| 320 | B4 | (phenylethynyl) | O | (cis); mp.: 150° C. |
| 321 | B4 | methoxy | CH₂ | (cis); .HCl (1:1); mp.:118° C. |
| 322 | B4 | n-butyl | O | (cis); .HCl (1:1); mp.:158° C. |

TABLE 2-continued
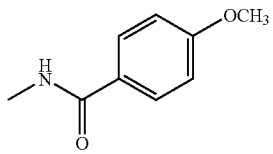
| Co. no. | Ex. no. | R² | X | physical data |
|---|---|---|---|---|
| 323 | B4 | 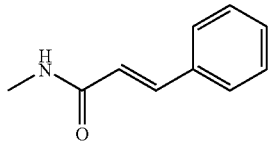 | O | — |
| 324 | B4 | 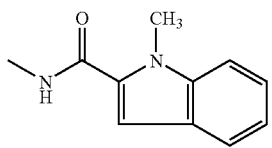 | O | — |
| 325 | B4 | 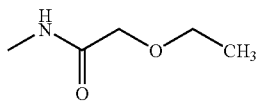 | O | — |
| 326 | B4 | 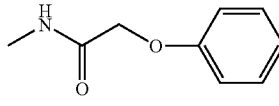 | O | — |
| 327 | B4 | 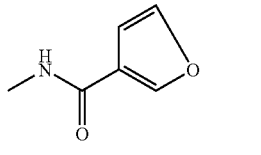 | O | — |
| 328 | B4 | 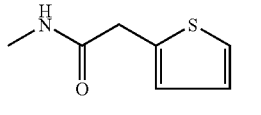 | O | — |
| 329 | B4 | 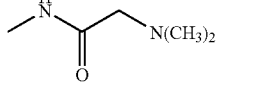 | O | — |
| 330 | B4 | 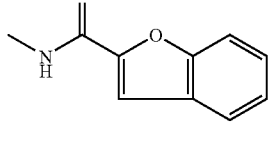 | O | — |
| 331 | B4 | 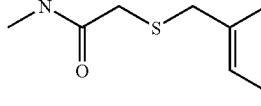 | O | — |
| 332 | B4 |  | O | — |

TABLE 2-continued

| Co. no. | Ex. no. | R² | X | physical data |
|---|---|---|---|---|
| 333 | B4 | N-methyl 1-acetylpiperidine-4-carboxamide | O | — |
| 334 | B4 | N-methyl 6-oxo-1,6-dihydropyridine-3-carboxamide | O | — |
| 335 | B4 | N-methyl 5-methylpyrazine-2-carboxamide | O | — |
| 336 | B4 | N-methyl (E)-3-(furan-2-yl)acrylamide | O | — |
| 337 | B4 | N-methyl pyrazine-2-carboxamide | O | — |
| 338 | B4 | N-methyl 3-(methylthio)propanamide | O | — |
| 339 | B4 | N-methyl norbornane-2-carboxamide | O | — |
| 340 | B4 | N-methyl 3-methyl-1H-indene-2-carboxamide | O | — |

TABLE 2-continued
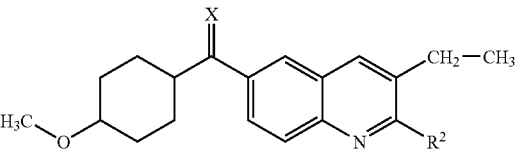
| Co. no. | Ex. no. | R² | X | physical data |
|---|---|---|---|---|
| 341 | B4 | 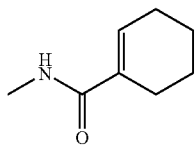 | O | — |
| 342 | B4 | 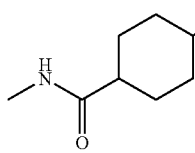 | O | — |
| 343 | B4 | 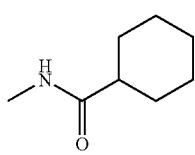 | O | — |
| 344 | B4 | 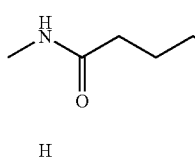 | O | — |
| 345 | B4 | 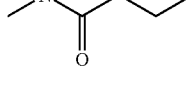 | O | — |
| 346 | B4 | 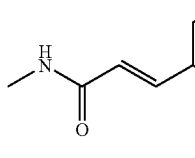 | O | — |
| 347 | B4 | 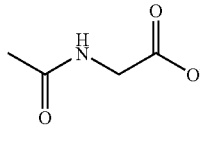 | O | — |
| 348 | B4 | CH₂OC(=O)CH₃ | O | (cis); mp.: 74° C. |
| 349 | B4 | 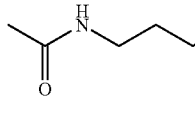 | O | — |
| 350 | B4 |  | O | — |

TABLE 2-continued
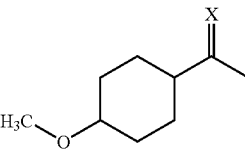
| Co. no. | Ex. no. | R² | X | physical data |
|---|---|---|---|---|
| 351 | B4 | 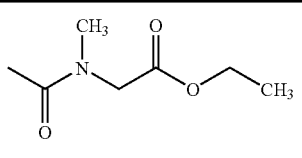 | O | — |
| 352 | B4 | 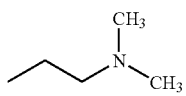 | O | — |
| 353 | B4 | 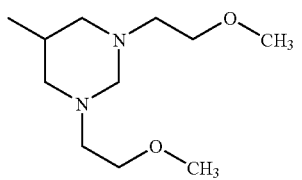 | O | (A); .HCl (1:2) .H2O (1:1); mp.: 166° C. |
| 354 | B4 | 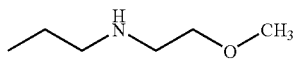 | O | (cis) |
| 355 | B4 | 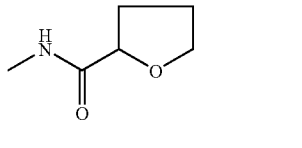 | O | — |
| 356 | B4 | 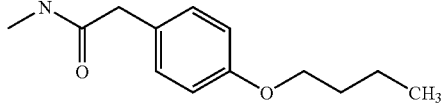 | O | — |
| 357 | B4 | 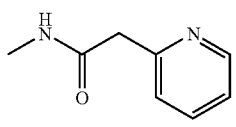 | O | — |
| 358 | B4 | 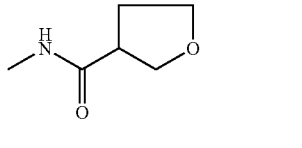 | O | — |
| 359 | B4 | 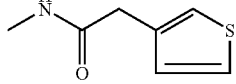 | O | — |
| 360 | B4 |  | O | — |

TABLE 2-continued
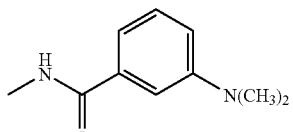
| Co. no. | Ex. no. | R² | X | physical data |
|---|---|---|---|---|
| 361 | B4 | 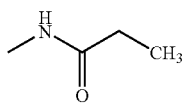 | O | — |
| 362 | B4 | 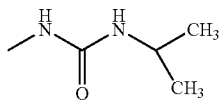 | O | — |
| 363 | B4 | 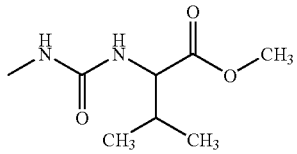 | O | — |
| 364 | B4 | 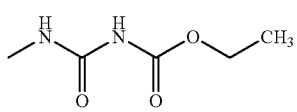 | O | — |
| 365 | B4 | 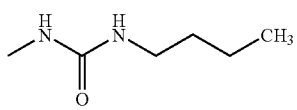 | O | — |
| 366 | B4 | 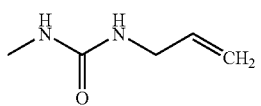 | O | — |
| 367 | B4 | 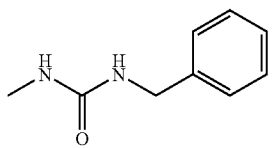 | O | — |
| 368 | B4 | 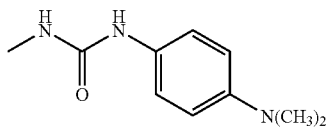 | O | — |
| 369 | B4 | 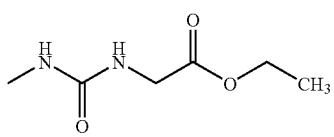 | O | — |
| 370 | B4 | | O | — |

TABLE 2-continued
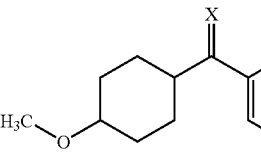
| Co. no. | Ex. no. | R² | X | physical data |
|---|---|---|---|---|
| 371 | B4 | 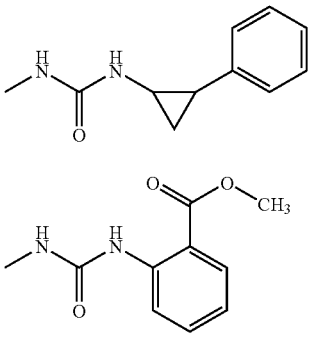 | O | — |
| 372 | B4 | 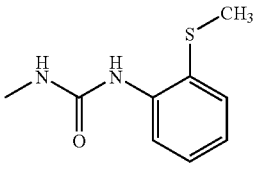 | O | — |
| 373 | B4 | 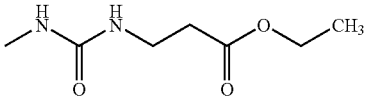 | O | — |
| 374 | B4 | 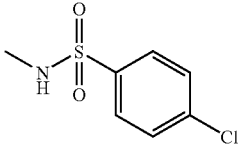 | O | — |
| 375 | B4 | 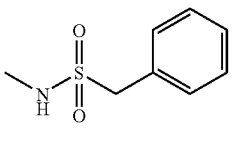 | O | — |
| 376 | B4 | 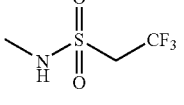 | O | — |
| 377 | B4 | 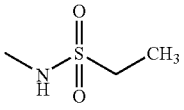 | O | — |
| 378 | B4 | 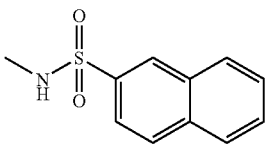 | O | — |
| 379 | B4 | | O | — |

TABLE 2-continued
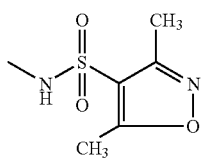
| Co. no. | Ex. no. | R² | X | physical data |
|---|---|---|---|---|
| 380 | B4 | 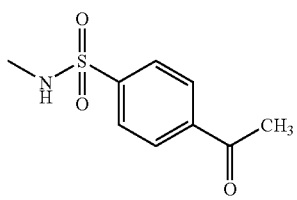 | O | — |
| 381 | B4 | 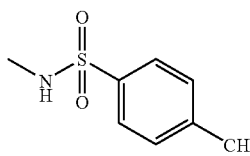 | O | — |
| 382 | B4 | 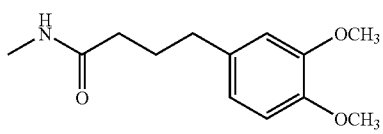 | O | — |
| 383 | B4 | 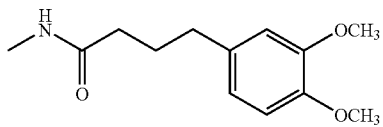 | O | (cia); mp.: 148° C. |
| 384 | B4 | 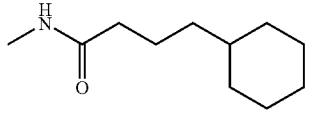 | O | (trans); mp.: 141° C. |
| 385 | B4 | 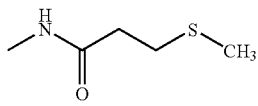 | O | mp.: 130° C. |
| 386 | B4 | 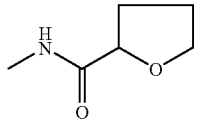 | O | (cia); mp.: 140° C. |
| 387 | B4 |  | O | (trans); mp.: 155° C. |

TABLE 3

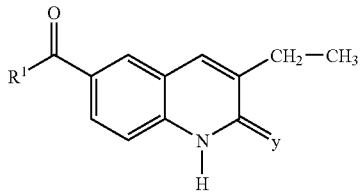

| Co. no. | Ex. no. | Y. | R¹ | physical data |
|---|---|---|---|---|
| 140 | B4 | O | 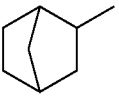 | mp. 220° C. |
| 141 | B4 | O | 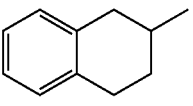 | mp. 213° C. |
| 142 | B4 | O | 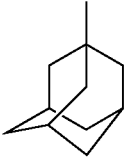 | mp. 148° C. |
| 143 | B4 | O | 1-methylcyclohexyl | mp. 195-210° C. |
| 144 | B4 | O | 3-methoxycyclohexyl | cis; mp. 156° C. |
| 145 | B4 | O | 3-methoxycyclohexyl | trans; mp. 156-163° C. |
| 146 | B4 | O | 4-(dimethylethyl)cyclohexyl | mp. 230° C. |
| 147 | B4 | O | 4-(methylethoxy)cyclohexyl | mp. 186° C. |
| 148 | B4 | O | 4-methylcyclohexy | trans; mp. 214° C. |
| 36 | B4 | S | 4-methoxycyclohexyl | cis; mp. 224° C. |
| 37 | B4 | S | 4-methoxycyclohexyl | trans; mp. 220° C. |
| 149 | B4 | O | 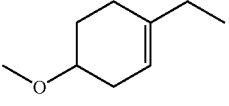 | mp. 188° C. |
| 40 | B4 | O | 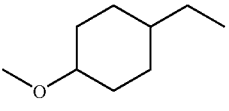 | mp. 192° C. |
| 150 | B4 | O | 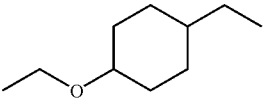 | cis; mp. 226° C. |
| 151 | B4 | O | 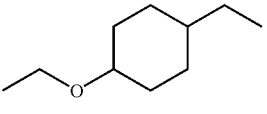 | trans; mp. 226° C. |
| 152 | B4 | O | 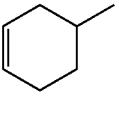 | mp. 213° C. |
| 153 | B4 | O | 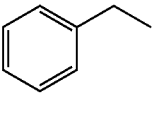 | mp. 200° C. |

TABLE 3-continued

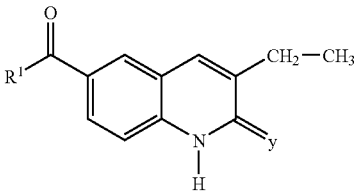

| Co. no. | Ex. no. | Y. | R¹ | physical data |
|---|---|---|---|---|
| 154 | B4 | O | 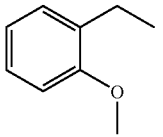 | mp. 210° C. |
| 155 | B4 | O | 4,4-dimethylcyclohexyl | mp. 242° C. |
| 388 | B4 | O | CH₂CH(CH₃)₂ | mp. 189° C. |
| 389 | B4 | O | 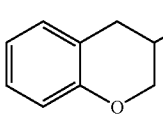 | mp. 228° C. |
| 390 | B4 | O | 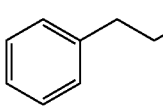 | mp. 197° C. |
| 391 | B4 | O | 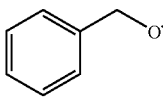 | mp. 145° C. |
| 392 | B4 | O | 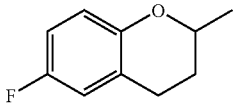 | mp. 192° C. |
| 393 | B4 | O | 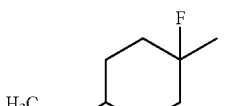 | (B); mp.: 224° C. |
| 394 | B4 | O | 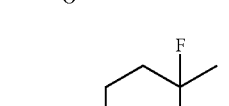 | (A); mp.: 201° C. |
| 395 | B4 | O | 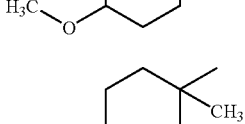 | (A); mp.: 207° C. |
| 396 | B4 | O | 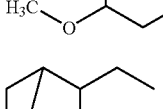 | mp.: 212° C. |
| 397 | B4 | O | 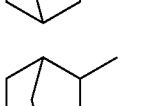 | (B); mp.: 238° C. |

TABLE 3-continued

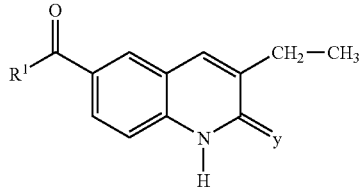

| Co. no. | Ex. no. | Y. | R[1] | physical data |
|---|---|---|---|---|
| 398 | B4 | O | 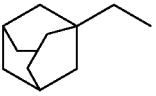 | mp.: 234° C. |
| 399 | B4 | O | 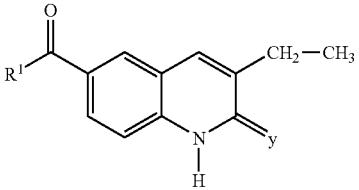 | (cis); mp.:192° C. |

TABLE 4

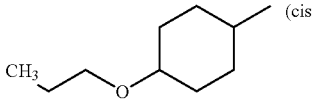

| Co. no. | Ex. no. | R[3] | R[4] | R[5] | R | physical data |
|---|---|---|---|---|---|---|
| 156 | B4 | ethyl | H | H | OCH$_3$ | trans; mp. 252° C. |
| 157 | B4 | H | H | H | OCH$_3$ | (cis + trans); mp. 244° C. |
| 158 | B4 | H | methyl | H | OCH$_3$ | cis; mp. >260° C. |
| 159 | B4 | methyl | H | H | OCH$_3$ | cis; mp. 254° C. |
| 160 | B4 | methyl | H | H | OCH$_3$ | trans; mp.>260° C. |
| 161 | B4 | propyl | H | H | OCH$_3$ | mp. 208° C. |
| 162 | B4 | propyl | H | H | OCH$_3$ | trans; mp. 232° C. |
| 9 | B4 | ethyl | H | H | OCH$_3$ | cis; mp. 224-226° C. |
| 43 | B5 | ethyl | H | CH$_3$ | OCH$_3$ | trans; mp. 116° C. |
| 42 | B5 | ethyl | H | CH$_3$ | OCH$_3$ | cis; mp. 125° C. |
| 44 | B6 | ethyl | H | CH$_2$—COOC$_2$H5 | OCH$_3$ | cis; mp. 152° C. |
| 45 | B4 | ethyl | H | CH$_2$—COOC$_2$H5 | OCH$_3$ | trans; mp. 147° C. |
| 46 | B4 | ethyl | H | benzyl | OCH$_3$ | cis; mp.137° C. |
| 47 | B4 | ethyl | H | benzyl | OCH$_3$ | trans; mp. 130° C. |
| 50 | B7 | methyl | H | H | H | mp. 256.1° C. |
| 163 | B4 | ethyl | ethyl | H | OCH$_3$ | cis; mp. 221° C. |
| 164 | B4 | ethyl | ethyl | H | OCH$_3$ | cis; mp. 221° C. |
| 165 | B4 | ethyl | ethyl | H | OCH$_3$ | trans; mp.215° C. |
| 166 | B4 | ethyl | H | 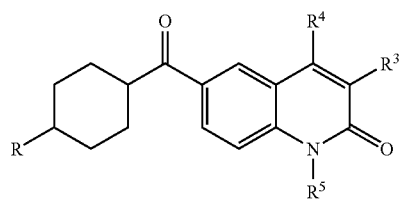 | OCH$_3$ | LC/MS [M + H]$^+$; 429.4 |
| 167 | B4 | ethyl | H | 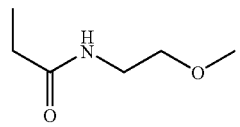 | OCH$_3$ | LC/MS [M + H]$^+$; 451.3 |
| 168 | B4 | H | H | H | OCH$_3$ | cis; mp. 106° C. |
| 169 | B4 | ethyl | H | 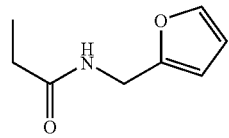 | OCH$_3$ | LC/MS [M + H]$^+$; 409.3 |

TABLE 4-continued

| Co. no. | Ex. no. | R³ | R⁴ | R⁵ | R | physical data |
|---|---|---|---|---|---|---|
| 400 | B9 | ethyl | H | propanoyl-NH-CH₂-C(O)-O-ethyl | OCH₃ | — |
| 401 | B9 | ethyl | H | propanoyl-NH-(CH₂)₃-(2-oxopyrrolidin-1-yl) | OCH₃ | — |
| 402 | B9 | ethyl | H | propanoyl-NH-(1-benzylpiperidin-4-yl) | OCH₃ | — |
| 403 | B9 | ethyl | H | propanoyl-NH-CH₂CH₂-S-CH₂-phenyl | OCH₃ | — |
| 404 | B9 | ethyl | H | propanoyl-NH-CH₂CH₂-(pyridin-2-yl) | OCH₃ | — |
| 405 | B9 | ethyl | H | propanoyl-NH-CH₂CH₂-(1-methylpyrrol-2-yl) | OCH₃ | — |
| 406 | B4 | ethyl | H | propanoyl-NH-cyclohexyl | OCH₃ | — |
| 407 | B4 | ethyl | H | propanoyl-NH-(2-oxotetrahydrothiophen-3-yl) | OCH₃ | — |
| 408 | B4 | ethyl | H | propanoyl-NH-cyclopropyl | OCH₃ | — |

TABLE 4-continued

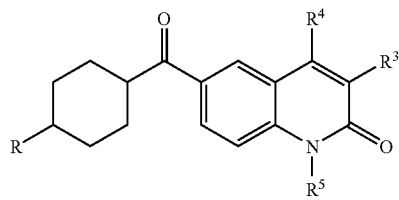

| Co. no. | Ex. no. | R³ | R⁴ | R⁵ | R | physical data |
|---|---|---|---|---|---|---|
| 409 | B3b | (CH₂)₃-piperidinyl | H | H | OCH₃ | mp.: 168° C. |
| 410 | B4 | CH₂OCH₃ | H | H | OCH₃ | mp.: 194° C. |
| 508 | B4 | ethyl | H | -C(=O)NH-CH₂CH₂CH₂-OC₂H₅ | OCH₃ | — |
| 520 | B9 | ethyl | H | -C(=O)NH-adamantyl | OCH₃ | — |

TABLE 5

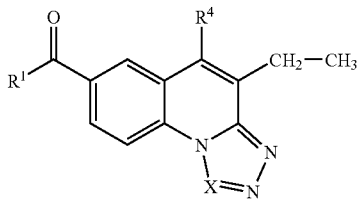

| Co. no. | Ex. no. | R⁴ | R¹ | X | physical data |
|---|---|---|---|---|---|
| 33 | B4 | H | methoxycyclohexyl | CH | cis; mp. 224° C. |
| 34 | B4 | H | metboxycyclohexyl | CH | trans; mp. 185° C. |
| 35 | B4 | H | methoxycyclohexyl | N | cis; mp. 160–172° C. |
| 170 | B4 | H | methoxycyclohexyl | N | trans; mp. 146° C. |
| 171 | B4 | H | norbornyl | N | (B); mp. 165° C. |
| 172 | B4 | H | methylcyclohexyl | N | cis + trans; mp. 143° C. |
| 173 | B4 | ethyl | methoxycyclohexyl | N | cis; mp.: 126° C. |
| 411 | B4 | H | phenylethyl | N | mp.: 109° C. |
| 412 | B4 | H | tetrahydronaphthyl | N | mp.: 180° C. |

TABLE 5-continued

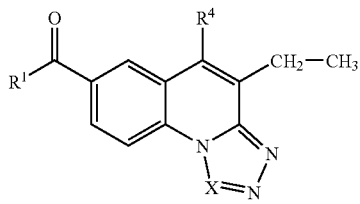

| Co. no. | Ex. no. | R⁴ | R¹ | X | physical data |
|---|---|---|---|---|---|
| 413 | B4 | H | (phenethyl) | N | (A) |
| 414 | B4 | H | H₃CO-(cyclohexyl-CH₂) | N | mp.: 156° C. |

TABLE 6

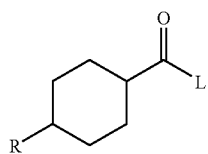

| Co. no. | Ex. no. | R | L | physical data |
|---|---|---|---|---|
| 49 | B7 | H | (6-methyl-3-methyl-quinoline N-oxide) | — |
| 174 | B3b | OCH₃ | (7-methyl-2,3-dihydro-pyrano[2,3-b]quinoline) | cis; mp. 115° C. |
| 175 | B3b | OCH₃ | (7-methyl-2,3-dihydro-pyrano[2,3-b]quinoline) | trans; mp. 141° C. |
| 176 | B3b | OCH₃ | (7-methyl-2,3-dihydro-thiopyrano[2,3-b]quinoline) | cis; mp. 149° C. |
| 177 | B3b | OCH₃ | (2-methyl-6-methoxy-phenanthridine) | mp. 126° C. |
| 178 | B3b | OCH₃ | (7-methyl-2,3-dihydro-thiopyrano[2,3-b]quinoline) | trans; mp. 160° C. |

TABLE 6-continued
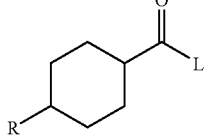
| Co. no. | Ex. no. | R | L | physical data |
|---|---|---|---|---|
| 179 | B3b | OCH₃ | 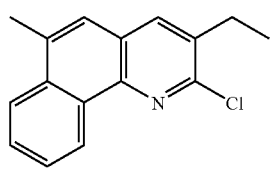 | cis; mp. 119° C. |
| 180 | B3b | OCH₃ | 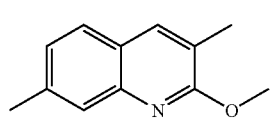 | trans; mp. 124° C. |
| 181 | B3b | OCH₃ | 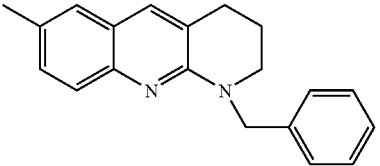 | trans; mp. 92° C. |
| 206 | B3b | OCH₃ | 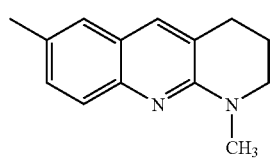 | cis; m.p. 144° C. |
| 207 | B3b | OCH₃ | 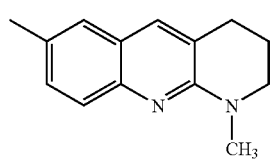 | trans; m.p. 125° C. |
| 208 | B3b | OCH₃ | 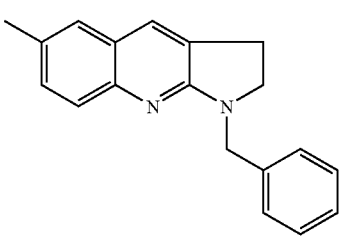 | cis; m.p. 127° C. |
| 209 | B3b | OCH₃ | 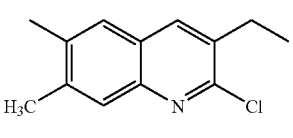 | cis; m.p. 101° C. |
| 210 | B3b | OCH₃ | 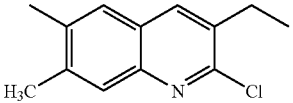 | cis; m.p. 104° C. |
| 211 | B3b | OCH₃ | | trans; m.p. 134° C. |

TABLE 6-continued
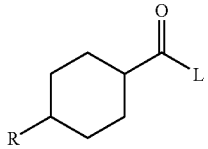
| Co. no. | Ex. no. | R | L | physcial data |
|---|---|---|---|---|
| 212 | B4 | OCH₃ | 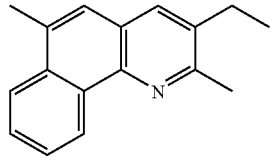 | cis; m.p. 141° C. |
| 213 | B4 | OCH₃ | 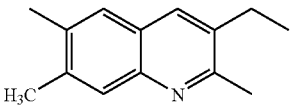 | trans; m.p. 215° C. |
| 214 | B4 | OCH₃ | 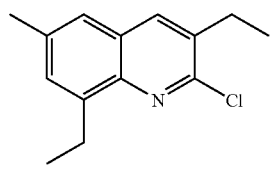 | cis; m.p. 139° C. |
| 215 | B3b | OCH₃ | 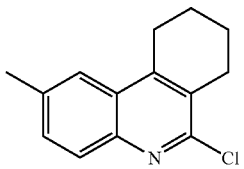 | trans |
| 415 | B3b | OCH₃ | 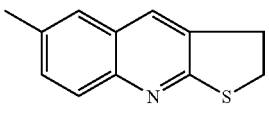 | (cis); mp.: 136° C. |
| 416 | B3b | OCH₃ | 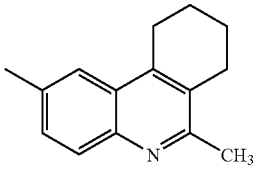 | (cis) |
| 417 | B4 | OCH₃ | 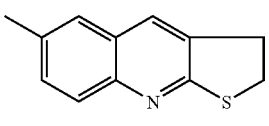 | (cis); mp.: 149° C. |
| 418 | B3b | OCH₃ | 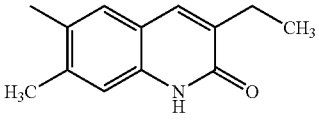 | (trans); mp.: 132° C. |
| 419 | B4 | OCH₃ | | (cis); mp.: 217° C. |

TABLE 6-continued
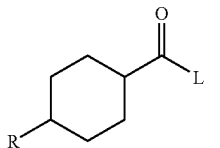
| Co. no. | Ex. no. | R | L | physcial data |
|---|---|---|---|---|
| 420 | B3b | OCH$_3$ | 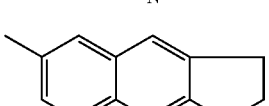 | (cis); .HCl(1:1); mp.: 200° C. |
| 421 | B4 | OH | 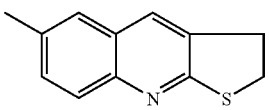 | (cis); mp.: 215° C. |
| 422 | B4 | OH | 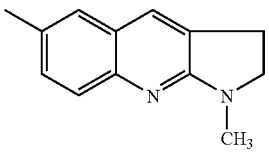 | (trans); mp.: 178° C. |
| 423 | B3b | OCH$_3$ | 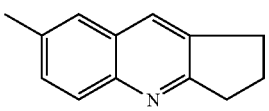 | mp.: 160° C. |
| 424 | B3b | OCH$_3$ | 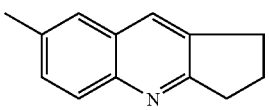 | (cis); mp.: 106° C. |
| 425 | B3b | OCH$_3$ | 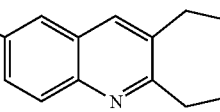 | (trans); mp.: 120° C. |
| 426 | B3b | OCH$_3$ | 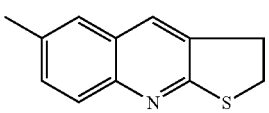 | (cis); mp.: 121° C. |
| 427 | B3b | H | 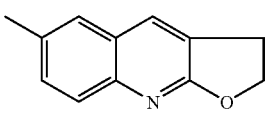 | mp.: 156° C. |
| 428 | B3b | OCH$_3$ | 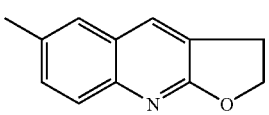 | (cis); mp.: 156° C. |
| 429 | B3b | OCH$_3$ | 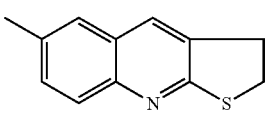 | (trans); mp.: 197° C. |
| 430 | B3b | CH$_3$ |  | (B) |

TABLE 6-continued

*[Structure: 4-R-cyclohexyl-C(=O)-L]*

| Co. no. | Ex. no. | R | L | physcial data |
|---|---|---|---|---|
| 431 | B3b | CH₃ | *[6-methyl-2,3-dihydrothieno[2,3-b]quinoline]* | (A) |

TABLE 7

*[Structure: R¹-C(=O)-L]*

| Co. no. | Ex. no. | R¹ | L | physcial data |
|---|---|---|---|---|
| 432 | B4 | *[phenylethyl]* | *[6-methyl-2,3-dihydropyrano[2,3-b]quinoline]* | mp.: 128° C. |
| 433 | B4 | *[1-methyladamantyl]* | *[6-methyl-2,3-dihydropyrano[2,3-b]quinoline]* | mp.: 175° C. |
| 434 | B4 | *[phenylpropyl]* | *[6-methyl-2,3-dihydropyrano[2,3-b]quinoline]* | mp.: 170° C. |
| 435 | B4 | *[cyclohex-3-enyl]* | *[6-methyl-2,3-dihydropyrano[2,3-b]quinoline]* | mp.: 103° C. |
| 436 | B4 | *[1,2,3,4-tetrahydronaphthalen-2-yl]* | *[6-methyl-2,3-dihydropyrano[2,3-b]quinoline]* | mp.: 151° C. |
| 437 | B4 | *[3-methoxycyclohexyl]* | *[6-methyl-2,3-dihydropyrano[2,3-b]quinoline]* | (trans); mp.: 110° C. |
| 438 | B4 | *[2-methyl-2,3-dihydro-1,4-benzodioxin-2-yl]* | *[6-methyl-2,3-dihydropyrano[2,3-b]quinoline]* | mp.: 150° C. |
| 439 | B4 | *[phenylethyl]* | *[6-methyl-2,3-dihydrothiopyrano[2,3-b]quinoline]* | mp.: 150° C. |

TABLE 7-continued
| Co. no. | Ex. no. | R¹ | L | physcial data |
|---|---|---|---|---|
| 440 | B4 | 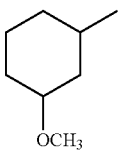 | 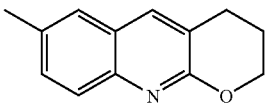 | (cis) |
| 441 | B4 | 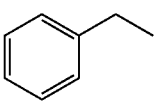 | 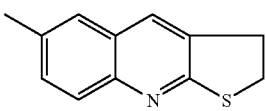 | mp.: 166° C. |
| 442 | B4 | 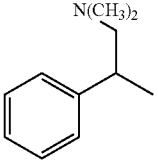 | 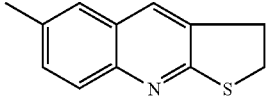 | mp.: 173° C. |
| 443 | B4 | 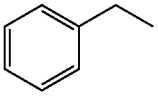 | 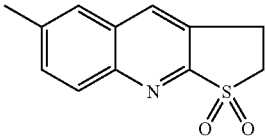 | mp.: 208° C. |
| 444 | B4 | 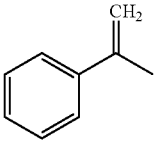 | 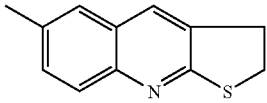 | mp.: 149° C. |
| 445 | B4 | 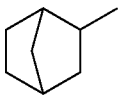 | 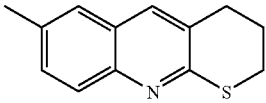 | mp.: 133° C. |
| 446 | B3b | 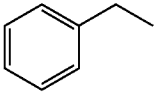 | 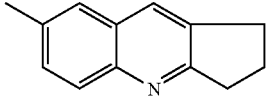 | mp.: 150° C. |
| 447 | B3b | 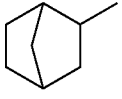 | 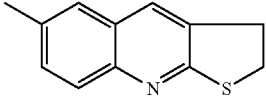 | mp.: 165° C. |
| 448 | B3b | 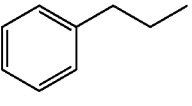 | 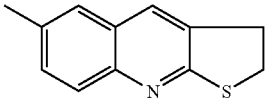 | mp.: 147° C. |
| 449 | B3b |  | 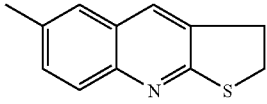 | mp.: 154° C. |

TABLE 7-continued

| Co. no. | Ex. no. | R¹ | L | physical data |
|---|---|---|---|---|
| 450 | B3b | 2-methyl-tetralin | 7-methyl-2,3-dihydrothieno[3,2-b]quinoline | mp.: 157° C. |
| 451 | B4 | 1-methyl-4-(2-phenylpropyl)piperazine | 7-methyl-2,3-dihydrothieno[3,2-b]quinoline | mp.: 190° C. |
| 452 | B4 | 4-(2-phenylpropyl)morpholine | 7-methyl-2,3-dihydrothieno[3,2-b]quinoline | mp.: 187° C. |
| 453 | B3b | 4-bromophenethyl | 7-methyl-2,3-dihydrothieno[3,2-b]quinoline | mp.: 200° C. |
| 454 | B3b | phenethyl | 8-methyl-6,7,8,9-tetrahydro-5H-cyclohepta[b]quinoline | mp.: 160° C. |
| 455 | B3b | phenethyl | 2,7-dimethyl-2,3-dihydrofuro[3,2-b]quinoline | mp.: 139° C. |
| 456 | B3b | 7-oxabicyclo[2.2.1]heptane | 7-methyl-3,4-dihydro-2H-pyrano[3,2-b]quinoline | (A); mp.: 174° C. |
| 457 | B3b | 7-oxabicyclo[2.2.1]heptane | 7-methyl-3,4-dihydro-2H-pyrano[3,2-b]quinoline | (B); mp.: 160° C. |
| 458 | B3b | phenethyl | 2,8-dimethyl-1,2,3,4-tetrahydrobenzo[b][1,6]naphthyridine | mp.: 184° C. |

TABLE 7-continued $$R^1-\underset{\underset{O}{\|}}{C}-L$$

| Co. no. | Ex. no. | R¹ | L | physcial data |
|---|---|---|---|---|
| 459 | B4 | 4-cyanophenylethyl | 7-methyl-2-(tert-butoxycarbonyl)-1,2,3,4-tetrahydrobenzo[b][1,6]naphthyridine | — |
| 460 | B4 | 5-methyl-2-methoxy-3,6-dihydro-2H-pyran | 7-methyl-2,3-dihydropyrano[2,3-b]quinoline | mp.: 134° C. |
| 461 | B4 | norbornenyl-methyl | 7-methyl-2,3-dihydropyrano[2,3-b]quinoline | (B); mp.: 156° C. |
| 462 | B4 | phenylethyl | 7-methyl-2,3-dihydrothieno[2,3-b]quinoline | mp.: 153° C. |
| 463 | B3b | phenylethyl | 7-methyl-2,3-dihydrofuro[2,3-b]quinoline | mp.: 161° C. |
| 464 | B4 | 3-thienylethyl | 7-methyl-2,3-dihydrothiopyrano[2,3-b]quinoline | mp.: 135° C. |
| 465 | B4 | 3-thienylethyl | 7-methyl-2,3-dihydropyrano[2,3-b]quinoline | mp.: 131° C. |
| 466 | B3b | 3-methylchroman | 7-methyl-2,3-dihydrothieno[2,3-b]quinoline | .HCl(1:1); mp.: 206° C. |
| 467 | B3d | phenylethyl | 7-methyl-2-(tert-butoxycarbonyl)-1,2,3,4-tetrahydrobenzo[b][1,6]naphthyridine | mp.: 142° C. |
| 468 | B4 | 4-methyl-cyclohexene oxide | 7-methyl-2,3-dihydropyrano[2,3-b]quinoline | .hydrate(1:1); mp.: 104° C. |
| 469 | B3b | dimethylethyl | 7-methyl-2,3-dihydrothieno[2,3-b]quinoline | mp.: 104° C. |

TABLE 7-continued
| Co. no. | Ex. no. | R¹ | L | physical data |
|---|---|---|---|---|
| 470 | B3b | 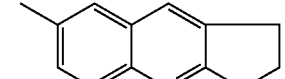 | 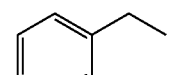 | mp.: 161° C. |
| 472 | B3b | 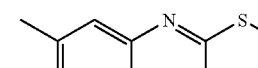 | 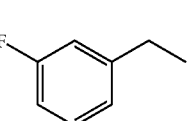 | mp.: 144° C. |
| 473 | B4 | 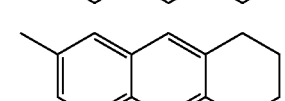 | 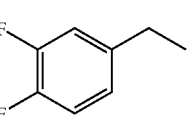 | mp.: 143° C. |
| 474 | B4 | 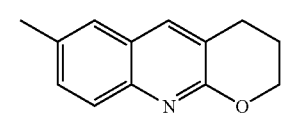 | 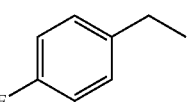 | mp.: 196° C. |
| 475 | B4 | 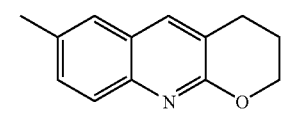 | 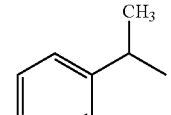 | mp.: 162° C. |
| 476 | B4 | 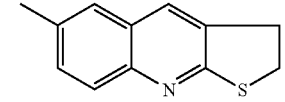 | 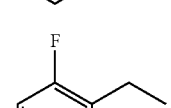 | mp.: 171° C. |
| 477 | B4 | 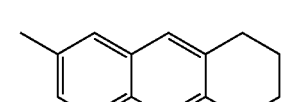 | 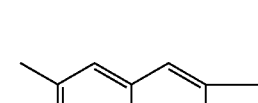 | mp.: 155° C. |
| 478 | B2 | trimethylmethyl | 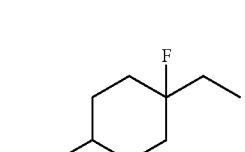 | mp.: 124° C. |
| 479 | B4 | 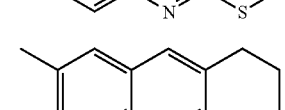 | 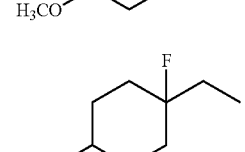 | (A); mp.: 146° C. |
| 480 | B4 | 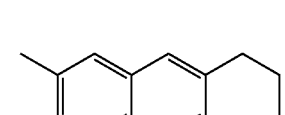 | 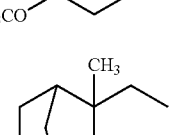 | (B); mp.: 162° C. |
| 481 | B4 | 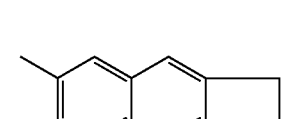 | | (A); mp.: 129° C. |

TABLE 7-continued
| Co. no. | Ex. no. | R¹ | L | physical data |
|---|---|---|---|---|
| 482 | B4 |  | 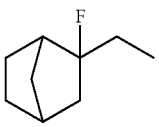 | mp.: 115° C. |
| 483 | B2 | 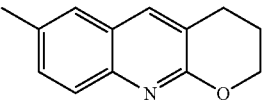 | 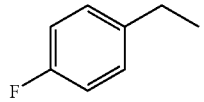 | mp.: 187° C. |
| 484 | B2 | 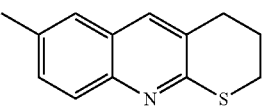 | 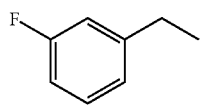 | mp.: 162° C. |
| 485 | B4 | 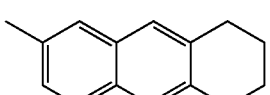 | 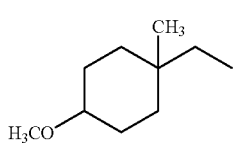 | (A); mp.: 130° C. |
| 486 | B4 | 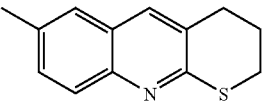 | 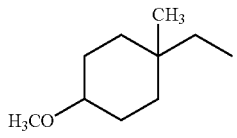 | (A); mp.: 124° C. |
| 487 | B4 | 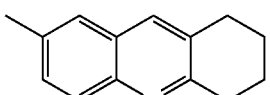 | 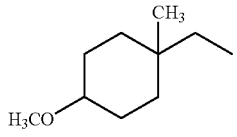 | (B); mp.: 128° C. |
| 488 | B4 | 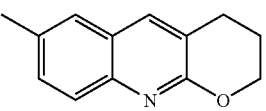 | 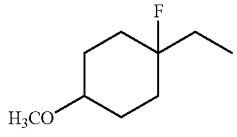 | mp.: 85° C. |
| 489 | B2 | 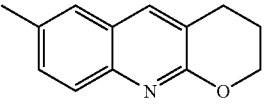 | 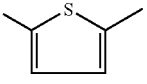 | mp.: 150° C. |
| 490 | B4 | 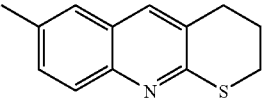 | 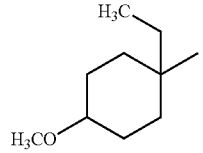 | (A); mp.: 117° C. |
| 491 | B2 | 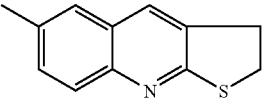 | 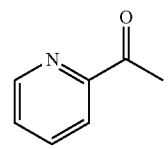 | mp.: 220° C. |

TABLE 7-continued $$R^1 \overset{O}{\underset{}{\text{—}}} L$$

| Co. no. | Ex. no. | R¹ | L | physcial data |
|---|---|---|---|---|
| 492 | B4 | (methylnorbornyl) | (methyl-thiopyrano-quinoline) | mp.: 136° C. |
| 493 | B2 | 4-(dimethylamino)methyl-phenylmethyl | (methyl-pyrano-quinoline) | mp.: 131° C. |
| 494 | B4 | (methylnorbornyl) | (methyl-pyrano-quinoline) | (A); mp.: 125° C. |
| 495 | B4 | (fluoronorbornyl) | (methyl-thiopyrano-quinoline) | mp.: 135° C. |
| 496 | B4 | (fluoronorbornyl) | (methyl-thieno-quinoline) | mp.: 139° C. |
| 497 | B4 | (norbornylmethyl) | (methyl-pyrano-quinoline) | mp.: 127° C. |
| 498 | B4 | 4-bromophenylmethyl | (methyl-pyrano-quinoline) | mp.: 195° C. |
| 499 | B2 | 2-fluorophenylmethyl | (methyl-thiopyrano-quinoline) | mp.: 201° C. |
| 500 | B3b | phenylmethyl | (methyl-methylfurano-quinoline) | mp.: 143° C. |
| 501 | B3b | phenylmethyl | (methyl-pyrano-quinoline) | mp.: 137° C. |
| 502 | B2 | 2-acetylpyridyl | (methyl-thiopyrano-quinoline) | mp.: 210° C. |

TABLE 7-continued

| Co. no. | Ex. no. | R¹ | L | physical data |
|---|---|---|---|---|
| 503 | B3d | benzyl-CH2- | 6-methyl-3-ethyl-2-methyl-8-methoxyquinolinyl | mp.: 134° C. |
| 504 | B2 | benzyl-CH2- | 6,7-dimethyl-2,3-dihydropyrano[2,3-b]quinolinyl | mp.: 163° C. |
| 505 | B4 | benzyl-CH2- | 7-methyl-1,2,3,4-tetrahydro-1,5-naphthyridinyl | mp.: 142° C. |
| 506 | B2 | benzyl-CH2- | 6,7-dimethyl-2,3-dihydrothiopyrano[2,3-b]quinolinyl | mp.: 139° C. |
| 507 | B4 | adamantyl-CH2- | 6-methyl-2,3-dihydrothiopyrano[2,3-b]quinolinyl | mp.: 171° C. |
| 512 | B3b | 2-methyl-1,4-benzodioxinyl | 6-methyl-2,3-dihydrothiopyrano[2,3-b]quinolinyl | — |
| 523 | B3b | 2-fluorophenyl-CH2- | 6-methyl-2,3-dihydrothieno[2,3-b]quinolinyl | — |

TABLE 8

| Co. no. | Ex. no. | Structure | physical data |
|---|---|---|---|
| 511 | B11 | quinuclidinyl-quinolinyl derivative | — |
| 514 | B12 | benzisoxazolyl-dihydrothienoquinolinyl derivative | — |

TABLE 8-continued

| Co. no. | Ex. no. | Structure | physical data |
|---|---|---|---|
| 515 | B13 | 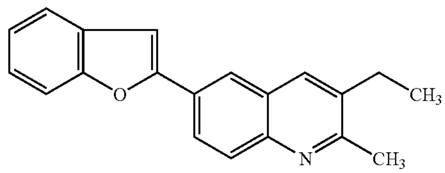 | — |
| 524 | B9a | 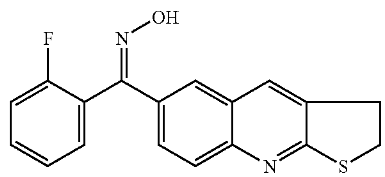 | mp.: 185° C. |
| 471 | B15 | 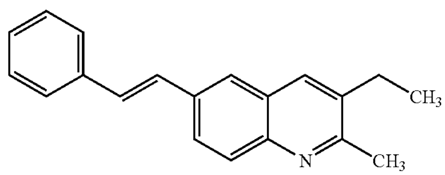 | (E) |
| 526 | B14 | 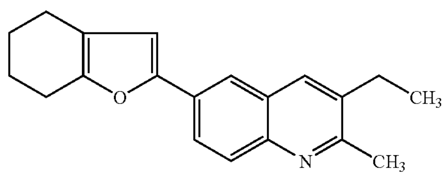 | .HCl(1:1) |

C. Pharmacological Example

Signal Transduction at the Cloned Rat mGluR1 Receptor in CHO Cells

CHO cells expressing the mGluR1 receptor were plated in precoated black 96-well plates. The next day, the effect of the present compounds on glutamate-activated intracellular $Ca^{2+}$ increase was evaluated in a fluorescent based assay. The cells were loaded with Fluo-3 AM, plates were incubated for 1 hour at room temperature in the dark, cells were washed and the present compounds were added onto the cells for 20 minutes. After this incubation time, the glutamate-induced $Ca^{2+}$ rise was recorded for each well in function of time using the Fluorescent Image Plated Reader (FLIPR, Molecular Devices Inc.). Relative fluorescence units were recorded and average data graphs of quadruple wells were obtained. Concentration-response curves were constructed based on peak fluorescence (maximum signal between 1 and 90 seconds) for each concentration of tested compound. $pIC_{50}$ values are the —log values of the concentration of tested compounds resulting in 50% inhibition of the glutamated-induced intracellular $Ca^{2+}$ rise.

The compounds according to the present invention exhibited a $pIC_{50}$ value of at least 5.

The compounds that are included in the Tables 1-8 exhibited a $pIC_{50}$ value of at least 6.

A particular group of compounds exhibited a $pIC_{50}$ value between 7 and 8. It concerns the compounds listed in Table 9.

TABLE 9

| Com. nr. | $pIC_{50}$ |
|---|---|
| 463 | 7.98 |
| 441 | 7.95 |
| 334 | 7.95 |
| 22 | 7.94 |
| 421 | 7.94 |
| 15 | 7.93 |
| 440 | 7.93 |
| 139 | 7.93 |
| 178 | 7.92 |
| 338 | 7.91 |
| 87 | 7.90 |
| 462 | 7.90 |
| 394 | 7.90 |
| 423 | 7.89 |
| 21 | 7.87 |
| 220 | 7.87 |
| 479 | 7.86 |
| 483 | 7.86 |
| 485 | 7.84 |
| 9 | 7.84 |
| 110 | 7.84 |
| 248 | 7.84 |
| 341 | 7.83 |
| 163 | 7.81 |
| 433 | 7.79 |
| 238 | 7.79 |
| 224 | 7.78 |
| 437 | 7.78 |
| 498 | 7.78 |
| 449 | 7.77 |
| 242 | 7.76 |

TABLE 9-continued
| Com. nr. | pIC$_{50}$ |
|---|---|
| 346 | 7.74 |
| 182 | 7.73 |
| 486 | 7.73 |
| 447 | 7.72 |
| 7 | 7.72 |
| 175 | 7.71 |
| 475 | 7.71 |
| 480 | 7.71 |
| 213 | 7.70 |
| 239 | 7.70 |
| 241 | 7.67 |
| 461 | 7.65 |
| 115 | 7.64 |
| 445 | 7.63 |
| 281 | 7.63 |
| 487 | 7.63 |
| 299 | 7.63 |
| 431 | 7.61 |
| 98 | 7.57 |
| 464 | 7.57 |
| 446 | 7.56 |
| 251 | 7.55 |
| 484 | 7.54 |
| 494 | 7.53 |
| 128 | 7.52 |
| 344 | 7.52 |
| 161 | 7.49 |
| 298 | 7.48 |
| 454 | 7.45 |
| 456 | 7.45 |
| 277 | 7.44 |
| 91 | 7.43 |
| 356 | 7.42 |
| 229 | 7.41 |
| 333 | 7.41 |
| 326 | 7.41 |
| 369 | 7.40 |
| 430 | 7.39 |
| 435 | 7.38 |
| 35 | 7.36 |
| 228 | 7.36 |
| 429 | 7.36 |
| 117 | 7.35 |
| 291 | 7.35 |
| 313 | 7.35 |
| 280 | 7.34 |
| 460 | 7.34 |
| 482 | 7.34 |
| 343 | 7.33 |
| 425 | 7.32 |
| 473 | 7.32 |
| 287 | 7.31 |
| 448 | 7.31 |
| 243 | 7.29 |
| 323 | 7.28 |
| 159 | 7.28 |
| 289 | 7.27 |
| 184 | 7.26 |
| 436 | 7.26 |
| 89 | 7.25 |
| 108 | 7.25 |
| 373 | 7.25 |
| 255 | 7.23 |
| 527 | 7.23 |
| 303 | 7.22 |
| 296 | 7.22 |
| 221 | 7.21 |
| 193 | 7.21 |
| 14 | 7.20 |
| 131 | 7.19 |
| 438 | 7.19 |
| 148 | 7.18 |
| 496 | 7.18 |
| 236 | 7.17 |
| 332 | 7.17 |
| 481 | 7.16 |
| 191 | 7.16 |
| 457 | 7.14 |
| 20 | 7.14 |
| 145 | 7.13 |
| 268 | 7.13 |
| 512 | 7.13 |
| 474 | 7.13 |
| 10 | 7.11 |
| 307 | 7.11 |
| 426 | 7.11 |
| 466 | 7.10 |
| 97 | 7.08 |
| 83 | 7.08 |
| 434 | 7.08 |
| 300 | 7.08 |
| 199 | 7.07 |
| 290 | 7.06 |
| 112 | 7.05 |
| 348 | 7.05 |
| 286 | 7.03 |
| 442 | 7.03 |
| 422 | 7.02 |
| 283 | 7.02 |
| 318 | 7.02 |
| 36 | 7.00 |
| 396 | 7.00 |
A particular group of compounds exhibited a pIC$_{50}$ value of at least 8. It concern the compounds listed in Table 10.
TABLE 10
| Comp. nr. | Structure | pIC50 |
|---|---|---|
| 416 | 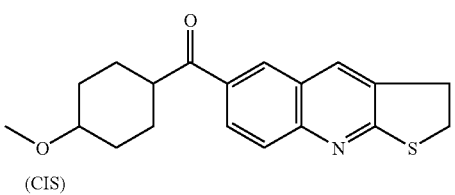 (CIS) | 8.587 |

TABLE 10-continued

| Comp. nr. | Structure | pIC50 |
|---|---|---|
| 27 | (CIS) | 8.527 |
| 174 | (CIS) | 8.49 |
| 506 | 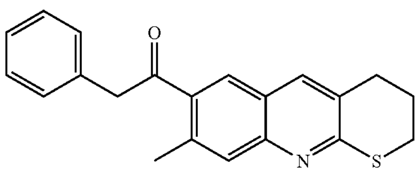 | 8.48 |
| 25 | (CIS) | 8.45 |
| 4 | (CIS) | 8.4 |
| 19 | (CIS) | 8.38 |
| 429 | (CIS) | 8.38 |

TABLE 10-continued

| Comp. nr. | Structure | pIC50 |
|---|---|---|
| 424 | (CIS) | 8.355 |
| 176 | (CIS) | 8.33 |
| 210 | (CIS) | 8.315 |
| 114 | (CIS) | 8.28 |
| 488 | 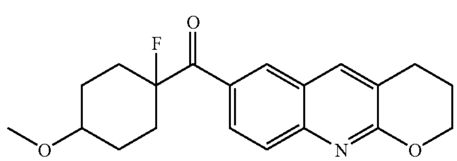 | 8.27 |
| 504 | 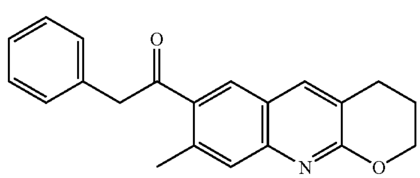 | 8.27 |
| 477 | 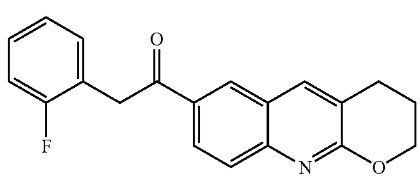 | 8.25 |
| 432 | 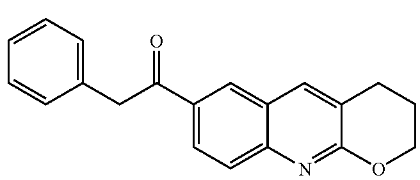 | 8.237 |

TABLE 10-continued

| Comp. nr. | Structure | pIC50 |
|---|---|---|
| 214 | (CIS) | 8.233 |
| 465 | 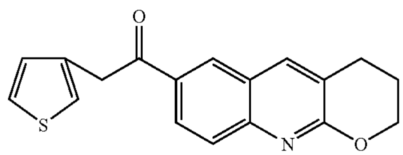 | 8.145 |
| 135 | (CIS) | 8.14 |
| 420 | (CIS) Hydrochloride (1:1) | 8.135 |
| 292 | (CIS) | 8.13 |
| 427 | 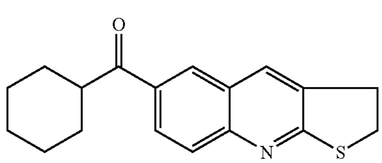 | 8.115 |
| 208 | (CIS) | 8.095 |
| 419 | (CIS) | 8.065 |

TABLE 10-continued

| Comp. nr. | Structure | pIC50 |
|---|---|---|
| 455 | 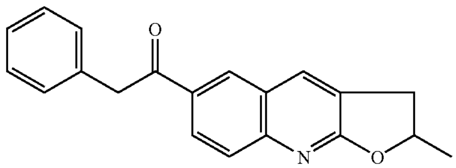 | 8.055 |
| 418 | (TRANS) | 8.045 |
| 497 | 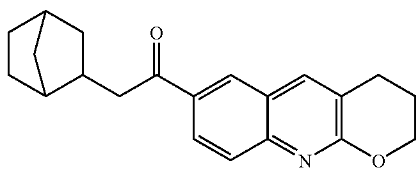 | 8.025 |
| 439 | 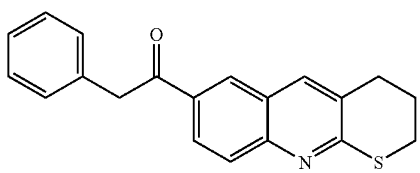 | 8.023 |
| 237 | 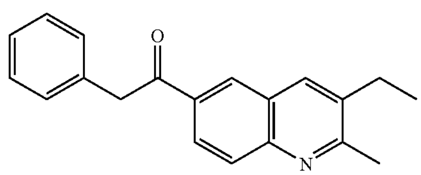 | 8.01 |
| 499 | 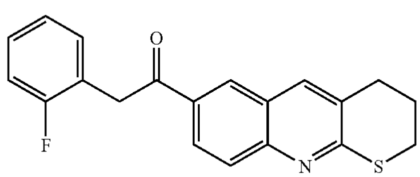 | 8 |

Cold Allodynia Test in Rats with a Bennett Ligation

Surgery:

Male SD rats, weighing 240-280 g at the time of surgery were used.

For surgery, the animals were anaesthetised with Thalamonal (1 ml; subcutane) and sodium pentobarbital (40 mg/kg; intraperitoneal (IP)). The common sciatic nerve of the left hindpaw was exposed at the level of the middle of the thigh by blunt dissection through the biceps femoris. Proximal to the sciatic's trifurcation, about 7 mm of nerve was freed and four loose ligatures with 4.0 chromic gut were placed around the sciatic nerve. Great care was taken to tie the ligatures such that the diameter of the nerve was barely constricted. After surgery, the animals received 1.25 mg/kg naloxone IP.

Cold Plate Testing:

Cold plate testing was performed on a metal plate of 30×30 cm with transparent acrylic walls around it. The cold plate was cooled to 0.0 (±0.5)° C. using a Julabo F25 cooler. For testing, the animal was placed on the cold plate and the duration of lifting of both the left and the right hindpaw was measured during 5 minutes. The difference in lifting time between the ligated and non-ligated paw was calculated.

Testing Procedure:

At least one week after the operation, animals were placed on the cold plate test and a pre-drug measurement was taken. Animals having a difference in lifting time >25 secondes between the ligated and the non-ligated paw were selected for drug testing. These selected animals were injected IP with a compound of the present invention and were retested after 60 minutes (post drug test). The results obtained during the post drug test were expressed as a percentage of those of the predrug test.

The data were analysed in terms of all or none criterion (based on the results of control animals) with the limits being:

Inhibition: (post-drug/pre-drug)*100<40%
Antagonism: (post-drug/pre-drug)*100<25%

Compound (27) showed antagonism at a dose of 2.5 mg/kg bodyweight.

The invention claimed is:

1. A compound of formula

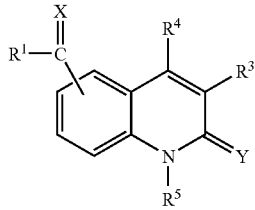

(I-B)

an N-oxide form, a pharmaceutically acceptable addition salt, a quaternary amine or a stereochemically isomeric form thereof, wherein X represents O; $C(R^6)_2$ with $R^6$ being hydrogen, aryl or $C_{1-6}$alkyl optionally substituted with amino or mono- or di($C_{1-6}$alkyl)amino; S or N—$R^7$ with $R^7$ being amino or hydroxy;

$R^1$ represents $C_{1-6}$alkyl; thienyl; quinolinyl; cyclo$C_{3-12}$alkyl or cyclo$C_{3-12}$alkyl$C_{1-6}$alkyl, wherein the cyclo $C_{3-12}$alkyl moiety optionally may contain a double bond and wherein one carbon atom in the cyclo$C_{3-12}$alkyl moiety may be replaced by an oxygen atom or an $NR^8$-moiety with $R^8$ being hydrogen, benzyl or $C_{1-6}$alkyloxycarbonyl; wherein one or more hydrogen atoms in a $C_{1-6}$alkyl-moiety or in a cyclo$C_{3-12}$alkyl-moiety optionally may be replaced by $C_{1-6}$alkyl, hydroxy$C_{1-6}$alkyl, halo$C_{1-6}$alkyl, amino$C_{1-6}$alkyl, hydroxy, $C_{1-6}$alkyloxy, aryl$C_{1-6}$alkyloxy, $C_{1-6}$alkyloxycarbonyl, aryl, amino, mono- or di($C_{1-6}$alkyl)amino, $C_{1-6}$alkyloxycarbonylamino, piperazinyl, pyridinyl, morpholinyl, thienyl or a bivalent radical of formula —O—, —O—$CH_2$—O— or —O—$CH_2$—$CH_2$—O—; or a radical of formula (a-1)

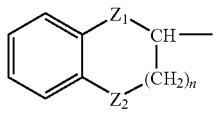

a-1 wherein $Z_1$ is a single covalent bond, O, NH or $CH_2$;
$Z_2$ is a single covalent bond, O, NH or $CH_2$;
n is an integer of 0, 1, 2 or 3;
and wherein each hydrogen atom in the phenyl ring independently may optionally be replaced by halo, hydroxy, $C_{1-6}$alkyl, $C_{1-6}$alkyloxy or hydroxy$C_{1-6}$alkyl;

or X and $R^1$ may be taken together with the carbon atom to which X and $R^1$ are attached to form a radical of formula (b-1), (b-2) or (b-3);

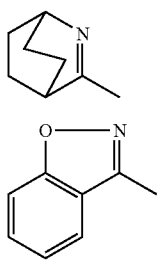

b-1 b-2

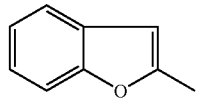

b-3

$R^3$ represents hydrogen; halo; hydroxy; cyano; $C_{1-6}$alkyl; $C_{1-6}$alkyloxy; $C_{1-6}$alkyloxy$C_{1-6}$alkyl; $C_{1-6}$alkylcarbonyl; $C_{1-6}$alkyloxycarbonyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di($C_{1-6}$alkyl)amino; mono- or di($C_{1-6}$alkyloxy$C_{1-6}$alkyl)amino; mono- or di($C_{1-6}$alkylthio$C_{1-6}$alkyl)amino; aryl; morpholinyl$C_{1-6}$alkyl or piperidinyl$C_{1-6}$alkyl;

$R^4$ represents hydrogen; halo; hydroxy; cyano; $C_{1-6}$alkyl; $C_{1-6}$alkyloxy; $C_{1-6}$alkyloxy$C_{1-6}$alkyl; $C_{1-6}$alkylcarbonyl; $C_{1-6}$alkyloxycarbonyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di($C_{1-6}$alkyl)amino; mono- or di($C_{1-6}$alkyloxy$C_{1-6}$alkyl)amino; mono- or di($C_{1-6}$alkylthio$C_{1-6}$alkyl)amino; morpholinyl$C_{1-6}$alkyl or piperidinyl$C_{1-6}$alkyl; or $R^3$ and $R^4$ may be taken together to form a bivalent radical of formula —CH=CH—CH=CH— or —$CH_2$—$CH_2$—$CH_2$—$CH_2$—;

$R^5$ represents hydrogen; cyclo$C_{3-12}$alkyl; piperidinyl; oxothienyl; tetrahydrothienyl; aryl$C_{1-6}$alkyl; $C_{1-6}$alkyloxy$C_{1-6}$alkyl; $C_{1-6}$alkyloxycarbonyl$C_{1-6}$alkyl or $C_{1-6}$alkyl optionally substituted with a radical C(=O)$NR_xR_y$, in which $R_x$ and $R_y$, each independently are hydrogen, cyclo$C_{3-12}$alkyl, $C_{2-6}$alkynyl or $C_{1-6}$alkyl optionally substituted with cyano, $C_{1-6}$alkyloxy, $C_{1-6}$alkyloxycarbonyl, furanyl, pyrrolidinyl, benzylthio, pyridinyl, pyrrolyl or thienyl;

Y represents O or S;

or Y and $R^5$ may be taken together to form =Y—$R^5$— which represents a radical of formula —CH=N—N= (c-1);

—N=N—N= (c-2); or

—N—CH=CH— (c-3);

aryl represents phenyl or naphthyl optionally substituted with one or more substituents selected from halo, hydroxy, $C_{1-6}$alkyl, $C_{1-6}$alkyloxy, phenyloxy, nitro, amino, thio, $C_{1-6}$alkylthio, halo$C_{1-6}$alkyl, polyhalo$C_{1-6}$alkyl, polyhalo$C_{1-6}$alkyloxy, hydroxy$C_{1-6}$alkyl, $C_{1-6}$alkyloxy$C_{1-6}$alkyl, amino$C_{1-6}$alkyl, mono- or di($C_{1-6}$alkyl)amino; mono- or di($C_{1-6}$alkyl)amino$C_{1-6}$alkyl, cyano, —CO—$R^{12}$, —CO—$OR^{13}$, —$NR^{13}SO_2R^{12}$, —$SO_2$—$NR^{13}R^{14}$, —$NR^{13}C(O)R^{12}$, —C(O)$NR^{13}R^{14}$, —$SOR^{12}$, —$SO_2R^{12}$; wherein each $R^{12}$, $R^{13}$ and $R^{14}$ independently represent $C_{1-6}$alkyl; cyclo$C_{3-6}$alkyl; phenyl; phenyl substituted with halo, hydroxy, $C_{1-6}$alkyl, $C_{1-6}$alkyloxy, halo$C_{1-6}$alkyl, polyhalo$C_{1-6}$alkyl, furanyl, thienyl, pyrrolyl, imidazolyl, thiazolyl or oxazolyl;

and when the $R^1$—C(=X) moiety is linked to another position than the 7 or 8 position, then said 7 and 8 position may be substituted with $R^{15}$ and $R^{16}$ wherein either one or both of $R^{15}$ and $R^{16}$ represents $C_{1-6}$alkyl, $C_{1-6}$alkyloxy or $R^{15}$ and $R^{16}$ taken together may form a bivalent radical of formula —CH=CH—CH=CH.

2. A compound according to claim 1, wherein

X represents O; $C(R^6)_2$ with $R^6$ being hydrogen or aryl; or N—$R^7$ with $R^7$ being amino or hydroxy;

$R^1$ represents $C_{1-6}$alkyl, thienyl; quinolinyl; cyclo$C_{3-12}$alkyl or (cyclo$C_{3-12}$alkyl)$C_{1-6}$alkyl, wherein the cycloC$_{3-12}$alkyl moiety optionally may contain a double bond and wherein one carbon atom in the cycloC$_{3-12}$ alkyl moiety may be replaced by an oxygen atom or an NR$^8$-moiety with R$^8$ being benzyl or C$_{1-6}$alkyloxycarbonyl; wherein one or more hydrogen atoms in a C$_{1-6}$alkyl-moiety or in a cycloC$_{3-12}$alkyl-moiety optionally may be replaced by C$_{1-6}$alkyl, haloC$_{1-6}$alkyl, hydroxy, C$_{1-6}$alkyloxy, arylC$_{1-6}$alkyloxy, aryl, mono- or di(C$_{1-6}$alkyl)amino, C$_{1-6}$alkyloxycarbonylamino, piperazinyl, pyridinyl, morpholinyl, thienyl or a bivalent radical of formula —O— or —O—CH$_2$—CH$_2$—O—;

or a radical of formula (a-1)

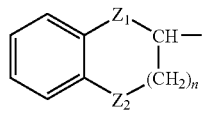

a-1 wherein
- Z$_1$ is a single covalent bond, O or CH$_2$;
- Z$_2$ is a single covalent bond, O or CH$_2$;
- n is an integer of 0, 1, or 2;
- and wherein each hydrogen atom in the phenyl ring independently may optionally be replaced by halo or hydroxy;

or X and R$^1$ may be taken together with the carbon atom to which X and R$^1$ are attached to form a radical of formula (b-1), (b-2) or (b-3);

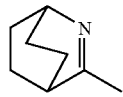

b-1

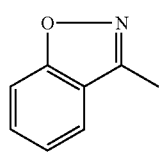

b-2

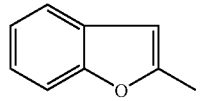

b-3

R$^3$ and R$^4$ each independently represent hydrogen; C$_{1-6}$alkyl; C$_{1-6}$alkyloxyC$_{1-6}$alkyl; C$_{1-6}$alkyloxycarbonyl; or R$^3$ and R$^4$ may be taken together to form a bivalent radical of formula —CH=CH—CH=CH— or —CH$_2$—CH$_2$—CH$_2$—;

R$^5$ represents hydrogen; piperidinyl; oxo-thienyl; tetrahydrothienyl, arylC$_{1-6}$alkyl; C$_{1-6}$alkyloxycarbonylC$_{1-6}$alkyl or C$_{1-6}$alkyl optionally substituted with a radical C(=O)NR$_x$R$_y$, in which R$_x$ and R$_y$ each independently are hydrogen, cycloC$_{3-12}$alkyl, C$_{2-6}$alkynyl or C$_{1-6}$alkyl optionally substituted with cyano, C$_{1-6}$alkyloxy or C$_{1-6}$alkyloxycarbonyl;

Y represents O or S;

or Y and R$^5$ may be taken together to form =Y—R$^5$— which represents a radical of formula

 (c-1); or

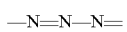 (c-2);

aryl represents phenyl or naphthyl optionally substituted with one or more substituents selected from halo, C$_{1-6}$alkyloxy, phenyloxy, mono- or di(C$_{1-6}$alkyl)amino and cyano;

and when the R$^1$—C(=X) moiety is linked to another position than the 7 or 8 position, then said 7 and 8 position may be substituted with R$^{15}$ and R$^{16}$ wherein either one or both of R$^{15}$ and R$^{16}$ represents C$_{1-6}$alkyl or R$^{15}$ and R$^{16}$ taken together may form a bivalent radical of formula —CH=CH—CH=CH—.

3. A compound according to claim 1, wherein

X represents O;

R$^1$ represents C$_{1-6}$alkyl; cycloC$_{3-12}$alkyl or (cycloC$_{3-12}$alkyl)C$_{1-6}$alkyl, wherein one or more hydrogen atoms in a C$_{1-6}$alkyl-moiety or in a cycloC$_{3-12}$alkyl-moiety optionally may be replaced by C$_{1-6}$alkyloxy, aryl, or thienyl;

R$^3$ and R$^4$ each independently represent hydrogen or C$_{1-6}$alkyl; or

R$^3$ and R$^4$ may be taken together to form a bivalent radical of formula —CH$_2$—CH$_2$—CH$_2$—CH$_2$—;

R$^5$ represents hydrogen;

Y represents O; and aryl represents phenyl optionally substituted with halo.

4. A compound as claimed in claim 1, having the formula:

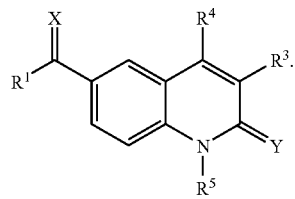

5. A pharmaceutical composition comprising a pharmaceutically acceptable carrier, and as active ingredient a therapeutically effective amount of a compound as defined in claim 1.

6. A process of preparing a composition as claimed in claim 5, comprising combining a pharmaceutically acceptable carrier with a therapeutically effective amount of said compound.

7. A process of preparing a compound of formula (I-B) as claimed in claim 1, comprising a) oxidizing an intermediate of formula (II) in the presence of a suitable oxidizing agent

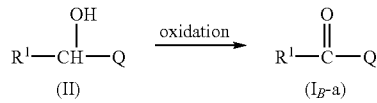

with Q representing the quinolinone or quinoline-2-thione moiety of a compound of formula (I-B); or b) reacting an intermediate of formula (III) with an intermediate of formula (IV)

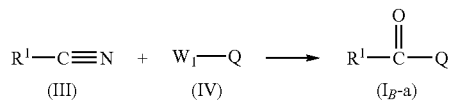

with Q representing the quinolinone or quinoline-2-thione moiety of a compound of formula (I-B) and W$_1$ being a suitable leaving group; or c) reacting an intermediate of formula (V) with an intermediate of formula (IV)

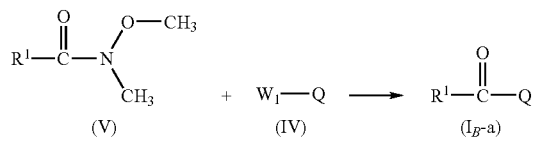

with Q representing the quinolinone or quinoline-2-thione moiety of a compound of formula (I-B) and W$_1$ being a suitable leaving group; or d) reacting an intermediate of formula (VI) with an intermediate of formula (VII) in the presence of a suitable acid

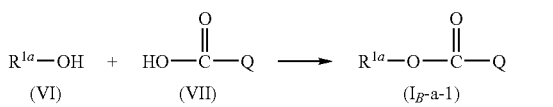

with $R^{1a}$ being defined as $R^1$ provided that $R^1$ is linked to the carbonyl moiety via a oxygen atom and Q representing the quinolinone or quinoline-2-thione moiety of a compound of formula (I-B); or e) reacting an intermediate of formula (VIII) in the presence of a suitable acid

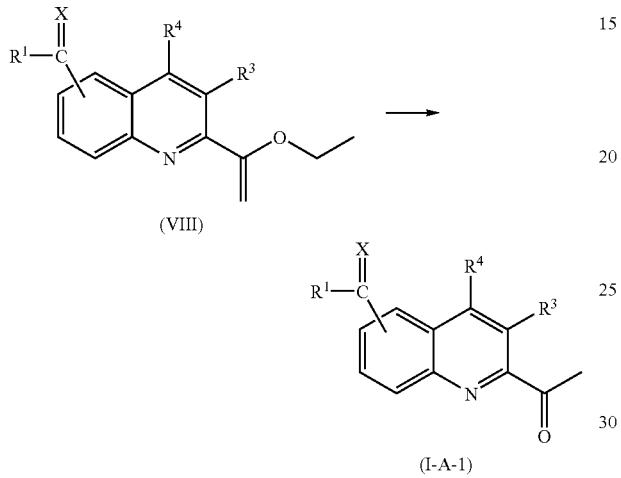

and, optionally, interconverting a first compound of formula (I-B) to yield a second compound of formula (I-B); and further, optionally, converting the compounds of formula (I-B) into a therapeutically active non-toxic acid addition salt by treatment with an acid, or converting the acid addition salt form into the free base by treatment with alkali; and, optionally, preparing stereochemically isomeric forms, quaternary amines or N-oxide forms thereof.

8. A pharmaceutical composition comprising a pharmaceutically acceptable carrier, and as active ingredient a therapeutically effective amount of a compound of formula

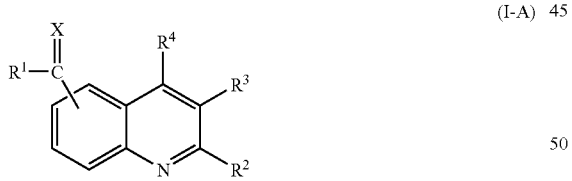

an N-oxide form, a pharmaceutically acceptable addition salt, a quaternary amine or a stereochemically isomeric form thereof, wherein X represents O; $C(R^6)_2$ with $R^6$ being hydrogen, aryl or $C_{1-6}$alkyl optionally substituted with amino or mono- or di($C_{1-6}$alkyl)amino; S or N—$R^7$ with $R^7$ being amino or hydroxy;

$R^1$ represents $C_{1-6}$alkyl; thienyl; quinolinyl; cyclo$C_{3-12}$alkyl or (cyclo$C_{3-12}$alkyl)$C_{1-6}$alkyl, wherein the cyclo$C_{3-12}$alkyl moiety optionally may contain a double bond and wherein one carbon atom in the cyclo$C_{3-12}$alkyl moiety may be replaced by an oxygen atom or an $NR^8$-moiety with $R^8$ being hydrogen, benzyl or $C_{1-6}$alkyloxycarbonyl; wherein one or more hydrogen atoms in a $C_{1-6}$alkyl-moiety or in a cyclo$C_{3-12}$alkyl-moiety optionally may be replaced by $C_{1-6}$alkyl, hydroxy$C_{1-6}$alkyl, halo$C_{1-6}$alkyl, amino$C_{1-6}$alkyl, hydroxy, $C_{1-6}$alkyloxy, aryl$C_{1-6}$alkyloxy, $C_{1-6}$alkyloxycarbonyl, aryl, amino, mono- or di($C_{1-6}$alkyl)amino, $C_{1-6}$alkyloxycarbonylamino, piperazinyl, pyridinyl, morpholinyl, thienyl or a bivalent radical of formula —O—, —O—CH$_2$—O or —O—CH$_2$—CH$_2$—O—;

or a radical of formula (a-1)

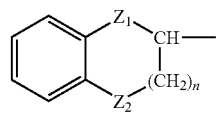

wherein $Z_1$ is a single covalent bond, O, NH or CH$_2$;
$Z_2$ is a single covalent bond, O, NH or CH$_2$;
n is an integer of 0, 1, 2 or 3;
and wherein each hydrogen atom in the phenyl ring independently may optionally be replaced by halo, hydroxy, $C_{1-6}$alkyl, $C_{1-6}$alkyloxy or hydroxy$C_{1-6}$alkyl;

or X and $R^1$ may be taken together with the carbon atom to which X and $R^1$ are attached to form a radical of formula (b-1), (b-2) or (b-3);

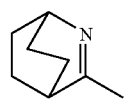

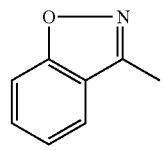

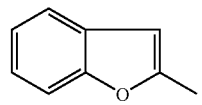

$R^2$ represents hydrogen; halo; cyano; $C_{1-6}$alkyl; $C_{1-6}$alkyloxy; $C_{1-6}$alkylthio; $C_{1-6}$alkylcarbonyl; $C_{1-6}$alkyloxycarbonyl; $C_{1-6}$alkylcarbonyloxy$C_{1-6}$alkyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di ($C_{1-6}$alkyl)amino; mono- or di($C_{1-6}$alkyloxy$C_{1-6}$alkyl) amino; mono- or di($C_{1-6}$alkylthio$C_{1-6}$alkyl)amino; aryl; aryl$C_{1-6}$alkyl; aryl$C_{2-6}$alkynyl; $C_{1-6}$alkyloxy$C_{1-6}$alkylamino$C_{1-6}$alkyl; aminocarbonyl optionally substituted with $C_{1-6}$alkyl, $C_{1-6}$alkyloxy$C_{1-6}$alkyl, $C_{1-6}$alkyloxycarbonyl$C_{1-6}$alkyl or pyridinyl$C_{1-6}$alkyl; a heterocycle selected from thienyl, furanyl, pyrrolyl, thiazolyl, oxazolyl, imidazolyl, isothiazolyl, isoxazolyl, pyrazolyl, pyridyl, pyrazinyl, pyridazinyl, pyrimidinyl, piperidinyl and piperazinyl, optionally N-substituted with $C_{1-6}$alkyloxy$C_{1-6}$alkyl, morpholinyl, thiomorpholinyl, dioxanyl or dithianyl; a radical —NH—C(=O)$R^9$ wherein $R^9$ represents $C_{1-6}$alkyl optionally substituted with cyclo$C_{3-12}$alkyl, $C_{1-6}$alkyloxy, $C_{1-6}$alkyloxycarbonyl, aryl, aryloxy, thienyl, pyridinyl, mono- or di($C_{1-6}$alkyl)amino, $C_{1-6}$alkylthio, benzylthio, pyridinylthio or pyrimidinylthio; cyclo$C_{3-12}$alkyl; cyclohexenyl; amino; arylcyclo$C_{3-12}$alkylamino; mono-or-di($C_{1-6}$alkyl)amino; mono- or di($C_{1-6}$alkyloxycarbonyl$C_{1-6}$alkyl)amino; mono- or di($C_{1-6}$alkyloxycarbonyl)amino; mono-or di($C_{2-6}$alkenyl)amino; mono- or di(aryl$C_{1-6}$alkyl) amino; mono- or diarylamino; aryl$C_{2-6}$alkenyl; furanyl$C_{2-6}$alkenyl; piperididinyl; piperazinyl; indolyl;

furyl; benzofuryl; tetrahydrofuryl; indenyl; adamantyl; pyridinyl; pyrazinyl; aryl; aryl$C_{1-6}$alkylthio or a radical of formula (a-1);

a sulfonamid —NH—$SO_2$—$R^{10}$ wherein $R^{10}$ represents $C_{1-6}$alkyl, mono- or polyhalo$C_{1-6}$alkyl, aryl$C_{1-6}$alkyl, aryl$C_{2-6}$alkenyl, aryl, quinolinyl, isoxazolyl or di($C_{1-6}$alkyl)amino;

$R^3$ represents hydrogen; halo; hydroxy; cyano; $C_{1-6}$alkyl; $C_{1-6}$alkyloxy; $C_{1-6}$alkyloxy$C_{1-6}$alkyl; $C_{1-6}$alkylcarbonyl; $C_{1-6}$alkyloxycarbonyl; $C_{2-6}$alkenyl; hydroxy$C_{2-6}$alkenyl; $C_{2-6}$alkynyl; hydroxy$C_{2-6}$alkynyl; tri($C_{1-6}$alkyl)silane$C_{2-6}$alkynyl; amino; mono- or di($C_{1-6}$alkyl)amino; mono- or di($C_{1-6}$alkyloxy$C_{1-6}$alkyl)amino; mono- or di($C_{1-6}$alkylthio$C_{1-6}$alkyl)amino; aryl; morpholinyl$C_{1-6}$alkyl or piperidinyl$C_{1-6}$alkyl;

$R^4$ represents $C_{1-6}$alkyloxy or amino; or $R^2$ and $R^3$ may be taken together to form —$R^2$—$R^3$—, which represents a bivalent radical of formula —$(CH_2)_3$—, —$(CH_2)_4$—, —$(CH_2)_5$—, —$(CH_2)_6$—, —CH=CH—CH=CH—, -$Z_4$-CH=CH—, —CH=CH-$Z_4$-, -$Z_4$-$CH_2$—$CH_2$—$CH_2$—, —$CH_2$-$Z_4$-$CH_2$—$CH_2$—, —$CH_2$—$CH_2$-$Z_4$-$CH_2$—, —$CH_2$—$CH_2$—$CH_2$-$Z_4$-, -$Z_4$-$CH_2$—$CH_2$— or —$CH_2$—$CH_2$-$Z_4$-, with $Z_4$ being O, S, $SO_2$ or $NR^{11}$ wherein $R^{11}$ is hydrogen, $C_{1-6}$alkyl, benzyl or $C_{1-6}$alkyloxycarbonyl; and wherein each bivalent radical is optionally substituted with $C_{1-6}$alkyl;

or $R^3$ and $R^4$ may be taken together to form a bivalent radical of formula —CH=CH—CH=CH— or —$CH_2$—$CH_2$—$CH_2$—$CH_2$—;

aryl represents phenyl or naphthyl optionally substituted with one or more substituents selected from halo, hydroxy, $C_{1-6}$alkyl, $C_{1-6}$alkyloxy, phenyloxy, nitro, amino, thio, $C_{1-6}$alkylthio, halo$C_{1-6}$alkyl, polyhalo$C_{1-6}$alkyl, polyhalo$C_{1-6}$alkyloxy, hydroxy$C_{1-6}$alkyl, $C_{1-6}$alkyloxy$C_{1-6}$alkyl, amino$C_{1-6}$alkyl, mono-or di($C_{1-6}$alkyl)amino; mono-or di($C_{1-6}$alkyl)amino$C_{1-6}$alkyl, cyano, —CO—$R^{12}$, —CO—$OR^{13}$, —$NR^{13}SO_2R^{12}$, —$SO_2$—$NR^{13}R^{14}$, —$NR^{13}C(O)R^{12}$, —C(O)$NR^{13}R^{14}$, —$SOR^{12}$, —$SO_2R^{12}$; wherein each $R^{12}$, $R^{13}$ and $R^{14}$ independently represent $C_{1-6}$alkyl; cyclo$C_{3-6}$alkyl; phenyl; phenyl substituted with halo, hydroxy, $C_{1-6}$alkyl, $C_{1-6}$alkyloxy, halo$C_{1-6}$alkyl, polyhalo$C_{1-6}$alkyl, furanyl, thienyl, pyrrolyl, imidazolyl, thiazolyl or oxazolyl;

and when the $R^1$—C(=X) moiety is linked to another position than the 7 or 8 position, then said 7 and 8 position may be substituted with $R^{15}$ and $R^{16}$ wherein either one or both of $R^{15}$ and $R^{16}$ represents $C_{1-6}$alkyl, $C_{1-6}$alkyloxy or $R^{15}$ and $R^{16}$ taken together may form a bivalent radical of formula —CH=CH—CH=CH—.

9. A process of preparing a composition as claimed in claim 8, comprising combining a pharmaceutically acceptable carrier with a therapeutically effective amount of said compound.

* * * * *

UNITED STATES PATENT AND TRADEMARK OFFICE
CERTIFICATE OF CORRECTION

PATENT NO. : 7,629,468 B2  Page 1 of 1
APPLICATION NO. : 11/133678
DATED : December 8, 2009
INVENTOR(S) : Mabire et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,629,468 B2 | |
| APPLICATION NO. | : 11/133678 | |
| DATED | : December 8, 2009 | |
| INVENTOR(S) | : Mabire et al. | |

It is certified that error appears in the above-identified patent and that said Letters Patent is hereby corrected as shown below:

Title Page:

(62) Delete "filed on Aug. 14, 2003, now Pat. No. 7,115,630." and insert --filed as application No. PCT/EP01/11135 on September 25, 2001, now Pat. No. 7,115,630.--

Title Page:

Add:

--Foreign Application Priority Data

October 2, 2000   (EP)        00203419.7--

Column 17,
Line 49, delete "$R^{5a}$-$W_3$" and insert --$R^{5a}$-$W_4$--
Line 50, delete "(XIV)" and insert --(XV)--

Column 18,
Line 63, delete "allylhydroperoxides" and insert --alkylhydroperoxides--

Column 29,
Line 59, delete "drized" and insert --dried--

Column 31,
Line 49, delete "factions" and insert --fractions--

Column 34,
Line 40, delete "was sired" and insert --was stirred--

Signed and Sealed this
Twenty-fourth Day of January, 2012

David J. Kappos
*Director of the United States Patent and Trademark Office*

Column 40,
Line 15, delete "$CH_2C_2$" and insert --$CH_2Cl_2$--

Column 62,
Table column entitled "physical data", line 10, delete "mp. 820° C." and insert --mp. 82° C.--

Column 111,
Table column entitled "$R^1$", line 35, delete "4-methylcyclohexy" and insert --4-methylcyclohexyl--

Column 143,
Line 59, delete "glutamated" and insert --glutamate--

Column 159,
Claim 7, line 40, delete "stereachemically" and insert --stereochemically--